United States Patent
Greenawalt et al.

(10) Patent No.: US 12,151,045 B2
(45) Date of Patent: Nov. 26, 2024

(54) REACTIVE DRY POWDERED HEMOSTATIC MATERIALS COMPRISING A PROTEIN AND A MULTIFUNCTIONALIZED MODIFIED POLYETHYLENE GLYCOL BASED CROSSLINKING AGENT

(71) Applicant: Davol Inc., Warwick, RI (US)

(72) Inventors: Keith Greenawalt, Milton, MA (US); Frederick H. Strickler, Jr., Boston, MA (US)

(73) Assignee: Davol Inc., Warwick, RI (US)

(*) Notice: Subject to any disclaimer, the term of this patent is extended or adjusted under 35 U.S.C. 154(b) by 155 days.

(21) Appl. No.: 17/562,282

(22) Filed: Dec. 27, 2021

(65) Prior Publication Data

US 2022/0211900 A1  Jul. 7, 2022

Related U.S. Application Data

(60) Provisional application No. 63/131,267, filed on Dec. 28, 2020.

(51) Int. Cl.
*A61L 24/00* (2006.01)
*A61L 24/04* (2006.01)
*C08G 81/02* (2006.01)

(52) U.S. Cl.
CPC ......... *A61L 24/0031* (2013.01); *A61L 24/043* (2013.01); *C08G 81/025* (2013.01); *A61L 2400/04* (2013.01)

(58) Field of Classification Search
None
See application file for complete search history.

(56) References Cited

U.S. PATENT DOCUMENTS

| | | |
|---|---|---|
| 4,002,173 A | 1/1977 | Manning et al. |
| 4,101,380 A | 7/1978 | Rubinstein et al. |
| 4,537,767 A | 8/1985 | Rothman et al. |
| 4,664,105 A | 5/1987 | Dautzenberg et al. |

(Continued)

FOREIGN PATENT DOCUMENTS

| | | |
|---|---|---|
| AU | 2007296056 A1 | 3/2008 |
| CA | 2451624 A1 | 12/2002 |

(Continued)

OTHER PUBLICATIONS

International Preliminary Report on Patentability mailed Sep. 29, 2022 for International Application No. PCT/US2021/023359.

(Continued)

*Primary Examiner* — Dominic Lazaro
(74) *Attorney, Agent, or Firm* — Wolf, Greenfield & Sacks, P.C.

(57) ABSTRACT

Compositions and methods related to powdered hemostats that crosslink during and/or after application to a bleeding site are described. The compositions may comprise a first component comprising a multifunctionalized polymeric composition (e.g., multifunctionalized polyethylene glycol) functionalized with electrophilic reactive groups, and a second component that comprises a protein such as albumin. The compositions may in certain applications act as hemostats when applied in dry powder form to a bleeding wound, whereupon the first component and the second component of the composition crosslink to form a hydrogel.

23 Claims, 10 Drawing Sheets

(56) References Cited

U.S. PATENT DOCUMENTS

| | | |
|---|---|---|
| 4,775,622 A | 10/1988 | Hitzeman et al. |
| 4,839,345 A | 6/1989 | Doi et al. |
| 4,909,251 A | 3/1990 | Seelich |
| 4,913,897 A | 4/1990 | Chvapil et al. |
| 4,914,027 A | 4/1990 | Knapp et al. |
| 4,937,193 A | 6/1990 | Hinchliffe et al. |
| 4,990,447 A | 2/1991 | Konig et al. |
| 5,037,744 A | 8/1991 | Knapp et al. |
| 5,100,784 A | 3/1992 | Latta et al. |
| 5,118,794 A | 6/1992 | Grangeorge et al. |
| 5,132,404 A | 7/1992 | Ohtani et al. |
| 5,187,261 A | 2/1993 | Latta et al. |
| 5,209,776 A | 5/1993 | Bass |
| 5,250,662 A | 10/1993 | Chang |
| 5,260,202 A | 11/1993 | Clarke et al. |
| 5,277,818 A | 1/1994 | Matsuoka et al. |
| 5,292,362 A | 3/1994 | Bass et al. |
| 5,302,697 A | 4/1994 | Goodey et al. |
| 5,324,775 A | 6/1994 | Rhee et al. |
| 5,369,020 A | 11/1994 | Sumi et al. |
| 5,380,712 A | 1/1995 | Ballance et al. |
| 5,409,815 A | 4/1995 | Nakagawa et al. |
| 5,410,016 A | 4/1995 | Hubbell et al. |
| 5,440,018 A | 8/1995 | Ohmura et al. |
| 5,476,909 A | 12/1995 | Kim et al. |
| 5,502,042 A | 3/1996 | Gruskin et al. |
| 5,503,993 A | 4/1996 | Hayasuke et al. |
| 5,514,379 A | 5/1996 | Weissleder et al. |
| 5,514,380 A | 5/1996 | Song et al. |
| 5,521,287 A | 5/1996 | Ohmura et al. |
| 5,571,801 A | 11/1996 | Segall et al. |
| 5,583,114 A | 12/1996 | Barrows et al. |
| 5,593,858 A | 1/1997 | Fleer et al. |
| 5,605,255 A | 2/1997 | Reidel et al. |
| 5,612,196 A | 3/1997 | Becquart et al. |
| 5,612,197 A | 3/1997 | Ohda et al. |
| 5,616,691 A | 4/1997 | Takahashi et al. |
| 5,627,046 A | 5/1997 | Falcone et al. |
| 5,627,052 A | 5/1997 | Schrader |
| 5,631,145 A | 5/1997 | Kobayashi et al. |
| 5,633,146 A | 5/1997 | Fleer et al. |
| 5,643,792 A | 7/1997 | Okabayashi et al. |
| 5,648,243 A | 7/1997 | Hurwitz et al. |
| 5,656,729 A | 8/1997 | Fuluhata et al. |
| 5,667,986 A | 9/1997 | Goodey et al. |
| 5,677,424 A | 10/1997 | Rucheton et al. |
| 5,679,543 A | 10/1997 | Lawlis |
| 5,691,451 A | 11/1997 | Ohya et al. |
| 5,728,553 A | 3/1998 | Goodey et al. |
| 5,733,563 A | 3/1998 | Fortier |
| 5,752,974 A | 5/1998 | Rhee |
| 5,756,313 A | 5/1998 | Okabayashi et al. |
| 5,759,819 A | 6/1998 | Kobayashi et al. |
| 5,770,229 A | 6/1998 | Tanihara et al. |
| 5,783,423 A | 7/1998 | Wood et al. |
| 5,791,352 A | 8/1998 | Reich et al. |
| 5,846,930 A | 12/1998 | Ristol Debart et al. |
| 5,849,874 A | 12/1998 | van der Laken et al. |
| 5,874,500 A | 2/1999 | Rhee et al. |
| RE36,259 E | 7/1999 | Tenold |
| 5,919,907 A | 7/1999 | Shanbrom |
| 5,962,649 A | 10/1999 | Noda et al. |
| 5,965,386 A | 10/1999 | Kerry-Williams et al. |
| 5,986,062 A | 11/1999 | Ohmura et al. |
| 5,994,507 A | 11/1999 | Pilotti et al. |
| 6,001,974 A | 12/1999 | Demmer et al. |
| 6,022,954 A | 2/2000 | Dernis et al. |
| 6,034,221 A | 3/2000 | Berezenko et al. |
| 6,043,213 A | 3/2000 | Tsubota |
| 6,051,248 A | 4/2000 | Sawhney et al. |
| 6,060,461 A | 5/2000 | Drake |
| 6,063,061 A | 5/2000 | Wallace |
| 6,113,629 A | 9/2000 | Ken |
| 6,150,504 A | 11/2000 | Van Der Laken et al. |
| 6,165,201 A | 12/2000 | Sawhney et al. |
| 6,166,130 A | 12/2000 | Rhee et al. |
| 6,177,095 B1 | 1/2001 | Sawhney et al. |
| 6,179,862 B1 | 1/2001 | Sawhney |
| 6,183,498 B1 | 2/2001 | Devore et al. |
| 6,217,894 B1 | 4/2001 | Sawhney et al. |
| 6,312,725 B1 | 11/2001 | Wallace et al. |
| 6,328,229 B1 | 12/2001 | Duronio et al. |
| 6,362,254 B2 | 3/2002 | Harris et al. |
| 6,371,975 B2 | 4/2002 | Cruise |
| 6,437,025 B1 | 8/2002 | Harris et al. |
| 6,458,147 B1 | 10/2002 | Cruise et al. |
| 6,458,889 B1 | 10/2002 | Trollsas et al. |
| 6,475,508 B1 | 11/2002 | Schwartz et al. |
| 6,495,127 B1 | 12/2002 | Wallace et al. |
| 6,504,011 B1 | 1/2003 | Van Der Laken et al. |
| 6,514,534 B1 | 2/2003 | Sawhney |
| 6,521,431 B1 | 2/2003 | Kiser et al. |
| 6,534,591 B2 | 3/2003 | Rhee et al. |
| 6,541,543 B2 | 4/2003 | Harris et al. |
| RE38,158 E * | 6/2003 | Barrows ............ A61L 24/046 424/193.1 |
| 6,576,263 B2 | 6/2003 | Truong et al. |
| 6,613,884 B1 | 9/2003 | Johansson |
| 6,617,133 B1 | 9/2003 | Noda et al. |
| 6,624,245 B2 | 9/2003 | Wallace et al. |
| 6,629,947 B1 | 10/2003 | Sahatjian et al. |
| 6,638,740 B1 | 10/2003 | Goodey et al. |
| 6,648,852 B2 | 11/2003 | Wirt et al. |
| 6,685,727 B2 | 2/2004 | Fisher et al. |
| 6,703,047 B2 | 3/2004 | Sawhney et al. |
| 6,706,690 B2 | 3/2004 | Reich |
| 6,708,847 B2 | 3/2004 | Ljungquist |
| 6,733,472 B1 | 5/2004 | Epstein et al. |
| 6,818,018 B1 | 11/2004 | Sawhney |
| 6,830,756 B2 | 12/2004 | Hnojewyj |
| 6,831,157 B2 | 12/2004 | Van Der Laken et al. |
| 6,833,408 B2 | 12/2004 | Sehl et al. |
| 6,874,657 B2 | 4/2005 | Metzner et al. |
| 6,887,974 B2 | 5/2005 | Pathak |
| 6,899,889 B1 | 5/2005 | Hnojewyj et al. |
| 6,908,749 B2 | 6/2005 | Nouchi et al. |
| RE38,827 E | 10/2005 | Barrows et al. |
| 6,969,400 B2 | 11/2005 | Rhee et al. |
| 6,989,192 B2 | 1/2006 | Husemann et al. |
| 6,994,686 B2 | 2/2006 | Cruise et al. |
| 7,001,885 B2 | 2/2006 | Adachi et al. |
| 7,008,635 B1 | 3/2006 | Coury et al. |
| 7,009,034 B2 | 3/2006 | Pathak et al. |
| 7,025,990 B2 | 4/2006 | Sawhney |
| 7,030,278 B2 | 4/2006 | Harris et al. |
| 7,057,019 B2 | 6/2006 | Pathak |
| 7,074,425 B2 | 7/2006 | Constantine et al. |
| 7,077,339 B2 | 7/2006 | Leach |
| 7,119,124 B2 | 10/2006 | Hegedus et al. |
| 7,151,135 B2 | 12/2006 | Rhee et al. |
| 7,166,577 B2 | 1/2007 | Otagiri et al. |
| 7,176,256 B2 | 2/2007 | Rhee et al. |
| 7,223,561 B2 | 5/2007 | Goodey et al. |
| 7,223,803 B2 | 5/2007 | Harris et al. |
| 7,238,364 B2 | 7/2007 | Sawhney et al. |
| 7,247,314 B2 | 7/2007 | Hnojewyj et al. |
| 7,279,001 B2 | 10/2007 | Addis et al. |
| 7,304,208 B2 | 12/2007 | Huang et al. |
| 7,307,148 B2 | 12/2007 | Bousquet-Gagnon et al. |
| 7,318,933 B2 | 1/2008 | Hnojewyj |
| 7,320,962 B2 | 1/2008 | Reich |
| 7,332,566 B2 | 2/2008 | Pathak et al. |
| 7,335,220 B2 | 2/2008 | Khosravi et al. |
| 7,347,850 B2 | 3/2008 | Sawhney et al. |
| 7,351,249 B2 | 4/2008 | Hnojewyj et al. |
| 7,423,124 B2 | 9/2008 | Belew et al. |
| 7,459,542 B2 | 12/2008 | Sang et al. |
| 7,485,719 B2 | 2/2009 | Abe et al. |
| 7,490,738 B2 | 2/2009 | Crews |
| 7,501,455 B2 | 3/2009 | Hegedus et al. |
| 7,516,872 B2 | 4/2009 | Boone et al. |
| 7,528,202 B2 | 5/2009 | Harris et al. |
| 7,592,418 B2 | 9/2009 | Pathak et al. |
| 7,597,882 B2 | 10/2009 | Pathak et al. |

(56) References Cited

U.S. PATENT DOCUMENTS

| | | |
|---|---|---|
| 7,601,515 B2 | 10/2009 | Goodey et al. |
| 7,641,075 B2 | 1/2010 | Crews |
| 7,648,713 B2 | 1/2010 | Sawhney |
| 7,714,088 B2 | 5/2010 | Harris et al. |
| 7,718,851 B2 | 5/2010 | Huang et al. |
| 7,727,547 B2 | 6/2010 | Fortune et al. |
| 7,799,767 B2 | 9/2010 | Lamberti et al. |
| 7,883,693 B2 | 2/2011 | Sehl et al. |
| 7,914,819 B1 | 3/2011 | Wen et al. |
| 7,943,570 B2 | 5/2011 | Nakajou et al. |
| 7,963,937 B2 | 6/2011 | Pauser et al. |
| 7,972,357 B2 | 7/2011 | Bettuchi |
| 7,993,877 B2 | 8/2011 | Van Urk et al. |
| 8,003,742 B2 | 8/2011 | Harris et al. |
| 8,034,367 B2 | 10/2011 | Hnojewyj |
| 8,067,031 B2 | 11/2011 | Daniloff et al. |
| 8,084,580 B2 | 12/2011 | Jorquera Nieto et al. |
| 8,088,416 B2 | 1/2012 | Jorquera Nieto et al. |
| 8,092,837 B2 | 1/2012 | Enyart et al. |
| 8,100,294 B2 | 1/2012 | May et al. |
| 8,105,622 B2 | 1/2012 | Sawhney |
| 8,119,604 B2 | 2/2012 | Gombotz et al. |
| RE43,331 E | 5/2012 | Samaritani et al. |
| 8,231,599 B2 | 7/2012 | Jorquera Nieto et al. |
| 8,236,527 B2 | 8/2012 | Chen et al. |
| 8,236,927 B2 | 8/2012 | Stange |
| 8,241,656 B2 | 8/2012 | Chudzik et al. |
| 8,252,551 B2 | 8/2012 | Sleep et al. |
| 8,257,690 B2 | 9/2012 | Chenault |
| 8,258,102 B2 | 9/2012 | Sleep |
| 8,258,264 B2 | 9/2012 | Tagawa et al. |
| 8,288,477 B2 | 10/2012 | Hadba et al. |
| 8,309,680 B2 | 11/2012 | McManus et al. |
| 8,314,195 B2 | 11/2012 | Elisseeff |
| 8,323,262 B2 | 12/2012 | D'Alessio et al. |
| 8,409,249 B2 | 4/2013 | Hnojewyj et al. |
| 8,410,189 B2 | 4/2013 | Carnahan et al. |
| 8,460,695 B2 | 6/2013 | Greenawalt |
| 8,460,708 B2 | 6/2013 | Daniloff et al. |
| 8,481,073 B2 | 7/2013 | Daniloff et al. |
| 8,512,749 B2 | 8/2013 | Sawhney et al. |
| 8,535,705 B2 | 9/2013 | Pathak et al. |
| 8,545,864 B2 | 10/2013 | Morris et al. |
| 8,545,871 B2 | 10/2013 | Arthur et al. |
| 8,563,037 B2 | 10/2013 | Rappleye et al. |
| 8,623,842 B2 | 1/2014 | Roberts et al. |
| 8,673,335 B2 | 3/2014 | Jones et al. |
| 8,703,170 B2 | 4/2014 | Hedrich et al. |
| 8,703,176 B2 | 4/2014 | Zhu et al. |
| 8,741,832 B2 | 6/2014 | Acharya et al. |
| 8,802,652 B2 | 8/2014 | Myntti et al. |
| 8,846,022 B2 | 9/2014 | Carnahan et al. |
| 8,912,168 B2 | 12/2014 | Ji et al. |
| 8,968,716 B2 | 3/2015 | Park et al. |
| 8,968,783 B2 | 3/2015 | Bennett et al. |
| 8,980,295 B2 | 3/2015 | Kao et al. |
| 9,023,379 B2 | 5/2015 | Pathak et al. |
| 9,040,093 B2 | 5/2015 | Wagner |
| 9,061,087 B2 | 6/2015 | Roberts et al. |
| 9,114,172 B2 * | 8/2015 | Rhee ................. A61L 31/145 |
| 9,345,662 B2 | 5/2016 | Sinko et al. |
| 9,345,809 B2 | 5/2016 | Falcone et al. |
| 9,375,505 B2 | 6/2016 | Hedrich et al. |
| 9,393,344 B2 | 7/2016 | Stockman et al. |
| 9,492,376 B2 | 11/2016 | Seliktar et al. |
| 9,616,088 B2 | 4/2017 | Diehn et al. |
| 9,662,400 B2 | 5/2017 | Smith et al. |
| 9,700,650 B2 | 7/2017 | Gong et al. |
| 9,707,252 B2 | 7/2017 | Hadba et al. |
| 9,708,416 B2 | 7/2017 | Malmsjo et al. |
| 9,844,597 B2 | 12/2017 | Chau et al. |
| 9,878,066 B2 | 1/2018 | Stockman et al. |
| 9,895,465 B2 | 2/2018 | Lamberti et al. |
| 9,993,577 B2 | 6/2018 | Grinstaff et al. |
| 10,172,938 B2 | 1/2019 | Kiick et al. |
| 10,314,937 B2 | 6/2019 | Ji et al. |
| 10,517,988 B1 | 12/2019 | Modak et al. |
| 10,584,184 B2 | 3/2020 | Tramontano et al. |
| 10,595,978 B2 | 3/2020 | Lavigne et al. |
| 10,905,792 B2 | 2/2021 | Laub et al. |
| 11,154,665 B2 | 10/2021 | Goodman et al. |
| 11,208,530 B2 | 12/2021 | Zhao et al. |
| 11,326,022 B2 | 5/2022 | Delaney, Jr. et al. |
| 11,739,166 B2 | 8/2023 | Greenawalt et al. |
| 2002/0022588 A1 | 2/2002 | Wilkie et al. |
| 2002/0106409 A1 | 8/2002 | Sawhney et al. |
| 2003/0023209 A1 | 1/2003 | Gruskin et al. |
| 2003/0187387 A1 | 10/2003 | Wirt et al. |
| 2003/0223957 A1 | 12/2003 | Schwartz et al. |
| 2005/0118238 A1 | 6/2005 | Zhu et al. |
| 2005/0123588 A1 | 6/2005 | Zhu et al. |
| 2005/0271727 A1 | 12/2005 | Yao |
| 2006/0078536 A1 | 4/2006 | Kodokian et al. |
| 2006/0088570 A1 | 4/2006 | Cruise et al. |
| 2006/0093648 A1 | 5/2006 | Coury et al. |
| 2006/0273109 A1 | 12/2006 | Keller |
| 2007/0065481 A1 | 3/2007 | Chudzik et al. |
| 2007/0086958 A1 | 4/2007 | Drake et al. |
| 2007/0213768 A1 | 9/2007 | Wasserman et al. |
| 2007/0248653 A1 | 10/2007 | Cochrum et al. |
| 2008/0038313 A1 | 2/2008 | Addis et al. |
| 2008/0215088 A1 | 9/2008 | Hnojewyj et al. |
| 2008/0293910 A1 | 11/2008 | Kapiamba et al. |
| 2009/0062233 A1 | 3/2009 | Ji et al. |
| 2009/0152267 A1 | 6/2009 | May et al. |
| 2009/0285780 A1 | 11/2009 | Lee |
| 2009/0291911 A1 | 11/2009 | Myntti et al. |
| 2010/0087851 A1 | 4/2010 | Jones et al. |
| 2010/0100099 A1 | 4/2010 | Reilly et al. |
| 2010/0168007 A1 | 7/2010 | Cruise et al. |
| 2010/0204718 A1 | 8/2010 | Rappleye et al. |
| 2010/0217231 A1 | 8/2010 | Ilan et al. |
| 2010/0274279 A1 | 10/2010 | Delmotte |
| 2010/0297235 A1 | 11/2010 | Hnojewyj |
| 2011/0027216 A1 | 2/2011 | Chenault |
| 2011/0104280 A1 | 5/2011 | Hnojewyj |
| 2011/0123476 A1 | 5/2011 | Kapiamba et al. |
| 2011/0125089 A1 | 5/2011 | Senderoff et al. |
| 2011/0150821 A1 | 6/2011 | Daniloff et al. |
| 2011/0166596 A1 | 7/2011 | Delmotte |
| 2011/0272436 A1 | 11/2011 | Vogt et al. |
| 2011/0274725 A1 | 11/2011 | Breton et al. |
| 2011/0282464 A1 | 11/2011 | Sargeant et al. |
| 2012/0035129 A1 | 2/2012 | Wagman |
| 2012/0041481 A1 | 2/2012 | Daniloff et al. |
| 2012/0101519 A1 | 4/2012 | Hill et al. |
| 2012/0156259 A1 | 6/2012 | Rau et al. |
| 2012/0244198 A1 | 9/2012 | Malmsjo et al. |
| 2012/0315305 A1 | 12/2012 | Koopman et al. |
| 2013/0090291 A1 | 4/2013 | Gulle et al. |
| 2013/0096063 A1 | 4/2013 | Hedrich et al. |
| 2013/0096082 A1 | 4/2013 | Harkamp et al. |
| 2013/0209659 A1 | 8/2013 | Racenet et al. |
| 2013/0261192 A1 | 10/2013 | Yang et al. |
| 2014/0105950 A1 | 4/2014 | Hardy et al. |
| 2014/0171883 A1 | 6/2014 | Roberts et al. |
| 2015/0306277 A1 | 10/2015 | Pathak et al. |
| 2017/0056550 A1 | 3/2017 | Hoemann et al. |
| 2017/0106119 A1 | 4/2017 | Skinner et al. |
| 2017/0252479 A1 | 9/2017 | Ji et al. |
| 2018/0036338 A1 | 2/2018 | Sanders et al. |
| 2018/0344898 A1 | 12/2018 | Kronenthal et al. |
| 2019/0001018 A1 | 1/2019 | Stockman et al. |
| 2019/0388516 A1 | 12/2019 | Floyd et al. |
| 2019/0388577 A1 | 12/2019 | Chandrashekhar-Bhat et al. |
| 2019/0388580 A1 | 12/2019 | Guo et al. |
| 2019/0388665 A1 | 12/2019 | Christakis et al. |
| 2020/0030481 A1 | 1/2020 | Hedrich et al. |
| 2020/0046877 A1 | 2/2020 | Kageyama et al. |
| 2020/0102446 A1 | 4/2020 | Dowling |
| 2020/0121825 A1 | 4/2020 | Dowling |
| 2020/0139021 A1 | 5/2020 | Ilan et al. |
| 2021/0060204 A1 | 3/2021 | Ji et al. |
| 2022/0001075 A1 | 1/2022 | Greenawalt et al. |

(56) References Cited

U.S. PATENT DOCUMENTS

| | | | |
|---|---|---|---|
| 2022/0002444 A1 | 1/2022 | Greenawalt et al. | |
| 2022/0323637 A1 | 10/2022 | Greenawalt et al. | |
| 2023/0094351 A1 | 3/2023 | Addison et al. | |

FOREIGN PATENT DOCUMENTS

| | | |
|---|---|---|
| CA | 2581093 A1 | 3/2006 |
| CN | 100556467 C | 11/2009 |
| CN | 101594890 A | 12/2009 |
| CN | 101791436 A | 8/2010 |
| CN | 101497670 B | 4/2012 |
| CN | 105838299 A | 8/2016 |
| CN | 110464869 A | 11/2019 |
| CN | 111068101 A | 4/2020 |
| CN | 111317857 A | 6/2020 |
| CN | 111317858 A | 6/2020 |
| CN | 111714683 A | 9/2020 |
| CN | 111714684 A | 9/2020 |
| CN | 111714686 A | 9/2020 |
| CN | 111714688 A | 9/2020 |
| CN | 111729125 A | 10/2020 |
| CN | 112138205 A | 12/2020 |
| CN | 112494712 A | 3/2021 |
| CN | 108744019 B | 5/2021 |
| CN | 113061255 A | 7/2021 |
| CN | 110269954 B | 8/2021 |
| DE | 3502998 A1 | 7/1986 |
| EP | 0258067 B1 | 3/1993 |
| EP | 0420007 B1 | 1/1994 |
| EP | 0402205 B1 | 12/1995 |
| EP | 0701822 A2 | 3/1996 |
| EP | 0705298 A1 | 4/1996 |
| EP | 0422769 B1 | 4/1997 |
| EP | 0504823 B1 | 6/1997 |
| EP | 0367220 B1 | 1/1998 |
| EP | 0428758 B1 | 1/1998 |
| EP | 0584166 B1 | 3/1998 |
| EP | 0597035 B1 | 9/1998 |
| EP | 0876165 A1 | 11/1998 |
| EP | 0498133 B1 | 5/1999 |
| EP | 0625202 B1 | 7/1999 |
| EP | 0524681 B1 | 11/1999 |
| EP | 0559895 B1 | 1/2001 |
| EP | 0764209 B1 | 1/2001 |
| EP | 0828759 B1 | 1/2001 |
| EP | 0570916 B1 | 1/2002 |
| EP | 1185288 A1 | 3/2002 |
| EP | 0655503 B1 | 7/2002 |
| EP | 1218437 A1 | 7/2002 |
| EP | 0736605 B1 | 4/2003 |
| EP | 0341103 B2 | 8/2003 |
| EP | 0637317 B1 | 8/2003 |
| EP | 0699687 B1 | 1/2004 |
| EP | 0749478 B1 | 2/2004 |
| EP | 1031578 B1 | 4/2004 |
| EP | 1610829 A1 | 1/2006 |
| EP | 1504031 B1 | 8/2006 |
| EP | 1329462 B1 | 12/2006 |
| EP | 1718673 B1 | 9/2007 |
| EP | 1149163 B1 | 12/2008 |
| EP | 1710250 B1 | 4/2009 |
| EP | 2093245 A2 | 8/2009 |
| EP | 1479393 B1 | 8/2010 |
| JP | 5232347 B2 | 7/2013 |
| KR | 101507589 B1 | 4/2015 |
| KR | 102220832 B1 | 2/2021 |
| WO | WO 90/13540 A1 | 11/1990 |
| WO | WO 93/15204 A1 | 8/1993 |
| WO | WO 94/03155 A1 | 2/1994 |
| WO | WO 97/22371 A1 | 6/1997 |
| WO | WO 97/29715 A1 | 8/1997 |
| WO | WO 98/29099 A2 | 7/1998 |
| WO | WO 2006/113845 A1 | 10/2006 |
| WO | WO 2007/084609 A2 | 7/2007 |
| WO | WO 2012/123728 A2 | 9/2012 |
| WO | WO 2019/137414 A1 | 7/2019 |
| WO | WO 2020/004813 A1 | 1/2020 |
| WO | WO 2020/019880 A1 | 1/2020 |
| WO | WO 2020/044237 A1 | 3/2020 |
| WO | WO 2020/068814 A1 | 4/2020 |
| WO | WO 2020/197969 A1 | 10/2020 |
| WO | WO 2020/264188 A1 | 12/2020 |
| WO | WO 2021/027219 A1 | 2/2021 |
| WO | WO 2021/128050 A1 | 7/2021 |
| WO | WO 2021/188904 A1 | 9/2021 |
| WO | WO 2021/189024 A1 | 9/2021 |

OTHER PUBLICATIONS

Extended European Search Report mailed Jun. 22, 2023 for European Application No. 20830714.0 and claims as pending as of Jun. 22, 2023.

International Preliminary Report on Patentability mailed Jul. 13, 2023 for International Application No. PCT/US2021/065204.

Anraku et al., Stabilizing mechanisms in commercial albumin preparations: octanoate and N-acetyl-L-tryptophanate protect human serum albumin against heat and oxidative stress. Biochim Biophys Acta. Oct. 1, 2004;1702(1):9-17. doi: 10.1016/j.bbapap.2004.07.002.

Cai et al., The Proof Is in the Pidan: Generalizing Proteins as Patchy Particles. ACS Cent Sci. Jul. 25, 2018;4(7):840-853. doi: 10.1021/acscentsci.8b00187. Epub Jun. 28, 2018.

Cleland et al., Polyethylene glycol enhanced protein refolding. Biotechnology (NY). Sep. 1992;10(9):1013-9. doi: 10.1038/nbt0992-1013.

Das et al., Modified biopolymer-dextrin based crosslinked hydrogels: application in controlled drug delivery. RSC Adv. Feb. 9, 2015;5:25014-50. doi: 10.1039/C4RA16103C.

Delval et al., Preparation, Characterization and Sorption Properties of Crosslinked Starch-Based Exchangers. J Carb Polym. Apr. 2005;60(1):67-75. doi: 10.1016/j.carbpol.2004.11.025.

Li et al., A biodegradable starch hydrogel synthesized via thiol-ene click chemistry. Polym Degrad Stab. Mar. 2017;137:75-82. doi: 10.1016/j.polymdegradstab.2016.07.015.

Lim et al., Chlorin e6-embedded starch nanogels for improved photodynamic tumor ablation. Polym Adv Technol. Nov. 2018;29(11):2766-73. doi: 10.1002/pat.4399.

U.S. Appl. No. 17/365,795, filed Jul. 1, 2021, Greenawalt et al.

U.S. Appl. No. 17/365,749, filed Jul. 1, 2021, Greenawalt et al.

U.S. Appl. No. 17/622,198, filed Dec. 22, 2021, Greenawalt et al.

International Search Report and Written Opinion mailed Jul. 8, 2021 for International Application No. PCT/US2021/023359.

International Search Report and Written Opinion mailed Oct. 29, 2020 for International Application No. PCT/US2020/039660.

International Preliminary Report on Patentability mailed Jan. 6, 2022 for International Application No. PCT/US2020/039660.

[No Author Listed], Tridynetm Vascular Sealant. C.R. Bard, Inc. 2015. 21 pages.

Abuchowski et al., Cancer therapy with chemically modified enzymes. I. Antitumor properties of polyethylene glycol-asparaginase conjugates. Cancer Biochem Biophys. Jun. 1984;7(2):175-86.

Calabretta et al., Antibacterial activities of poly(amidoamine) dendrimers terminated with amino and poly(ethylene glycol) groups. Biomacromolecules. Jun. 2007;8(6):1807-11. doi: 10.1021/bm0701088. Epub May 19, 2007.

Carlstedt et al., Hydration and the phase diagram of acid hydrolyzed potato starch. Carbohydr Polym. Nov. 4, 2014;112:569-77. doi: 10.1016/j.carbpol.2014.06.037. Epub Jun. 21, 2014. Supplementary Material, 6 pages.

Conti et al., A proposed new method for the crosslinking of chitosan microspheres. Drug Deliv. 1998;5(2):87-93. doi: 10.3109/10717549809031383.

Diaz et al., Partially PEGylated PAMAM dendrimers as solubility enhancers of Silybin. Pharm Dev Technol. Sep. 2018;23(7):689-696. doi: 10.1080/10837450.2017.1315134. Epub Apr. 19, 2017.

Elchinger et al., Polysaccharides: The "Click" Chemistry Impact. Polymers. Sep. 27, 2011;3(4):1607-51. doi: 10.3390/polym3041607.

(56) References Cited

OTHER PUBLICATIONS

El-Sayed et al., New approach for immobilization of 3-aminopropyltrimethoxysilane and TiO2 nanoparticles into cellulose for BJ1 skin cells proliferation. Carbohydr Polym. Nov. 1, 2018;199:193-204. doi: 10.1016/j.carbpol.2018.07.004. Epub Jul. 9, 2018.

Ereth et al., Microporous polysaccharide hemospheres do not inhibit bone healing compared to bone wax or microfibrillar collagen. Orthopedics. Mar. 2008;31(3):222. doi: 10.3928/01477447-20080301-10.

Fogh-Andersen et al., Ionic binding, net charge, and Donnan effect of human serum albumin as a function of pH. Clin Chem. Jan. 1993;39(1):48-52.

Fuller, C., Reduction of intraoperative air leaks with Progel in pulmonary resection: a comprehensive review. J Cardiothorac Surg. Apr. 16, 2013;8:90. doi: 10.1186/1749-8090-8-90.

Hamdi et al., Enzymatic degradation of epichlorohydrin crosslinked starch microspheres by alpha-amylase. Pharm Res. Jun. 1999;16(6):867-75. doi: 10.1023/a:1018878120100.

Hamdi et al., Formulation of epichlorohydrin cross-linked starch microspheres. J Microencapsul. May-Jun. 2001;18(3):373-83. doi: 10.1080/02652040010019505.

Haroon et al., Chemical modification of starch and its application as an adsorbent material. R. Soc. Chem., Aug. 12, 2016;6:78264-85. doi: https://doi.org/10.1039/C6RA16795K.

Hasegawa et al., 'Click chemistry' on polysaccharides: a convenient, general, and monitorable approach to develop (1-->3)-beta-D-glucans with various functional appendages. Carbohydr Res. Jan. 16, 2006;341(1):35-40. doi: 10.1016/j.carres.2005.10.009. Epub Nov. 14, 2005.

Holmes et al., Antimicrobial efficacy and mechanism of action of poly(amidoamine) (PAMAM) dendrimers against opportunistic pathogens. Int J Antimicrob Agents. Apr. 2019;53(4):500-507. doi: 10.1016/j.ijantimicag.2018.12.012. Epub Dec. 30, 2018.

Jevprasesphant et al., The influence of surface modification on the cytotoxicity of PAMAM dendrimers. Int J Pharm. Feb. 18, 2003;252(1-2):263-6. doi: 10.1016/s0378-5173(02)00623-3.

Kobayashi et al., In vivo evaluation of a new sealant material on a rat lung air leak model. J Biomed Mater Res. 2001;58(6):658-65. doi: 10.1002/jbm.1066.

Koga et al., Chemically-modified cellulose paper as a microstructured catalytic reactor. Molecules. Jan. 15, 2015;20(1):1495-508. doi: 10.3390/molecules20011495.

Koga et al., In situ modification of cellulose paper with amino groups for catalytic applications. J. Mater. Chem. May 27, 2011;21:9356-61. doi: https://doi.org/10.1039/C1JM10543D.

Kuniak et al., Study of the Crosslinking Reaction between Epichlorohydrin and Starch. Starch. 1972;24(4):110-116. doi: 10.1002/star.19720240404.

Lopez et al., Antibacterial activity and cytotoxicity of PEGylated poly(amidoamine) dendrimers. Mol Biosyst. Oct. 2009;5(10):1148-56. doi: 10.1039/b904746h. Epub Jul. 3, 2009. Author Manuscript, 17 pages.

Qi et al., PEG-conjugated PAMAM dendrimers mediate efficient intramuscular gene expression. AAPS J. Sep. 2009;11(3):395-405. doi: 10.1208/s12248-009-9116-1. Epub May 29, 2009.

Rostami et al., Peptide-conjugated PEGylated PAMAM as a highly affinitive nanocarrier towards HER2-overexpressing cancer cells. RSC Adv. Oct. 21, 2016;6:107337-107343. doi: 10.1039/C6RA19552K.

Sadeghi et al., Evaluation of different parameters effect on maltodextrin production by alpha-amylase Termamyl 2-x, 2008, World Applied Sciences Journal, 3(1):34-39.

Schmitz et al., Use of a plant-based polysaccharide hemostat for the treatment of sternal bleeding after median sternotomy. J Cardiothorac Surg. Apr. 24, 2015;10:59. doi: 10.1186/s13019-015-0263-4.

Shao et al., Comparison of generation 3 polyamidoamine dendrimer and generation 4 polypropylenimine dendrimer on drug loading, complex structure, release behavior, and cytotoxicity. Int J Nanomedicine. 2011;6:3361-72. doi: 10.2147/IJN.S27028. Epub Dec. 16, 2011.

Suwanprateeb et al., Preparation and characterization of PEG-PPG-PEG copolymer/pregelatinized starch blends for use as resorbable bone hemostatic wax. J Mater Sci Mater Med. Dec. 2013;24(12):2881-8. doi: 10.1007/s10856-013-5027-x. Epub Aug. 17, 2013.

Tankam et al., Alkynyl polysaccharides: synthesis of propargyl potato starch followed by subsequent derivatizations. Carbohydr Res. Oct. 15, 2007;342(14):2049-60. doi: 10.1016/j.carres.2007.05.017. Epub May 18, 2007.

Wang et al., Preparation of amino-functionalized regenerated cellulose membranes with high catalytic activity. Int J Biol Macromol. Sep. 2017;102:944-951. doi: 10.1016/j.ijbiomac.2017.04.096. Epub Apr. 27, 2017.

Xue et al., Amino-terminated generation 2 poly(amidoamine) dendrimer as a potential broad-spectrum, nonresistance-inducing antibacterial agent. AAPS J. Jan. 2013;15(1):132-42. doi: 10.1208/s12248-012-9416-8. Epub Nov. 8, 2012.

International Search Report and Written Opinion mailed Apr. 4, 2022 for International Application No. PCT/US2021/065204.

Overby et al., Influence of Poly(Ethylene Glycol) End Groups on Poly(Ethylene Glycol)-Albumin System Properties as a Potential Degradable Tissue Scaffold. J. Functional Biomat. Dec. 24, 2018;10(1):1-12.

\* cited by examiner

REACTIVE DRY POWDERED HEMOSTATIC MATERIALS COMPRISING A PROTEIN AND A MULTIFUNCTIONALIZED MODIFIED POLYETHYLENE GLYCOL BASED CROSSLINKING AGENT

RELATED APPLICATIONS

This application claims priority under 35 U.S.C. § 119(e) to U.S. Provisional Patent Application No. 63/131,267, filed Dec. 28, 2020, and entitled "Reactive Dry Powder Hemostatic Materials Comprising a Protein and a Multifunctionalized Polyethylene Glycol Based Crosslinking Agent," which is incorporated herein by reference in its entirety for all purposes.

TECHNICAL FIELD

Compositions and methods related to powdered hemostats that crosslink during and/or after application to a bleeding site are generally described.

BACKGROUND

Existing powdered hemostats such as degradable starch microspheres (DSMs) or oxidized regenerative cellulose (ORC) and flowable hemostats such as liquid thrombin or fibrin glue can suffer from poor tissue adherence and may not be sufficiently effective when used for certain bleeding/wound sites. This may be due to a lack of absorbency, insufficient tissue adherence and/or cohesivity at the wound site to resist being washed away in the case of powdered hemostats. Additionally, typical conventional hemostats do not form a strong hydrogel network. This can create a need for aggressive or prolonged manual compression to keep the products in place after application to a bleeding site, making it challenging for surgeons to continue to operate in the same area. Accordingly, improved hemostatic compositions and methods would be desirable.

SUMMARY

Compositions and methods related to powdered hemostats that crosslink during and/or after application to a bleeding site are generally described. The subject matter of the present invention involves, in some cases, interrelated products, alternative solutions to a particular problem, and/or a plurality of different uses of one or more systems and/or articles.

In one aspect, dry, powdered, crosslinking hemostatic compositions are described. In some embodiments, a dry, powdered, crosslinking hemostatic composition comprises a first component comprising a multifunctionalized polymeric composition, the multifunctionalized polymeric composition comprising multiple electrophilic groups; and a second component comprising a protein, wherein the second component, when dissolved in deionized water, can produce a pH of a resulting solution of greater than or equal to 8, wherein upon exposure to an aqueous liquid, crosslinking of the first component and the second component is initiated to form a hemostatic hydrogel.

In some embodiments, a dry, powdered, crosslinking hemostatic composition comprises:

a first component comprising a difunctionalized polyalkylene oxide-based component of the formula:

G-LM-PEG-LM-G;

wherein:
PEG is polyethylene glycol;
each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and
each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl; and
a second component comprising a protein, wherein the second component, when dissolved in deionized water, can produce a pH of a resulting solution of greater than or equal to 8,
wherein upon exposure to an aqueous liquid, crosslinking of the first component and the second component is initiated to form a hemostatic hydrogel.

In some embodiments, a dry, powdered, crosslinking hemostatic composition comprises a first component comprising a multifunctionalized polymeric composition, the multifunctionalized polymeric composition comprising multiple electrophilic groups; and a second component comprising a protein in a basic state, wherein upon exposure to an aqueous liquid, crosslinking of the first component and the second component is initiated to form a hemostatic hydrogel.

In some embodiments, a dry, powdered, crosslinking hemostatic composition comprises:

a first component comprising a difunctionalized polyalkylene oxide-based component of the formula:

G-LM-PEG-LM-G;

wherein:
PEG is polyethylene glycol;
each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl; and a second component comprising a protein in a basic state, wherein upon exposure to an aqueous liquid, crosslinking of the first component and the second component is initiated to form a hemostatic hydrogel.

In some embodiments, a dry, powdered, crosslinking hemostatic composition comprises a first component comprising a multifunctionalized polymeric composition, the multifunctionalized polymeric composition comprising multiple electrophilic groups; and a second component comprising an at least partially deprotonated protein; wherein upon exposure to an aqueous liquid, crosslinking of the first component and the second component is initiated to form a hemostatic hydrogel.

In some embodiments, a dry, powdered, crosslinking hemostatic composition comprises:

a first component comprising a difunctionalized polyalkylene oxide-based component of the formula:

G-LM-PEG-LM-G;

wherein:
PEG is polyethylene glycol;
each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl; and a second component comprising an at least partially deprotonated protein;

wherein upon exposure to an aqueous liquid, crosslinking of the first component and the second component is initiated to form a hemostatic hydrogel.

In some embodiments, a dry, powdered, crosslinking hemostatic composition comprises a first component comprising a multifunctionalized polymeric composition, the multifunctionalized polymeric composition comprising multiple electrophilic groups; and a second component comprising a protein, wherein upon exposure of 0.5 g of the composition to 1.0 mL of 0.01 M phosphate buffered saline, crosslinking of the first component and the second component is initiated to form a hemostatic hydrogel having a surface pH of less than or equal to 8.

In some embodiments, a dry, powdered, crosslinking hemostatic composition comprises:

a first component comprising a difunctionalized polyalkylene oxide-based component of the formula:

G-LM-PEG-LM-G;

wherein:
PEG is polyethylene glycol;
each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl; and a second component comprising a protein,
wherein upon exposure of 0.5 g of the composition to 1.0 mL of 0.01 M phosphate buffered saline, crosslinking of the first component and the second component is initiated to form a hemostatic hydrogel having a surface pH of less than or equal to 8.

In another aspect, kits are provided. In some embodiments, a kit contains ingredients from which a dry, powdered, crosslinking hemostatic composition can be formed. In some embodiments, the kit comprises the first component and the second component, wherein the first component and the second component are packaged separately.

In another aspect, methods for controlling bleeding are provided. In some embodiments, a method comprises applying a crosslinkable dry powder composition to a bleeding/wound site; wherein the crosslinkable dry powder composition comprises a first component comprising a multifunctionalized polymeric composition, the multifunctionalized polymeric composition comprising multiple electrophilic groups; and a second component comprising a protein, wherein the second component, when dissolved in deionized water, can produce a pH of a resulting solution of greater than or equal to 8; and allowing the dry powder composition to crosslink into a hemostatic hydrogel upon exposure to the bleeding/wound site capable of stopping or reducing bleeding at the bleeding/wound site.

In some embodiments, a method for controlling bleeding comprises:
applying a crosslinkable dry powder composition to a bleeding/wound site;
wherein the crosslinkable dry powder composition comprises:
a first component comprising a difunctionalized polyalkylene oxide-based component of the formula:

G-LM-PEG-LM-G;

wherein:
PEG is polyethylene glycol;
each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and
each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl; and
a second component comprising a protein, wherein the second component, when dissolved in deionized water, can produce a pH of a resulting solution of greater than or equal to 8; and
allowing the dry powder composition to crosslink into a hemostatic hydrogel upon exposure to the bleeding/wound site capable of stopping or reducing bleeding at the bleeding/wound site.

In some embodiments, a method for controlling bleeding comprises applying a crosslinkable dry powder composition to a bleeding/wound site; wherein the crosslinkable dry powder composition comprises a first component comprising a multifunctionalized polymeric composition, the multifunctionalized polymeric composition comprising multiple electrophilic groups; and a second component comprising a protein in a basic state; and allowing the dry powder composition to crosslink into a hemostatic hydrogel upon exposure to the bleeding/wound site capable of stopping or reducing bleeding at the bleeding/wound site.

In some embodiments, a method for controlling bleeding comprises:
applying a crosslinkable dry powder composition to a bleeding/wound site;
wherein the crosslinkable dry powder composition comprises:
a first component comprising a difunctionalized polyalkylene oxide-based component of the formula:

G-LM-PEG-LM-G;

wherein:
PEG is polyethylene glycol;
each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and
each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl; and
a second component comprising a protein in a basic state; and
allowing the dry powder composition to crosslink into a hemostatic hydrogel upon exposure to the bleeding/wound site capable of stopping or reducing bleeding at the bleeding/wound site.

In some embodiments, a method for controlling bleeding comprises applying a crosslinkable dry powder composition to a bleeding/wound site; wherein the crosslinkable dry powder composition comprises a first component comprising a multifunctionalized polymeric composition, the multifunctionalized polymeric composition comprising multiple electrophilic groups; and a second component comprising an at least partially deprotonated protein; and allowing the dry powder composition to crosslink into a hemostatic hydrogel upon exposure to the bleeding/wound site capable of stopping or reducing bleeding at the bleeding/wound site.

In some embodiments, a method for controlling bleeding comprises:
applying a crosslinkable dry powder composition to a bleeding/wound site;
wherein the crosslinkable dry powder composition comprises:
a first component comprising a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —(CH$_2$)$_b$—C(O)— where b is an integer from 1 to 10, a diester radical of the formula —C(O)—(CH$_2$)$_c$—C(O)— where c is an integer from 1 to 10 and where the aliphatic portion of the radical may be saturated or unsaturated, a dicarbonate diradical of the formula —C(O)—O—(CH$_2$)$_d$—O—C(O)— where d is an integer from 1 to 10, an amide containing diradical of the formula —N(H)—C(O)—(CH$_2$)$_d$—C(O)— where d is an integer from 1 to 10, an amide containing diradical of the formula —(CH$_2$)$_c$—C(O)—N(H)—(CH$_2$)$_d$— where c is an integer from 1 to 10 and d is an integer from 1 to 10, and an oligomeric diradical represented by the formulas —R—C(O)—, —R—C(O)—(CH$_2$)$_c$—C(O)—, —R—C(O)—O—(CH$_2$)$_d$—O—C(O)—, —R—N(H)—C(O)—(CH$_2$)$_d$—C(O)—, or —R—(CH$_2$)$_c$—C(O)—N(H)—(CH$_2$)$_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl; and a second component comprising an at least partially deprotonated protein; and allowing the dry powder composition to crosslink into a hemostatic hydrogel upon exposure to the bleeding/wound site capable of stopping or reducing bleeding at the bleeding/wound site.

In some embodiments, a method for controlling bleeding comprises applying a crosslinkable dry powder composition to a bleeding/wound site; wherein the crosslinkable dry powder composition comprises a first component comprising a multifunctionalized polymeric composition, the multifunctionalized polymeric composition comprising multiple electrophilic groups; and a second component comprising a protein; and allowing the dry powder composition to crosslink into a hemostatic hydrogel having a surface pH of less than or equal to 8 upon exposure to the bleeding/wound site capable of stopping or reducing bleeding at the bleeding/wound site.

In some embodiments, a method for controlling bleeding, comprises:

applying a crosslinkable dry powder composition to a bleeding/wound site;

wherein the crosslinkable dry powder composition comprises:

a first component comprising a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —(CH$_2$)$_b$—C(O)— where b is an integer from 1 to 10, a diester radical of the formula —C(O)—(CH$_2$)$_c$—C(O)— where c is an integer from 1 to 10 and where the aliphatic portion of the radical may be saturated or unsaturated, a dicarbonate diradical of the formula —C(O)—O—(CH$_2$)$_d$—O—C(O)— where d is an integer from 1 to 10, an amide containing diradical of the formula —N(H)—C(O)—(CH$_2$)$_d$—C(O)— where d is an integer from 1 to 10, an amide containing diradical of the formula —(CH$_2$)$_c$—C(O)—N(H)—(CH$_2$)$_d$— where c is an integer from 1 to 10 and d is an integer from 1 to 10, and an oligomeric diradical represented by the formulas —R—C(O)—, —R—C(O)—(CH$_2$)$_c$—C(O)—, —R—C(O)—O—(CH$_2$)$_d$—O—C(O)—, —R—N(H)—C(O)—(CH$_2$)$_d$—C(O)—, or —R—(CH$_2$)$_c$—C(O)—N(H)—(CH$_2$)$_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl; and a second component comprising a protein; and allowing the dry powder composition to crosslink into a hemostatic hydrogel having a surface pH of less than or equal to 8 upon exposure to the bleeding/wound site capable of stopping or reducing bleeding at the bleeding/wound site.

In some embodiments, methods for preparing a protein for use in a dry, powdered, crosslinking hemostatic composition are provided. In some embodiments, a method is for preparing a protein for use in a dry, powdered, crosslinking hemostatic composition comprising a first component comprising a multifunctionalized polymeric composition, the multifunctionalized polymeric composition comprising multiple electrophilic groups; the improvement comprising removing water from a preparatory aqueous solution comprising an at least partially dissolved form of the protein, thereby forming a solid form of the protein, wherein the preparatory aqueous solution has a pH of greater than or equal to 8.

In some embodiments, a method is for preparing a protein for use in a dry, powdered, crosslinking hemostatic composition comprising a first component comprising a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —(CH$_2$)$_b$—C(O)— where b is an integer from 1 to 10, a diester radical of the formula —C(O)—(CH$_2$)$_c$—C(O)— where c is an integer from 1 to 10 and where the aliphatic portion of the radical may be saturated or unsaturated, a dicarbonate diradical of the formula —C(O)—O—(CH$_2$)$_d$—O—C(O)— where d is an integer from 1 to 10, an amide containing diradical of the formula —N(H)—C(O)—(CH$_2$)$_d$—C(O)— where d is an integer from 1 to 10, an amide containing diradical of the formula —(CH$_2$)$_c$—C(O)—N(H)—(CH$_2$)$_d$— where c is an integer from 1 to 10 and d is an integer from 1 to 10, and an oligomeric diradical represented by the formulas —R—C(O)—, —R—C (O)—(CH$_2$)$_c$—C(O)—, —R—C(O)—O—(CH$_2$)$_d$—O—C(O)—, —R—N(H)—C(O)—(CH$_2$)$_d$—C(O)—, or —R—(CH$_2$)$_c$—C(O)—N(H)—(CH$_2$)$_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl;

the improvement comprising:

removing water from a preparatory aqueous solution comprising an at least partially dissolved form of the protein, thereby forming a solid form of the protein, wherein the preparatory aqueous solution has a pH of greater than or equal to 8.

In certain embodiments, a dry, powdered, crosslinking hemostatic composition is described, wherein the composition comprises a first component comprising a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —(CH$_2$)$_b$—C(O)— where b is an integer from 1 to 10, a diester radical of the formula —C(O)—(CH$_2$)$_c$—C(O)— where c is an integer from 1 to 10 and where the aliphatic portion of the radical may be saturated or unsaturated, a dicarbonate diradical of the formula —C(O)—O—(CH$_2$)$_d$—O—C(O)— where d is an integer from 1 to 10, an amide containing diradical of the formula —N(H)—C(O)—(CH$_2$)$_d$—C(O)— where d is an integer from 1 to 10, an amide containing diradical of the formula —(CH$_2$)$_c$—C(O)—N(H)—(CH$_2$)$_d$— where c is an integer from 1 to 10 and d is an integer from 1 to 10, and an oligomeric diradical represented by the formulas —R—C(O)—, —R—C(O)—(CH$_2$)$_c$—C(O)—, —R—C(O)—O—(CH$_2$)$_d$—O—C(O)—, —R—N(H)—C(O)—(CH$_2$)$_d$—C(O)—, or —R—(CH$_2$)$_c$—C(O)—N(H)—(CH$_2$)$_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl; and a second component comprising a protein that is capable of crosslinking with the first component, and a crosslinking initiator that initiates crosslinking of the first component with the protein, wherein upon exposure to an aqueous liquid, crosslinking is initiated to form a hemostatic hydrogel.

In some embodiments, a method for controlling bleeding is described, the method comprising applying a crosslinkable dry powder composition to a bleeding/wound site, wherein the crosslinkable dry powder composition comprises a first component comprising a difunctionalized polyalkylene oxide-based composition of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —(CH$_2$)$_b$—C(O)— where b is an integer from 1 to 10, a diester radical of the formula —C(O)—(CH$_2$)$_c$—C(O)— where c is an integer from 1 to 10 and where the aliphatic portion of the radical may be saturated or unsaturated, a dicarbonate diradical of the formula —C(O)—O—(CH$_2$)$_d$—O—C(O)— where d is an integer from 1 to 10, an amide containing diradical of the formula —N(H)—C(O)—(CH$_2$)$_d$—C(O)— where d is an integer from 1 to 10, an amide containing diradical of the formula —(CH$_2$)$_c$—C(O)—N(H)—(CH$_2$)$_d$— where c is an integer from 1 to 10 and d is an integer from 1 to 10, and an oligomeric diradical represented by the formulas —R—C(O)—, —R—C(O)—(CH$_2$)$_c$—C(O)—, —R—C(O)—O—(CH$_2$)$_d$—O—C(O)—, —R—N(H)—C(O)—(CH$_2$)$_d$—C(O)—, or —R—(CH$_2$)$_c$—C(O)—N(H)—(CH$_2$)$_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments;

each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl; and a second component comprising a protein that is capable of crosslinking with the first component, and a crosslinking initiator that initiates crosslinking of the first component with the protein, and allowing the dry powder composition to crosslink into a hemostatic hydrogel upon exposure to the bleeding/wound site capable of stopping or reducing bleeding at the bleeding/wound site.

According to some embodiments, a dry, powdered, crosslinking hemostatic composition comprises a first component comprising a difunctionalized polymeric composition selected from the group consisting of:

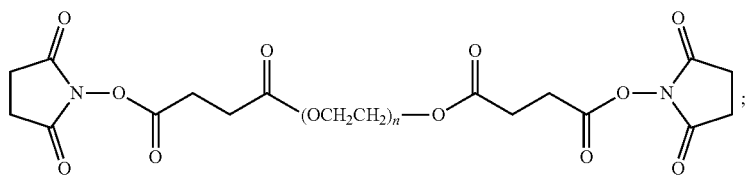

Poly(ethylene glycol) disuccinimidyl succinate, I

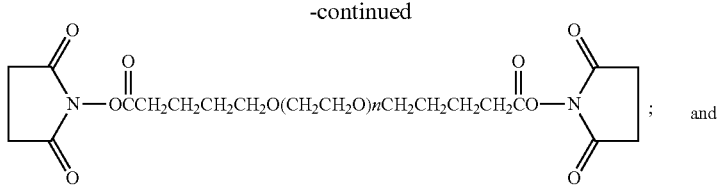

PEG disuccinimidyl valerate

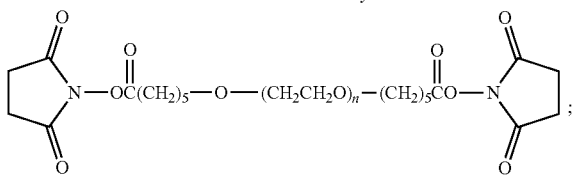

PEG disuccinimidyl hexanoate and a second component comprising a protein, wherein upon exposure to an aqueous liquid, crosslinking of the first component and the second component is initiated to form a hemostatic hydrogel.

According to certain embodiments, a method for controlling bleeding comprises applying a dry powder composition to a bleeding/wound site, wherein the dry powder composition comprises a first component comprising a difunctionalized polymeric composition selected from the group consisting of:

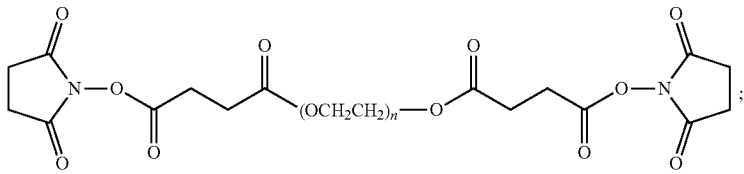

Poly(ethylene glycol) disuccinimidyl succinate, I

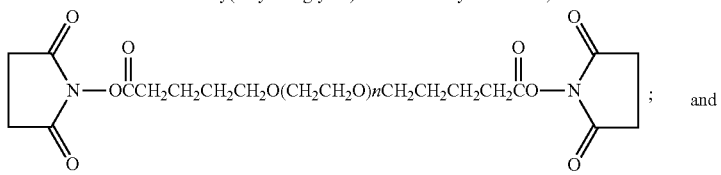

PEG disuccinimidyl valerate

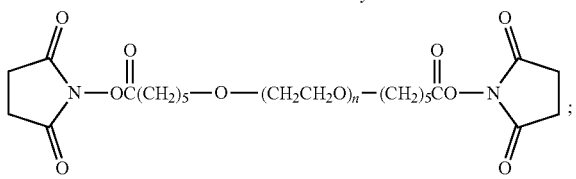

PEG disuccinimidyl hexanoate and a second component comprising a protein, and allowing the dry powder composition to crosslink into a hemostatic hydrogel upon exposure to the bleeding/wound site, wherein the hemostatic hydrogel is capable of stopping or reducing bleeding at the bleeding/wound site.

In certain embodiments, a dry, powdered hemostatic composition comprises a first component comprising a difunctionalized polyalkylene oxide-based component of the formula:

G-LM-PEG-LM-G;

wherein:
PEG is polyethylene glycol;
each LM is a difunctional linking moiety independently selected from the group consisting of a carbonate diradical of the formula —C(O)—, a monoester diradical of the formula —(CH$_2$)$_b$—C(O)— where b is an integer from 1 to 10, a diester radical of the formula —C(O)—(CH$_2$)$_c$—C(O)— where c is an integer from 1 to 10 and where the aliphatic portion of the radical may be saturated or unsaturated, a dicarbonate diradical of the formula —C(O)—O—(CH$_2$)$_d$—O—C(O)— where d is an integer from 1 to 10, an amide containing diradical of the formula —N(H)—C(O)—(CH$_2$)$_d$—C(O)— where d is an integer from 1 to 10, an amide containing diradical of the formula —(CH$_2$)$_c$—C(O)—N(H)—(CH$_2$)$_d$— where c is an integer from 1 to 10 and d is an integer from 1 to 10, and an oligomeric diradical represented by the formulas —R—C(O)—, —R—C(O)—(CH$_2$)$_c$—C(O)—, or —R—C(O)—O—(CH$_2$)$_d$—O—C(O)—, —R—N(H)—C(O)—(CH$_2$)$_d$—C(O)—, or —R—(CH$_2$)$_c$—C(O)—N(H)—(CH$_2$)$_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl, and a second component comprising a protein that is capable of crosslinking with the first component, wherein the protein comprises a plurality of particles having a tapped particle density of greater than or equal to 0.30 g/mL, and a crosslinking initiator that initiates crosslinking of the first component with the protein or other nucleophilic polymer, wherein crosslinking occurs upon exposure to an aqueous liquid to form a hemostatic hydrogel.

According to certain embodiments, a dry, powdered hemostatic composition comprises a first component comprising a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —(CH$_2$)$_b$—C(O)— where b is an integer from 1 to 10, a diester radical of the formula —C(O)—(CH$_2$)$_c$—C(O)— where c is an integer from 1 to 10 and where the aliphatic portion of the radical may be saturated or unsaturated, a dicarbonate diradical of the formula —C(O)—O—(CH$_2$)$_d$—O—C(O)— where d is an integer from 1 to 10, an amide containing diradical of the formula —N(H)—C(O)—(CH$_2$)$_d$—C(O)— where d is an integer from 1 to 10, an amide containing diradical of the formula —(CH$_2$)$_c$—C(O)—N(H)—(CH$_2$)$_d$— where c is an integer from 1 to 10 and d is an integer from 1 to 10, and an oligomeric diradical represented by the formulas —R—C(O)—, —R—C(O)—(CH$_2$)$_c$—C(O)—, or —R—C(O)—O—(CH$_2$)$_d$—O—C(O)—, —R—N(H)—C(O)—(CH$_2$)$_d$—C(O)—, or —R—(CH$_2$)$_c$—C(O)—N(H)—(CH$_2$)$_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl; and a second component comprising a protein that is capable of crosslinking with the first component, the protein consisting essentially of particles having a particle size of greater than or equal to 50 microns and less than or equal to 500 microns, and a crosslinking initiator that initiates crosslinking of the first component with the protein, wherein crosslinking occurs upon exposure to an aqueous liquid to form a hemostatic hydrogel.

In some embodiments a dry, powdered hemostatic composition comprises a first component comprising a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —(CH$_2$)$_b$—C(O)— where b is an integer from 1 to 10, a diester radical of the formula —C(O)—(CH$_2$)$_c$—C(O)— where c is an integer from 1 to 10 and where the aliphatic portion of the radical may be saturated or unsaturated, a dicarbonate diradical of the formula —C(O)—O—(CH$_2$)$_d$—O—C(O)— where d is an integer from 1 to 10, an amide containing diradical of the formula —N(H)—C(O)—(CH$_2$)$_d$—C(O)— where d is an integer from 1 to 10, an amide containing diradical of the formula —(CH$_2$)$_c$—C(O)—N(H)—(CH$_2$)$_d$— where c is an integer from 1 to 10 and d is an integer from 1 to 10, and an oligomeric diradical represented by the formulas —R—C(O)—, —R—C(O)—(CH$_2$)$_c$—C(O)—, or —R—C(O)—O—(CH$_2$)$_d$—O—C(O)—, —R—N(H)—C(O)—(CH$_2$)$_d$—C(O)—, or —R—(CH$_2$)$_c$—C(O)—N(H)—(CH$_2$)$_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl; and a second component comprising a protein that is capable of crosslinking with the first component, wherein the protein comprises a plurality of particles having a tapped particle density of greater than or equal to 0.30 g/mL, and wherein the protein consists essentially of particles having a particle size of greater than or equal to 50 microns and less than or equal to 500 microns, and a crosslinking initiator that initiates crosslinking of the first component with the protein, wherein crosslinking occurs upon exposure to an aqueous liquid to form a hemostatic hydrogel.

In certain embodiments, a dry, powdered, crosslinking hemostatic composition comprises a first component comprising a multifunctionalized polymeric composition of the formula:

I—(—X-LM-G)$_n$ wherein:

X is a difunctional polyoxyethylene chain portion or bond;

each LM is a difunctional linking moiety independently selected from the group consisting of a carbonate diradical of the formula —C(O)—, a monoester diradical of the formula —(CH$_2$)$_b$—C(O)— where b is an integer from 1 to 10, a diester radical of the formula —C(O)—(CH$_2$)$_c$—C(O)— where c is an integer from 1 to 10 and where the aliphatic portion of the radical may be saturated or unsaturated, a dicarbonate diradical of the formula —C(O)—O—(CH$_2$)$_d$—O—C(O)— where d is an integer from 1 to 10, an amide containing diradical of the formula —N(H)—C(O)—(CH$_2$)$_d$—C(O)— where d is an integer from 1 to 10, an amide containing diradical of the formula —(CH$_2$)$_c$—C(O)—N(H)—(CH$_2$)$_d$— where c is an integer from 1 to 10 and d is an integer from 1 to 10, and an oligomeric diradical represented by the formulas —R—C(O)—, —R—C(O)—(CH$_2$)$_c$—C(O)—, —R—C(O)—O—(CH$_2$)$_d$—O—C(O)—, —R—N(H)—C(O)—(CH$_2$)$_d$—C(O)—, or —R—(CH$_2$)$_c$—C(O)—N(H)—(CH$_2$)$_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments;

each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl;

I is a multifunctional linking moiety derived from a multinucleophilic compound; and n is an integer from 2 to 10 with the proviso that when X is a difunctional polyoxyethylene chain portion and n=2, —X—I—X— is polyethylene glycol (PEG), which is a diradical fragment represented by the formula:

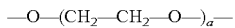

—O—(CH$_2$—CH$_2$—O—)$_a$— wherein a is an integer from 20 to 300; and a second component comprising a protein, wherein upon exposure to an aqueous liquid, crosslinking of the first component and the second component is initiated to form a hemostatic hydrogel.

According to some embodiments, a dry, powdered, crosslinking hemostatic composition comprises a first component comprising a multifunctionalized polymeric composition of the formula:

I-(LM-G)$_n$ wherein:

each LM is a difunctional linking moiety independently selected from the group consisting of a carbonate diradical of the formula —C(O)—, a monoester diradical of the formula —(CH$_2$)$_b$—C(O)— where b is an integer from 1 to 10, a diester radical of the formula —C(O)—(CH$_2$)$_c$—C(O)— where c is an integer from 1 to 10 and where the aliphatic portion of the radical may be saturated or unsaturated, a dicarbonate diradical of the formula —C(O)—O—(CH$_2$)$_d$—O—C(O)— where d is an integer from 1 to 10, an amide containing diradical of the formula —N(H)—C(O)—(CH$_2$)$_d$—C(O)— where d is an integer from 1 to 10, an amide containing diradical of the formula —(CH$_2$)$_c$—C(O)—N(H)—(CH$_2$)$_d$— where c is an integer from 1 to 10 and d is an integer from 1 to 10, and an oligomeric diradical represented by the formulas —R—C(O)—, —R—C(O)—(CH$_2$)$_c$—C(O)—, —R—C(O)—O—(CH$_2$)$_d$—O—C(O)—, —R—N(H)—C(O)—(CH$_2$)$_d$—C(O)—, or —R—(CH$_2$)$_c$—C(O)—N(H)—(CH$_2$)$_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments;

each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl;

I is a multifunctional polyoxyethylene chain portion having n functional groups able to react with a functional group of LM; and n is an integer from 2 to 10; and a second component comprising a protein, wherein upon exposure to an aqueous liquid, crosslinking of the first component and the second component is initiated to form a hemostatic hydrogel.

In some embodiments, the dry, powdered, hemostatic composition as described above or as prepared using the kit described above is suitable for use in a method of treatment by surgery. In some embodiments, the dry, powdered, hemostatic composition as described above or as prepared using the kit described above is used in a method of treatment by surgery. The method of treatment by surgery can, in some embodiments, include delivering the dry, powdered, crosslinking hemostatic composition to a bleeding/wound site (e.g., at a tissue site) and forming a hemostatic hydrogel. In some embodiments, the composition is used to stop or reduce bleeding at the bleeding/wound site.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
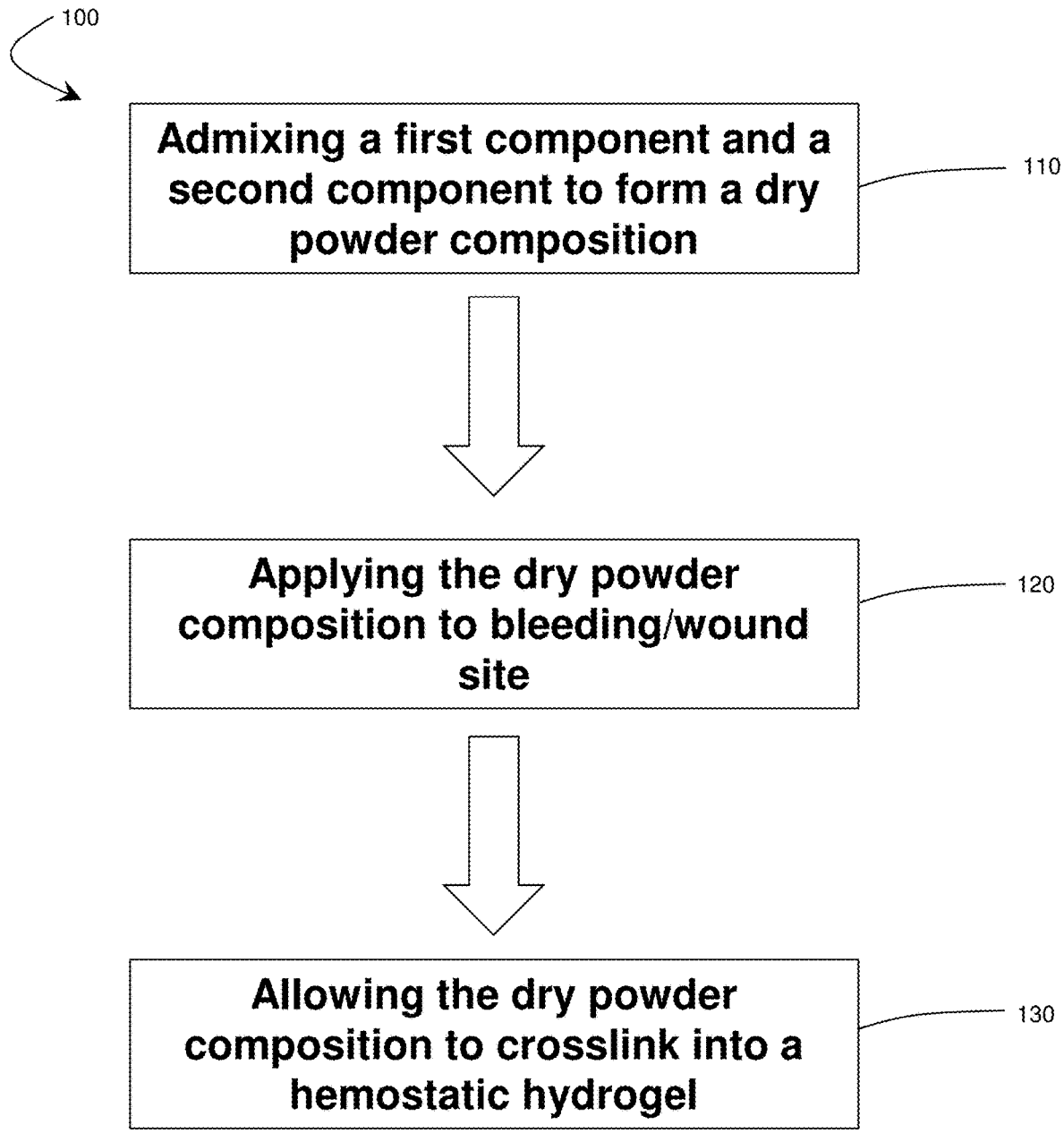
FIG. 1 shows, in accordance with certain embodiments, exemplary steps in a method for forming a hemostatic hydrogel with a dry powdered mixture.

Compositions and methods related to powdered hemostats that crosslink during and/or after application to a bleeding site are generally described. In certain embodiments, upon exposure to an aqueous liquid, a dry powdered mixture of reactive hemostat components may crosslink to form a hemostatic hydrogel. The compositions may comprise a first component comprising a multifunctionalized polymeric composition (e.g., multifunctionalized polyethylene glycol) functionalized with electrophilic reactive groups, and a second component that comprises a protein such as albumin. Exposure to an aqueous liquid may be achieved as the dry, powdered, crosslinking compositions are applied to a bleeding/wound site comprising blood and/or other bodily fluids. In addition to, or instead of, use as a hemostatic material for controlling or stopping bleeding, in certain embodiments, compositions and methods described herein may be useful for a variety of other medical applications, such as postsurgical adhesion barriers, sealants, and wound dressings.

In some instances, nucleophilic groups of the protein (e.g., amino groups from amino acid side chains and/or an N-terminus) react with the electrophilic groups of the multifunctionalized polymer to accomplish crosslinking more rapidly when unprotonated than when protonated. Some embodiments involve inclusion of separate solid base and/or basic buffers in the dry, powdered hemostatic compositions (e.g., as part of the protein-containing second component or as a separate component) to elevate the pH of the reaction mixture upon hydration and cross-linking. An alternative or additional approach involves forming unprotonated nucleophilic groups on the protein (e.g., free amine groups) in a basic state (e.g., via at least partially deprotonating the protein prior to or during formation of the second component of the dry, powdered composition), as described in more detail below. One example of such an approach is to dissolve the protein (e.g., albumin) in water and adjust the pH of the water to a basic pH, thereby at least partially deprotonating the protein, and then removing the water to provide a pH-adjusted protein in dry powder form.

As used herein, the term "crosslink" refers to a chemical reaction between two or more similar or dissimilar polymers, copolymers, oligomers, and/or macromers that links the two or more similar or dissimilar polymers, copolymers, oligomers, or macromers via formation of at least one covalent bond and/or ionic bond, or a chain extension between one or more polymers, copolymers, oligomers, and/or macromers to provide a longer chain of the one or more polymers, copolymers, oligomers, and/or macromers via formation of at least one covalent bond and/or ionic bond.

In certain embodiments, a multi-component (e.g., two component, three component, etc.) composition may be provided and used. In some embodiments, a first component comprises a multifunctionalized (e.g., difunctionalized) polyalkylene oxide-based component, and a second component comprises one or both of a protein (e.g., albumin) that is capable of crosslinking with the first component and a crosslinking initiator that initiates crosslinking of the first component with the protein. In certain embodiments related to the multi-component composition, crosslinking to form a hemostatic hydrogel is initiated upon exposure of the composition to an aqueous liquid. For example, upon exposure of the first component and the second component of the dry, powdered hemostatic composition to blood upon application of the dry powdered composition to bleeding tissue (e.g., at a bleeding/wound site), crosslinking to form a hemostatic hydrogel may be initiated. In some cases, the structural properties (e.g., particle size and/or particle density) of certain components of the dry powder composition may affect the time required for the dry powder composition to crosslink and form a hemostatic hydrogel or may affect the degree of crosslinking or both.

In some embodiments, a two-component reactive dry powder composition (e.g., dry powder mixture) may be provided and used. In certain embodiments, the first component comprises a first dry powder comprising a multifunctionalized (e.g., difunctionalized) polyalkylene oxide-based component, and a second component comprises a second dry powder (e.g., a protein such as albumin) that is capable of crosslinking with the first dry powder. Upon exposure to an aqueous liquid, the second dry powder may crosslink with the first dry powder, or an initiator may be used in certain cases to initiate crosslinking between the two different reactive powdered components, resulting in a crosslinked hemostatic hydrogel that is capable of stopping and/or reducing bleeding at the bleeding/wound site. Hemostatic precursors comprising crosslinking multifunctionalized (e.g., difunctionalized) polyalkylene oxide-based components (such as, for example, polyethylene glycol (PEG)) and/or protein (e.g. albumin) may help alleviate issues related to the need for manual compression in certain existing hemostatic technologies by forming a hydrogel with tissue adherence, in certain embodiments.

According to some embodiments, a dry, powdered, hemostatic composition comprises a first component and a second component. In certain embodiments, the first component is in the form of a first powder (e.g., a first dry powder), and the second component is in the form of a second powder (e.g., a second dry powder). In certain embodiments, a two part crosslinking dry powder hemostatic formulation is provided. Further details regarding the form of the dry, powdered, hemostatic composition are discussed below.

In certain embodiments, the first component (e.g., first dry powder) comprises a multifunctionalized polymeric composition. In some embodiments, for example, the multifunctionalized polymeric composition may be a difunctionalized polymeric composition, a tetrafunctionalized polymeric composition, a hexafunctionalized polymeric composition, an octafunctionalized polymeric composition, or the like. Other degrees of functionality are also possible (e.g., trifunctionalized, pentafunctionalized, etc.). The multifunctionalized polymer composition may comprise multiple electrophilic groups capable of reacting with nucleophiles such as amino groups (e.g., in aqueous solutions).

According to certain embodiments, the first component (e.g., first dry powder) comprises a difunctionalized polymeric composition. In some embodiments, for example, the first component (e.g., first dry powder) comprises a difunctionalized polyalkylene oxide-based component. In certain aspects, the difunctionalized polyalkylene oxide-based component is of the formula:

G-LM-PEG-LM-G;

wherein:
PEG is polyethylene glycol;
each LM is a difunctional linking moiety independently selected from the group consisting of a carbonate diradical of the formula —C(O)—, a monoester diradical of the formula —(CH$_2$)$_b$—C(O)— where b is an integer from 1 to 10, a diester radical of the formula —C(O)—(CH$_2$)$_c$—C(O)— where c is an integer from 1 to 10 and where the aliphatic portion of the radical may be saturated or unsaturated, a dicarbonate diradical of the formula —C(O)—O—(CH$_2$)$_d$—O—C(O)— where d is an integer from 1 to 10, an amide containing diradical of the formula —N(H)—C(O)—(CH$_2$)$_d$—C(O)— where d is an integer from 1 to 10, an amide containing diradical of the formula —(CH$_2$)$_c$—C(O)—N(H)—(CH$_2$)$_d$— where c is an integer from 1 to 10 and d is an integer from 1 to 10, and an oligomeric diradical represented by the formulas —R—C(O)—, —R—C(O)—(CH$_2$)$_c$—C(O)—, —R—C(O)—O—(CH$_2$)$_d$—O—C(O)—, —R—N(H)—C(O)—(CH$_2$)$_d$—C(O)—, or —R—(CH$_2$)$_c$—C(O)—N(H)—(CH$_2$)$_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and
each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl.

According to certain embodiments, the first component (e.g., first dry powder) comprises a difunctionalized polyalkylene oxide-based component of the formula:

G-LM-PEG-LM-G;

wherein:
PEG is polyethylene glycol;
each LM is the same and is a difunctional linking moiety represented by the formulas —C(O)—, (CH$_2$)$_b$—C(O)— where b is an integer from 1 to 5, —C(O)—(CH$_2$)$_c$—C(O)— where c is an integer from 2 to 10 and where the aliphatic portion of the radical may be saturated or unsaturated, —C(O)—O—(CH$_2$)$_d$—O—C(O)— where d is an integer from 2 to 10, and an oligomeric diradical represented by the formulas —R—C(O)—, —R—C(O)—(CH$_2$)$_c$—C(O)—, or —R—C(O)—O—(CH$_2$)$_d$—O—C(O)— where c is an integer from 2 to 10, d is an integer from 2 to 10, and R is a polymer or copolymer having 1 to 10 monomeric lactide, glycolide, trimethylene carbonate, caprolactone or p-dioxanone fragments; and
each G is the same and is a leaving group selected from the group of N-oxysuccinimidyl, N-oxysulfosuccinimidyl, N-oxymaleimidyl, N-oxyphthalimidyl, nitrophenoxyl, N-oxyimidazolyl, and tresyl.

According to some embodiments, the first component (e.g., first dry powder) comprises any of a variety of suitable difunctionalized polymeric compositions. In some aspects, the first component (e.g., first dry powder) may comprise a difunctionalized polyalkylene oxide-based component of the formula G-LM-PEG-LM-G. For example, in certain embodiments, the first component (e.g., first dry powder) may comprise:

PEG disuccinimidyl succinate (PEG(SS)2), a 2-arm crosslinker of the form:

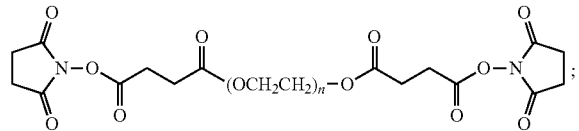

PEG disuccinimidyl valerate (PEG(SVA)2), a 2-arm crosslinking of the form:

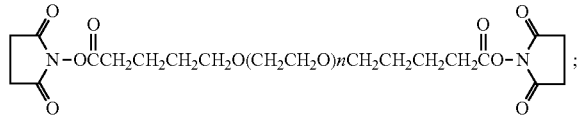

and/or
PEG disuccinimidyl hexanoate (PEG(SHA)2), a 2-arm crosslinker of the form:

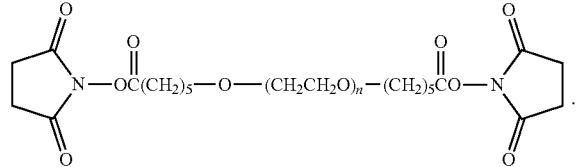

In some embodiments, the first component (e.g., first dry powder) comprises a multifunctionalized polymeric composition of the formula:

I—(—X-LM-G)$_n$ wherein:
X is a polyoxyethylene chain portion or a bond;
each LM is a difunctional linking moiety independently selected from the group consisting of a carbonate diradical of the formula —C(O)—, a monoester diradical of the formula —(CH$_2$)$_b$—C(O)— where b is an integer from 1 to 10, a diester radical of the formula —C(O)—(CH$_2$)$_c$—C(O)— where c is an integer from 1 to 10 and where the aliphatic portion of the radical may be saturated or unsaturated, a dicarbonate diradical of the formula —C(O)—O—(CH$_2$)$_d$—O—C(O)— where d is an integer from 1 to 10, an amide containing diradical of the formula —N(H)—C(O)—(CH$_2$)$_d$—C(O)— where d is an integer from 1 to 10, an amide containing diradical of the formula —(CH$_2$)$_c$—C(O)—N(H)—(CH$_2$)$_d$— where c is an integer from 1 to 10 and d is an integer from 1 to 10, and an oligomeric diradical represented by the formulas —R—C(O)—, —R—C(O)—(CH$_2$)$_c$—C(O)—, —R—C(O)—O—(CH$_2$)$_d$—O—C(O)—, —R—N(H)—C(O)—(CH$_2$)$_d$—C(O)—, or —R—(CH$_2$)$_c$—C(O)—N(H)—(CH$_2$)$_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments;
each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl;

I is a multifunctional linking moiety derived from a multinucleophilic compound; and n is an integer from 2 to 10;

with the proviso that when X is a difunctional polyoxyethylene chain portion and n=2, —X—I—X— is polyethylene glycol (PEG), which is a diradical fragment represented by the formula:

—O—(CH$_2$—CH$_2$—O—)$_a$— wherein a is an integer from 20 to 300.

While in some embodiments, a multifunctionalized polymer of the formula I—(—X-LM-G)$_n$ as described above is a difunctionalized polymer such as PEG(SS)2 (e.g., where X is a bond and n is 2 and I is a difunctional polyethylene glycol (PEG)), in some embodiments the first component comprises a multifunctionalized polymer with a higher (than two) degree of functionality (e.g., n is 3, 4, 5, 6, 7, or 8).

In some embodiments, the first component (e.g., first dry powder) comprises a multifunctionalized polymeric composition of the formula:

I—(—X-LM-G)$_n$ wherein:
X is a polyoxyethylene chain portion or a bond;
each LM is the same and is a difunctional linking moiety represented by the formulas —C(O)—, —(CH$_2$)$_b$—C(O)— where b is an integer from 1 to 5, —C(O)—(CH$_2$)$_c$—C(O)— where c is an integer from 2 to 10 and where the aliphatic portion of the radical may be saturated or unsaturated, —C(O)—O—(CH$_2$)$_d$—O—C(O)— where d is an integer from 2 to 10, or an oligomeric diradical represented by the formulas —R—C(O)—, —R—C(O)—(CH$_2$)$_c$—C(O)—, or —R—C(O)—O—(CH$_2$)$_d$—O—C(O)—where c is an integer from 1 to 10, d is an integer from 1 to 10, and R is a polymer or copolymer having 1 to 10 monomeric lactide, glycolide, trimethylene carbonate, caprolactone or p-dioxanone fragments;
each G is the same is a leaving group selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl;
I is a multifunctional linking moiety derived from a multinucleophilic compound; and
n is an integer from 2 to 10;
with the proviso that when X is a difunctional polyoxyethylene chain portion and n=2, —X—I—X— is polyethylene glycol (PEG), which is a diradical fragment represented by the formula:

—O—(CH$_2$—CH$_2$—O—)$_a$— wherein a is an integer from 20 to 300. In some such embodiments, the multifunctionalized polymeric composition has a higher (than two) degree of functionalization.

According to some embodiments, the first component (e.g., first dry powder) comprises a multifunctionalized polymeric composition of the formula:

I—(—X-LM-G)$_n$ wherein:
when X is a bond, I is a multi-arm PEG in which the number of arms is n.

In certain embodiments, X in the formula I—(—X-LM-G)$_n$ is the difunctional polyethylene oxide polyethylene glycol (PEG), which is represented by the formula:

—O—(CH$_2$—CH$_2$—O—)$_a$— wherein:
a is an integer from 20 to 300.

In some embodiments (e.g., where X is a bond), the first component (e.g., first dry powder) comprises a multifunctionalized polymeric composition of the formula:

I-(LM-G)$_n$ wherein:
each LM is a difunctional linking moiety independently selected from the group consisting of a carbonate diradical of the formula —C(O)—, a monoester diradical of the formula —(CH$_2$)$_b$—C(O)— where b is an integer from 1 to 10, a diester radical of the formula —C(O)—(CH$_2$)$_c$—C(O)— where c is an integer from 1 to 10 and where the aliphatic portion of the radical may be saturated or unsaturated, a dicarbonate diradical of the formula —C(O)—O—(CH$_2$)$_d$—O—C(O)— where d is an integer from 1 to 10, —N(H)—C(O)—(CH$_2$)$_d$—C(O)— where d is an integer from 1 to 10, (CH$_2$)$_c$—C(O)—N(H)—(CH$_2$)$_d$— where c is an integer from 1 to 10 and d is an integer from 1 to 10, and an oligomeric diradical represented by the formulas —R—C(O)—, —R—C(O)—(CH$_2$)$_c$—C(O)—, —R—C(O)—O—(CH$_2$)$_d$—O—C(O)—, —R—N(H)—C(O)—(CH$_2$)$_d$—C(O)—, or —R—(CH$_2$)$_c$—C(O)—N(H)—(CH$_2$)$_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments;
each G is a leaving group independently selected from the group of N-oxysuccinimidyl, N-oxysulfosuccinimidyl, N-oxymaleimidyl, N-oxyphthalimidyl, nitrophenoxyl, N-oxyimidazolyl, and tresyl;
I is a multifunctional polyoxyethylene chain portion having n functional groups able to react with a functional group of LM; and
n is an integer from 2 to 10. In some such embodiments, the multifunctionalized polymeric composition has a higher (than two) degree of functionalization, though in some embodiments the multifunctionalized polymeric composition is difunctionalized (e.g., n is 2). It should be understood that when it is stated that the multifunctionalized polyoxyethylene chain portion has n functional groups able to react with a functional group of LM, such characterization relates to the nature of the portions of the molecule in their unassembled/disassembled state for the purpose of explaining to the reader the nature of the subcomponents and their mutual reactivity. Of course, as would be apparent to those skilled in the art, with respect to the compositions described by the chemical formulas described herein, the reaction between the indicated functional group and LM is understood to have occurred in the polymer represented by the formula I-(LM-G)$_n$, (i.e. the formula describes the nature of the formed bonds based on the reactivity of their precursor components rather than the formula representing a set of reactants in an unreacted state). For example, in considering PEG(SS)2 as a species of I-(LM-G)$_n$, I is a polyethylene glycol chain portion and LM is succinate diradical. The polyethylene glycol has a functional group (an oxide oxygen) bound to a carbonyl carbon of the succinate diradical (—C(O)—(CH$_2$)$_2$—C(O)—). In this way, the polyethylene glycol chain portion has a functional group (an oxyl radical) able to react with a functional group (a carbonyl carbon radical) of the succinate diradical, as evidenced by the fact the two functional groups are bound in PEG(SS)2.

According to some embodiments, the first component (e.g., first dry powder) comprises a multifunctionalized polymeric composition of the formula:

I-(LM-G)$_n$ wherein:

each LM is the same and is a difunctional linking moiety represented by the formulas —C(O)—, (CH$_2$)$_b$—C(O)— where b is an integer from 1 to 5, —C(O)—(CH$_2$)$_c$—C(O)— where c is an integer from 2 to 10 and where the aliphatic portion of the radical may be saturated or unsaturated, —C(O)—O—(CH$_2$)$_d$—O—C(O)— where d is an integer from 2 to 10, or an oligomeric diradical represented by the formulas —R—C(O)—, —R—C(O)—(CH$_2$)$_c$—C(O)—, or —R—C(O)—O—(CH$_2$)$_d$—O—C(O)— where c is an integer from 2 to 10, d is an integer from 2 to 10, and R is a polymer or copolymer having 1 to 10 monomeric lactide, glycolide, trimethylene carbonate, caprolactone or p-dioxanone fragments;

each G is the same and is a leaving group selected from the group of N-oxysuccinimidyl, N-oxysulfosuccinimidyl, N-oxymaleimidyl, N-oxyphthalimidyl, nitrophenoxyl, N-oxyimidazolyl and tresyl;

I is a multifunctional polyoxyethylene chain portion having n functional groups able to react with a functional group of LM; and n is an integer from 2 to 10. In some such embodiments, the multifunctionalized polymeric composition has a higher (than two) degree of functionalization.

In some embodiments, the first component (e.g., first dry powder) comprises a multifunctionalized polymeric composition of the formula G-LM-PEG-LM-G wherein:

each LM is a difunctional linking moiety independently selected from the group consisting of a carbonate diradical of the formula —C(O)—, a monoester diradical of the formula —(CH$_2$)$_b$—C(O)— where b is an integer from 1 to 10, a diester radical of the formula —C(O)—(CH$_2$)$_c$—C(O)— where c is an integer from 1 to 10 and where the aliphatic portion of the radical may be saturated or unsaturated, a dicarbonate diradical of the formula —C(O)—O—(CH$_2$)$_d$—O—C(O)— where d is an integer from 1 to 10, an amide containing diradical of the formula —N(H)—C(O)—(CH$_2$)$_d$—C(O)— where d is an integer from 1 to 10, an amide containing diradical of the formula —(CH$_2$)$_c$—C(O)—N(H)—(CH$_2$)$_d$— where c is an integer from 1 to 10 and d is an integer from 1 to 10, and an oligomeric diradical represented by the formulas —R—C(O)—, —R—C(O)—(CH$_2$)$_c$—C(O)—, —R—C(O)—O—(CH$_2$)$_d$—O—C(O)—, —R—N(H)—C(O)—(CH$_2$)$_d$—C(O)—, or —R—(CH$_2$)$_c$—C(O)—N(H)—(CH$_2$)$_d$— where c is an integer from 2 to 10, d is an integer from 2 to 10, and R is a polymer or copolymer having 1 to 10 monomeric lactide, glycolide, trimethylene carbonate, caprolactone or p-dioxanone fragments;

each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl.

According to some embodiments, the first component (e.g., first dry powder) comprises any of a variety of suitable multifunctionalized polymeric compositions with a higher (than two) degree of functionality. For example, in certain embodiments, the first component (e.g., first dry powder) may comprise:

PEG tetrasuccinimidyl glutarate (PEG(SG)4), a 4 arm crosslinker of the form:

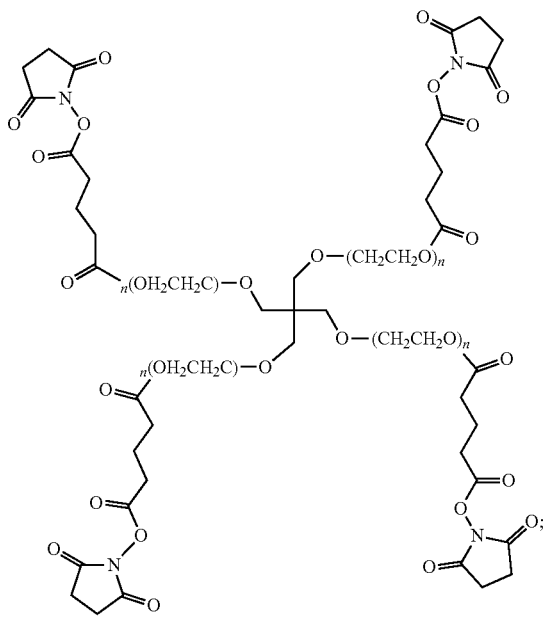

and/or

PEG tetrasuccinimidyl lactylglutarate (PEG(SG)42LA), a 4 arm crosslinker of the form:

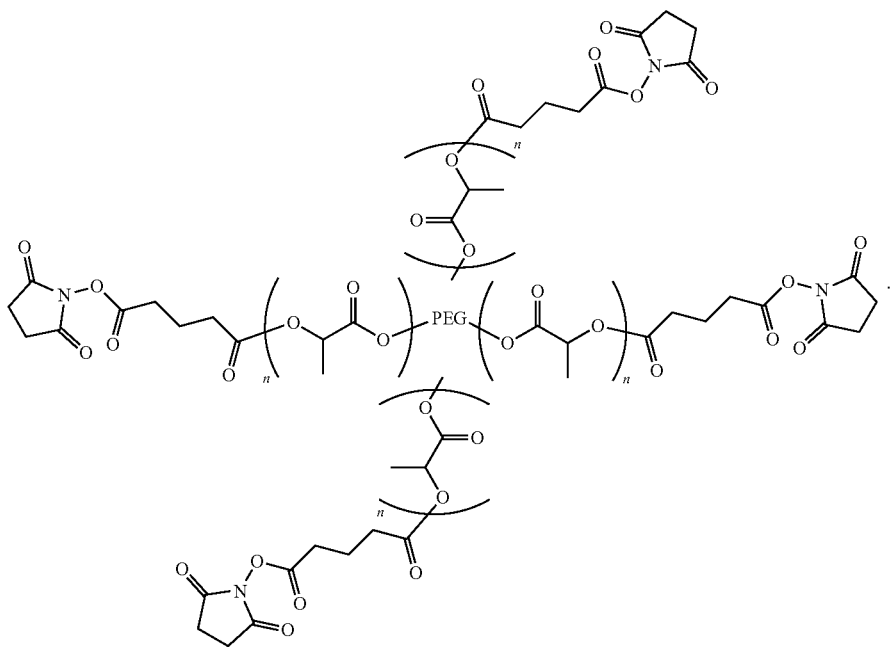

In some embodiments, in any of the chemical structures above (e.g., PEG(SS)2, PEG(SVA)2, PEG(SHA)2, PEG(SG)4, PEG(SG)42LA), each n is independently an integer from 10 to 500. In some such embodiments, each n may independently be an integer from 50 to 200.

Other multifunctionalized polymeric compositions are also possible. For example, in some embodiments the first component (e.g., first dry powder) comprises a di- or higher order multifunctionalized PEG based on any of the following PEG-NHS esters:

| PEG NHS Ester | Ester (symbol) |
| --- | --- |
| PEG-CH$_2$CH$_2$CH$_2$CH$_2$—CO$_2$—NHS | Succinimidyl Valerate (SVA) |
| PEG-O—CO$_2$—NHS | Succinimidyl Carbonate (SC) |
| PEG-O$_2$C—CH$_2$CH$_2$CH$_2$—CO$_2$—NHS | Succinimidyl Glutarate (SG) |
| PEG-O$_2$C—CH$_2$CH$_2$—CO$_2$—NHS | Succinimidyl Succinate (SS) |
| PEG-O—CH$_2$—CO$_2$—NHS | Succinimidyl Carboxymethylated (SCM) |
| PEG-O—CH$_2$CH$_2$CH$_2$—CO$_2$—NHS | Succinimidyl Butanoate (SBA) |
| PEG-NHCO—CH$_2$CH$_2$—CO$_2$—NHS | Succinimidyl Succinamide (SSA) |
| PEG-O—CH$_2$CH$_2$—CO$_2$—NHS | Succinimidyl Propionate (SPA) |
| PEG2-O$_2$CHN—CH(R)$^2$ × CO$_2$, NHS | mPEG2 × NHS |

In certain embodiments, the first component (e.g., first dry powder) comprises a combination of polymeric compositions. For example, in certain embodiments, the first component may comprise any suitable combination of a difunctionalized polymeric composition, a tetrafunctionalized polymeric composition, a hexafunctionalized polymeric composition, and/or an octafunctionalized polymeric composition. In some non-limiting embodiments, the first component comprises a difunctionalized polymeric composition and a tetrafunctionalized polymeric composition.

According to certain embodiments with a first component (e.g., first dry powder) comprising a difunctionalized polymeric composition of the formula G-LM-PEG-LM-G and/or a multifunctionalized polymeric composition of the formula I—(—X-LM-G)$_n$, or I-(LM-G)$_n$, the polymeric composition may have any of a variety of suitable weight average molecular weights. For example, in certain embodiments, multifunctionalized polymer composition (e.g., difunctionalized or higher) of the first component (e.g., first dry powder) has a weight average molecular weight of greater than or equal to 1 kDa, greater than or equal to 5 kDa, greater than or equal to 10 kDa, greater than or equal to 15 kDa, greater than or equal to 20 kDa, or greater than or equal to 25 kDa. In certain embodiments, the polymeric composition is a macromer having a weight average molecular weight of less than or equal to 30 kDa, less than or equal to 25 kDa, less than or equal to 20 kDa, less than or equal to 15 kDa, less than or equal to 10 kDa, or less than or equal to 5 kDa. Combinations of the above recited ranges are also possible (e.g., the first component comprises a multifunctionalized polymeric composition with a weight average molecular weight of greater than or equal to 1 kDa and less than or equal to 30 kDa, or greater than or equal to 10 kDa and less than or equal to 15 kDa, and the like). In some embodiments, the weight average molecular weight of the first component (e.g., a first dry powder) comprising a multifunctionalized polymeric composition is determined using size exclusion chromatography-multi-angle laser light scattering (SEC-MALLS). It should be understood that the weight average molecular weight can depend on, for example, the number of monomers in each polymeric component of a multifunctionalized polymeric composition. For example, in some embodiments, when the multifunctionalized polymeric composition is PEG(SS)2, the degree of ethoxylation in the PEG (and the value for n in the formula shown for PEG(SS)2 above) is such that the multifunctionalized polymeric composition has a weight average molecular weight in any of the ranges provided above. In certain embodiments, for the chemical structure of the 2-arm PEG disuccinimidyl succinate (PEG(SS)2) shown above, n is in the range of 10 to 500, or 50 to 200.

According to certain embodiments, multifunctionalized polymeric compositions describable by the formula G-LM-PEG-LM-G, I—(—X-LM-G)$_n$, and/or I-(LM-G)$_n$, such as but not limited to the examples noted above, may be prepared by any of a variety suitable synthetic methods known to those skilled in the art. For example, see, U.S. Pat. No. 6,576,263, issued on Jun. 10, 2003 to Truong et al.; U.S. Reissued Pat. No. RE38,827, issued on Oct. 11, 2005 to Barrows et al.; and U.S. Reissued Pat. No. RE38,158, issued on Jun. 24, 2003 to Barrows et al.; each of which is incorporated herein by reference in its entirety for all purposes.

For example, the multifunctionalized polymeric compositions describable by the formula G-LM-PEG-LM-G, I—(—X-LM-G)$_n$, and/or I-(LM-G)$_n$ may be prepared using known processes, procedures or synthetic methods such as the procedures reported in U.S. Pat. No. 4,101,380, issued on Jul. 18, 1978 to Rubinstein, or U.S. Pat. No. 4,839,345, issued on Jun. 13, 1989 to Doi et al., the procedure reported in International Application Publication No. WO/1990/013540 by Zalipsky, published on Nov. 15, 1990 from International Application No. PCT/US90/02133, filed Apr. 19, 1990, or the procedure reported by Abuchowski et al., *Cancer Biochem. Biophys.*, 7:175-186 (1984), each of which are incorporated herein by reference in their entirety. Briefly, a polyalkylene oxide-based component (e.g., polyethylene glycol discussed below as exemplary) and a suitable acid anhydride are dissolved in a suitable polar organic solvent in the presence of base and refluxed for a period of time sufficient to form a polyethylene glycol diester diacid. The diester diacid is then reacted with a leaving group such as an N-hydroxy imide compound in a suitable polar organic solvent in the presence of dicyclohexylcarbodiimide or other condensing agents and stirred at room temperature to form the desired difunctional crosslinking agent.

All or some of the multifunctionalized polymeric compositions describable by the formula G-LM-PEG-LM-G, I—(—X-LM-G)$_n$, and/or I-(LM-G)$_n$ may be purchased from commercial sources, including, but not limited to, NOF America Corporation and/or Laysan Bio, Inc. The multifunctionalized polymeric compositions may also be readily synthetized by persons of ordinary skill in the chemical synthesis art in view the teaching and exemplary methods described herein for exemplary compositions, published literature, and the level of ordinary skill and knowledge of the skilled artisan.

In certain non-limiting embodiments, PEG(SS)2 can be synthesized by obtaining a linear PEG with an average weight average molecular weight of 3,350 Da, representing 75.7 oxyethylene repeat units. The linear PEG can be obtained, for example, from Dow Chemical Company. The linear PEG may be converted to PEG(SS)2 via a two-step synthesis, in some cases. For instance, the first step may comprise reacting the linear PEG with succinic anhydride to produce PEG(disuccinate), or PEG(SS). The second step may comprise reacting PEG(SS) with N-hydroxysuccinimide to produce PEG(SS)2, resulting in a white solid and a two arm crosslinker that possess two succinimidyl groups per molecule.

Alternatively, in another non-limiting embodiment, PEG(SG)4 is derived from a PEG with a weight average molecular weight of, for example, between 2,000 Da and 10,000 Da, or greater, and utilizes glutaric acid anhydride in place of succinic anhydride to produce the intermediate, followed by the same N-hydroxysuccinimide reaction in the subsequent step. Instead of two reactive end groups, PEG(SG)4 possesses four reactive end groups. The first step of the synthesis involves the addition of the anhydride (e.g., glutaric anhydride) to the linear PEG (e.g., PEG 10,000) to incorporate the carboxyl end groups. The product is then reacted with N-hydroxysuccinimide reagent in the second step to add the succinimidyl reactive end groups.

In yet another non-limiting embodiment, synthesis of PEG(SG)42LA proceeds similarly to PEG(SG4) but includes an additional step of reaction with lactic acid to incorporate lactide groups. The purpose of incorporating lactide groups, in certain embodiments, is to provide a hydrolytically susceptible linkage in the final product thereby facilitating faster resorption. In some embodiments, the lactide groups are added prior to the step of reacting with glutaric anhydride and utilizes cyclic lactide in place of lactic acid. Because lactide is a dimer of lactic acid, the number of lactic acid groups in the chain will be an even number and will yield a distribution of molecular weights. For example, for a PEG(SG)42LA with a weight average molecular weight of 11,500 Da, there are roughly 2.5 lactide groups/arm or 10 lactide groups/molecule (e.g., 4 arms). The first synthetic step is the addition of the lactide groups to each end of the PEG. The second synthetic step is the addition of glutaric anhydride, followed by the addition of N-hydroxysuccinimide.

In certain embodiments, multifunctionalized polymeric compositions of the formula G-LM-PEG-LM-G, I—(—X-LM-G)$_n$, and/or I-(LM-G)$_n$ comprise a leaving group G (e.g., N-oxysuccinimidyl, N-oxysulfosuccinimidyl, N-oxymaleimidyl, N-oxyphthalimidyl, nitrophenoxyl, N-oxyimidazolyl, and tresyl) capable of reacting (e.g., being displaced by) with a nucleophilic group, for example an amine group on a protein. For example, when G is N-oxysuccinimidyl, G-LM-PEG-LM-G comprises an NHS ester electrophilic group comprising an N-oxy-succinimidyl leaving group. According to certain embodiments, the leaving group G (e.g., the N-oxysuccinimidyl group of the NHS ester in PEG(SS)2) reacts with an amine group of the protein to produce a crosslinked composition that forms an amide bond upon release of the leaving group G. Such reactivity is further described in U.S. Pat. No. 6,458,147, issued on Oct. 1, 2002 to Cruise et al., which is incorporated herein by reference in its entirety.

According to some embodiments, a dry powder hemostatic formulation comprises a second component (e.g., second dry powder) that crosslinks with the first component (e.g., first dry powder, such as PEG(SS)2). In certain embodiments, the second component is in the form of a second dry powder.

In certain embodiments, the second component comprises a protein. In certain cases, the protein comprises any of a variety of suitable albumins. For example, in some embodiments, the protein comprises serum albumin. The serum albumin may be, in some cases, human serum albumin (HSA) derived from donor blood. In some instances, the serum albumin is recombinant human albumin (rHA) derived from yeast. In some instances, the serum albumin is animal sourced albumin (e.g., bovine serum albumin (BSA)). In certain non-limiting embodiments, for example, the protein may be Cohn analog culture grade BSA obtained from Proliant Biologicals. In some aspects, the recombinant human albumin may be Cellastim™ recombinant human albumin, Healthgen™ recombinant human albumin, or Optibumin™ recombinant human albumin.

According to some embodiments, the protein comprises collagen or gelatin.

In some embodiments, the above nucleophilic electrophilic crosslinking reactions are pH sensitive and are inhibited at acidic pH while being initiated at neutral or basic pH values. In some such cases, the dry, powdered hemostatic composition comprises an initiator (e.g., a crosslinking initiator). In some instances, the crosslinking initiator comprises a base or a basic buffer that may be used in combination with the reactive materials to initiate or facilitate crosslinking. The base or basic buffer may be provided in any of a variety of forms. In some embodiments, the crosslinking initiator is part of the second component of the dry, powdered hemostatic composition. For example, the base or basic buffer may be present as a separate solid in the second component (e.g., as separate particles of a dry powder and/or as a separate region of a composite particle). However, in some embodiments, the crosslinking initiator is provided in a different manner, such as a third component of the dry, powdered hemostatic composition (e.g., a third dry powder). In some embodiments, a crosslinking initiator is a portion of the protein, such as a chemically-modified portion of the protein (e.g., a deprotonated amino acid side chain). According to certain embodiments, the crosslinking initiator comprising a base and/or basic buffer facilitates the crosslinking reaction between the electrophilic component of any of the compositions described above upon dissociation of leaving group G with the amine group of a protein.

As mentioned above, in some embodiments the dry, powdered hemostatic composition comprises a crosslinking initiator, and the crosslinking initiator is a base, base-treated portion of a protein, and/or basic buffer. The conjugate acid of the base and/or basic buffer may have a $pK_a$ suitable for initiating the nucleophile/electrophile reaction between the nucleophilic groups (e.g., amino groups) of the protein and the electrophilic groups of the multifunctionalized polymeric composition (e.g., PEG(SS)2) as part of a crosslinking reaction. For example, when a separate base and/or basic buffer is used or present as the initiator, it may have a $pK_a$ sufficiently high to at least partially deprotonate amino acid side chains of the protein (e.g., lysines of a serum albumin) upon exposure to an aqueous liquid (e.g., saline solution, blood at a bleeding site, etc.). In some, but not necessarily all embodiments, the base and/or basic buffer is non-nucleophilic. In some embodiments, the base and/or basic buffer does not include amine functionalities. Those of ordinary skill in the art would be familiar with non-nucleophilic bases or basic buffers. A lack of amine functionalities may advantageously avoid nucleophilic reactions between the base and/or basic buffer and the electrophilic groups of the multifunctionalized polymer (PEG(SS)2) that might compete with the desired crosslinking reactions with the protein.

In some embodiments, the base and/or basic buffer is a salt comprising a cation and an anion. The salt may be, for example, an inorganic salt. In some such embodiments, the cation is an alkali metal cation (e.g., a lithium ion, a sodium ion, and potassium ion, etc.). In some embodiments, the basic anion is an oxyanion. The oxyanion may be, for example, bicarbonate. In some embodiments, the oxyanion is a phosphate anion (e.g., dibasic phosphate, $HPO_4^{2-}$). In some embodiments, the oxyanion is a borate anion. In some embodiments, the base and/or basic buffer comprises a cation and hydroxide ($OH^-$). Non-limiting examples of potentially suitable bases and/or basic buffers include sodium bicarbonate, sodium phosphate (e.g., sodium phosphate dibasic, $Na_2HPO_4$), and sodium hydroxide (NaOH).

In some embodiments, the base and/or basic buffer of the crosslinking initiator is non-gas-forming in aqueous solutions. In this context, a gas-forming base and/or basic buffer is one that, upon reaction with one or more protons in water, undergoes a gas evolution reaction under standard conditions. For example, reaction of bicarbonate with a proton (e.g., in the form of a hydronium ion $H_3O^+$) can generate carbon dioxide (a gaseous species) and water. Therefore, bicarbonate salts such as sodium bicarbonate are considered to be gas-forming. In contrast, reaction of a non-gas-forming base and/or basic buffer with a proton in water does not form a gaseous species. For example, reaction of dibasic phosphate ($HPO_4^{2-}$) with one or more protons (e.g., in the form of a hydronium ion, $H_3O^+$) generates monobasic ($H_2PO_4^-$) or phosphoric acid ($H_3PO_4$), neither of which are gaseous species under standard conditions. Therefore, phosphate salts such as sodium phosphate dibasic are considered non-gas-forming. Other examples of non-gas-forming bases and/or basic buffers include, but are not limited to sodium borate and sodium hydroxide. Additional examples of non-gas-forming bases and/or basic buffers include embodiments where the base is a borate ($BO_3^-$) or metaborate ($BO_2^-$) salt. For example, in some embodiments, the base is sodium borate ($NaBO_3$), potassium borate ($KBO_3$), or a combination thereof. In some embodiments, the base is a tetraborate salt (e.g., sodium tetraborate, $Na_2B_4O_7$, potassium tetraborate, $K_2B_4O_7$). It has been observed in the context of this disclosure that gas evolution reactions by gas-forming bases and/or basic buffers such as sodium bicarbonate can generate gas bubbles during crosslinking reactions under some conditions. Formation of gas bubbles may disrupt the integrity of resulting hemostatic hydrogels and/or adversely affect adherence of such a hemostatic hydrogel with bleeding tissue. Inclusion of non-gas-forming bases and/or basic buffers may mitigate or eliminate bubble formation and resulting adverse effects on hemostasis. In some embodiments, the dry, powdered hemostatic composition is free from any powdered gas-forming basic salt and/or basic buffer. In some embodiments, the dry, powdered hemostatic composition is free from any powdered basic salt and/or basic buffer comprising a carbonate anion or bicarbonate anion.

According to certain embodiments, the reaction between the electrophilic group comprising leaving group G and the amine group of the protein occurs at pH of greater than or equal to 7, and the crosslinking reaction in situ is made to occur (e.g., without addition of a separate solid base or basic buffer or through addition of a base or basic buffer to one or both of the reactive components) at a pH of greater than or equal to 7, a pH of greater than or equal to 7.4, a pH of greater than or equal to 8, a pH of greater than or equal to 9, a pH of greater than or equal to 10.

It has been realized in the context of the present disclosure that it is possible to provide a dry, powdered hemostatic composition in which the protein (e.g., serum albumin) of the second component can react with the multifunctionalized polymer composition comprising multiple electrophilic groups of the first component without requiring a separate base and/or basic buffer (e.g., included in the dry, powdered composition or added as a separate dry powder). The dry, powdered composition may be afforded, for example, by preparing the protein as a dry powder in such a way that upon exposure to an aqueous liquid (e.g., blood at bleeding tissue) even in the absence of a separate powdered base and/or basic buffer, some or all of the amine groups of the protein act as the initiator in that they have been rendered to be free amines in sufficient quantity to initiate crosslinking to form the hemostatic hydrogel. This surprising result may allow for formulations of the dry, powdered, hemostatic composition with little or no need for a separate powdered basic salt of buffer salt to act as the initiator. In some embodiments, the dry, powdered hemostatic composition is free from any powdered basic salt or buffer salt. It should be understood that a dry, powdered hemostatic composition that is free from any powdered basic salt or buffer salt may still comprise a crosslinking initiator as the term is generally understood. For example, as described below, a protein in such a formulation may comprise unprotonated amino acid side chains, which can lend basicity to the protein capable of initiating crosslinking (e.g., by elevating a pH of a resulting aqueous liquid and providing free amino groups for nucleophile/electrophile reactions). Such formulations may provide one way to avoid use of gas-forming bases and/or basic buffers such as sodium bicarbonate (thereby mitigating adverse effects from gassing during crosslinking). Such formulations may also provide one way to promote increased shelf stability of the dry, powdered, hemostatic composition.

In some embodiments, the protein of the second component of the dry, powdered hemostatic composition is at least partially deprotonated to form the above-mentioned free amine groups acting as an initiator. A protein may be at least partially deprotonated prior to inclusion in the dry, powdered hemostatic composition, such that the protein acts as both a crosslinking reactant component and as an initiator of the crosslinking reaction. For example, prior to inclusion in the dry, powdered hemostatic composition, the protein may be exposed to a base such that one or more acidic protons are removed from the protein. As one example, the protein may initially include lysine amino acid side chains that are protonated (having ammonium groups, —NH$_3^+$), and the protein may be exposed to a liquid under basic conditions. Under the basic conditions, a base (e.g., hydroxide ion) may deprotonate some or all of the protonated lysine amino acids of the protein to provide free amino groups (—NH$_2$). In some instances, under the basic conditions, a base (e.g., hydroxide ion) may deprotonate some or all of the protonated lysine amino acids of the protein to even provide negatively charged amide ion groups (—NH$^-$) if the base is sufficiently strong. The protein may then be provided in a solid form (e.g., as particles of a powder) in which at least some of the lysines are still present as free amino groups. In some instances, the protein may then be provided in a solid form (e.g., as particles of a powder) in which at least some of the lysines are still present as free amino groups or amide ion groups. Upon exposure to an aqueous liquid (e.g., blood), the free amino groups of the at least partially deprotonated protein may readily react with the electrophilic groups of the multifunctionalized polymeric composition (e.g., PEG(SS)2). By contrast, preparation of dry powders of proteins that does not include deprotonating the protein in such a way results in dry powdered protein components in which a greater number of potentially nucleophilic groups (e.g., lysine side chains) are in a protonated state than in the at least partially deprotonated proteins described here.

In some embodiments, the protein of the second component of the dry, powdered hemostatic composition is in a basic state, thereby acting as a reactant and an initiator of the cross-linking reaction. In this context, a protein in a basic state is one in which fewer amino acid side chains of the protein are in a protonated state than would be observed in an equivalent protein dissolved in an unbuffered pH-neutral aqueous solution. As an illustrative example, a protein may comprise amino acid side chains having varying pK$_a$s such that in a pH-neutral, unbuffered water solution, 75% of the amino side chains are in a protonated state (e.g., lysine side chains having ammonium groups) and 25% are in an unprotonated state (lysine side chains having free amino groups). If an equivalent protein (e.g., in a dry, powdered composition) is in a state where 10% of the amino acid groups are in a protonated state and 90% are in an unprotonated state, then that protein would be considered to be in a basic state. A protein may be in a basic state due to, for example, being at least partially deprotonated as described above. One way to compare the protonation states of proteins is to compare the "own charge" of the proteins. For example, to compare the protonation state of a protein in a basic state (e.g., in a dry powder) to an equivalent protein at neutral pH, the own charge of each can be determined as follows. To establish a measure indicative of the protonation state of the under neutral, unbuffered aqueous conditions, the protein can be dissolved in pH-neutral, unbuffered water and the "own charge" of that protein can be measured. Then, to establish a measure indicative of the protonation state of the protein in the basic state, the protein in the basic state can be dissolved in deionized water and the own charge of the protein in the basic state can be measured. A protein in a basic state will have a more negative own charge than an equivalent protein in pH-neutral conditions. The own charge of a protein is the net charge of the protein minus the charge of all bound ions, and is correlated to the number of protons associated with the protein. The own charge can be measured according to the method described in Fogh-Andersen, N., Bjerrum, P. J., & Siggaard-Andersen, O. (1993). Ionic binding, net charge, and Donnan effect of human serum albumin as a function of pH. *Clinical chemistry*, 39(1), 48-52, which is incorporated herein by reference in its entirety. Briefly, one can determine the own charge by dissolving the protein in a solution and measuring the difference between the number of total ions and number of free ions in the solution (using, for example flame-emission photometry, atomic absorption spectrophotometry, and ion titrators), and then using the charge neutrality condition to determine the own charge of the protein.

It has been realized and observed in the context of this disclosure that a protein (e.g., serum albumin) in a basic state may act as its own initiator to more readily undergo crosslinking with the multifunctionalized polymeric composition (e.g., PEG(SS)2), and in some instances do so even in the absence of a separate powdered initiator, such as a powdered base and/or basic buffer.

In some embodiments, a relatively large number of lysine side chains of the protein (e.g., serum albumin) are in an unprotonated (free amine) state in the dry, powdered hemostatic composition. For example, in some embodiments, at least 25%, at least 50%, at least 75%, at least 90%, at least 95%, at least 98%, or all lysine side chains of the protein are in an unprotonated state in the dry, powdered hemostatic composition.

In some embodiments, the second component comprising the protein is selected, produced or treated to act as its own initiator, when dissolved in deionized water, can produce a pH of a resulting solution that is relatively high. Dissolving the second component in deionized water and producing a pH of a resulting solution that is relatively high is considered a screening test for a property of the second component, and it should be understood that, in use, the dry, powdered hemostatic composition comprising the second component can be applied to sites where other types of liquid distinct from deionized water are present, such as blood. The protein may be able to produce a relatively high pH, for example, by being in a basic state in the dry, powdered hemostatic composition (e.g., via at least partial deprotonation). At least partial deprotonation of the protein may provide basic moieties (e.g., basic amino acid side chains) of the protein that, upon dissolution in deionized water, can react with protons and/or water molecules in the deionized water to produce hydroxide ions, thereby producing a relatively high pH. In contrast, a protein having a relatively high number of moieties in protonated states may produce fewer hydroxide ions in the water (and in fact may produce protons), resulting in a comparatively lower pH of the resulting solution. In some embodiments, the second component (e.g., comprising particles of protein such as serum albumin), when dissolved in deionized water, can produce a pH of a resulting solution of greater than or equal to 8, greater than or equal to 8.2, greater than or equal to 8.5, greater than or equal to 9, greater than or equal to 9.2, greater than or equal to 9.5, and/or up to 10, up to 10.5, up to 11, or higher. It should be understood that when considering whether a second component, when dissolved in deionized water, can produce a pH of a resulting solution in the above ranges, the amount of protein added need not be specified, so long as there exists an amount of the protein dissolvable in deionized water that can produce such a pH. That said, in some embodiments, dissolution of a relatively small amount of the second component in deionized water can produce a solution with a pH in the above ranges. For example, in some embodiments, the second component, when dissolved in deionized water to form a 25 weight by volume (w/v %) resulting solution of the protein, produces such a solution having a pH of greater than or equal to 8, greater than or equal to 8.2, greater than or equal to 8.5, greater than or equal to 9, greater than or equal to 9.2, greater than or equal to 9.5, and/or up to 10, up to 10.5, up to 11, or higher. It has been observed that when preparing a second component of a dry, powdered composition by removing water from a preparatory aqueous solution comprising a protein (as described in more detail below), the protonation state of the protein can be substantially conserved, such that the second component in the dry, powdered composition, when dissolved in deionized water, produces a resulting solution having a pH that is equal to the pH of the preparatory aqueous solution, assuming identical concentrations of the second component in each solution.

The second component (e.g., comprising a powdered form of the protein) of the dry, powdered composition can be prepared according to any of a variety of methods. Some such methods can facilitate at least partially deprotonating the protein. In some embodiments, a preparatory aqueous solution comprising an at least partially dissolved form of the protein is provided. For example, in FIG. 8, method 200 comprises step 210 of at least partially dissolving protein (e.g., albumin) in water. The water may be deionized water. In some embodiments, a resulting solution comprising the protein in an amount of 25 w/v % is produced. The pH of the resulting water comprising the at least partially dissolved protein may then be adjusted to form a preparatory aqueous solution, as shown in step 220 of FIG. 8. In some embodiments, the pH of the resulting water comprising the at least partially dissolved protein is adjusted to a pH of greater than or equal to 8, greater than or equal to 8.2, greater than or equal to 8.5, greater than or equal to 9, greater than or equal to 9.2, greater than or equal to 9.5, and/or up to 10, up to 10.5, up to 11, or higher. The pH may be adjusted, for example, by adding a base. For example, sodium hydroxide (e.g., as a 1 N NaOH solution) may be added to adjust the pH. Such a pH adjustment of the preparatory aqueous solution may at least partially (or completely) deprotonate the protein. Alternative ordering of steps may be used. For example, in some embodiments, water lacking the protein is provided at a relatively high pH (e.g., greater than or equal to 8, greater than or equal to 8.2, greater than or equal to 8.5, greater than or equal to 9, greater than or equal to 9.2, greater than or equal to 9.5, and/or up to 10, up to 10.5, up to 11, or higher), and the protein is at least partially dissolved in that water having a relatively high pH, thereby producing a preparatory aqueous solution comprising a dissolved form of the protein that maintains a pH in at least one of the ranges described above.

Figure 8:
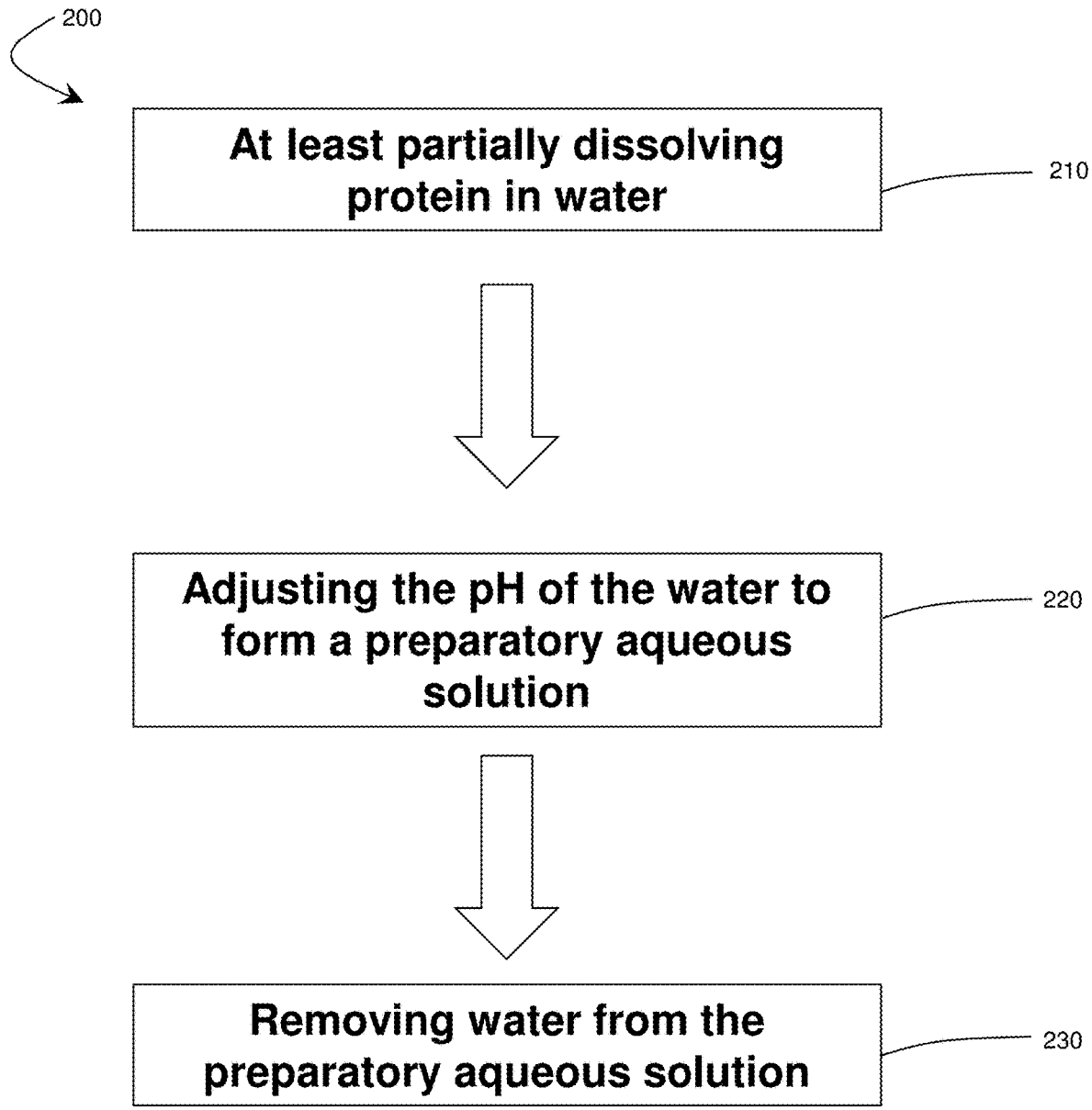
FIG. 8 shows, in accordance with certain embodiments, exemplary steps in a method for forming a protein component for a dry, powdered hemostatic composition.

In some embodiments, water is removed from the preparatory aqueous solution comprising the at least partially dissolved form of the protein, thereby forming a solid form of the protein, as show in step 230 in FIG. 8. The solid form of the protein may be further processed in some embodiments to form a powdered form of the protein. For example, the solid form of the protein may be milled to form a powder, which may, in some instances undergo a particle size selection step (e.g., via sieving).

One way to remove the water from the preparatory aqueous solution is by lyophilizing the preparatory aqueous solution. In some embodiments, lyophilizing the preparatory aqueous solution comprises exposing the preparatory aqueous solution to an environment having a temperature of less than or equal to −10° C., less than or equal to −20° C., less than or equal to −30° C., less than or equal to −40° C., and/or as low as −50° C., or lower. In some embodiments, lyophilizing the preparatory aqueous solution comprises exposing the preparatory aqueous solution to a vacuum environment having a pressure of less than or equal to 100 Pa, less than or equal to 50 Pa, less than or equal to 40 Pa, less than or equal to 33 Pa, or lower. Combinations of these conditions are possible. For example, in some embodiments, lyophilizing the preparatory aqueous solution comprises exposing the preparatory aqueous solution to an environment having a temperature of −40° C. and a pressure of 33 Pa. Other suitable methods of removing the water include, but are not limited to, spray drying, spray freeze drying, desiccation, etc.).

It has been observed in the context of the present disclosure (e.g. via high performance liquid chromatography (HPLC) experiments) that protein produced in the manner above involving at least partially deprotonating the protein generally does not necessarily result in new protein structures or change distributions of structures of the protein (e.g., monomers, dimers, etc.) observed in solution.

In some embodiments, the dry, powdered hemostatic composition is provided such that upon exposure of 0.5 g of the composition to 1.0 mL of 0.01 M phosphate buffered saline, crosslinking of the first component and the second component is initiated to form a hemostatic hydrogel having a relatively low surface pH. Such a composition may be contrasted with certain compositions that under identical conditions produce hemostatic hydrogels having relatively high surface pHs. For example, in some embodiments a relatively large amount of a base and/or basic buffer (e.g., present as a powdered basic salt or powdered basic buffer salt such as sodium bicarbonate) may be present in the composition such that a resulting hydrogel has a relatively high surface pH. In some embodiments in which a protein in a basic state (e.g., due to at least partial deprotonation) is provided in or as the second component, addition of and/or basic buffer may be unnecessary (or reduced) for satisfactory crosslinking and hydrogel formation resulting in a hemostatic hydrogel that may have a relatively low pH under these conditions. In some embodiments, upon exposure of 0.5 g of the composition to 1.0 mL of 0.01 M phosphate buffered saline, crosslinking of the first component and the second component is initiated to form a hemostatic hydrogel having a surface pH of less than or equal to 7.5, less than or equal to 7.2, less than or equal to 7, less than or equal to 6.5, less than or equal to 6.2, less than or equal to 6, and/or as low as 5.5, as low as 5, or lower.

In some aspects, kits are provided. In some embodiments, the kit contains any of the dry, powdered, crosslinking hemostatic compositions described above with, optionally, other components, or, alternatively, ingredients from which any of the dry, powdered, crosslinking hemostatic compositions described above and below can be formed. For example, the kit may comprise the first component comprising the multifunctionalized polymeric composition comprising electrophilic groups (e.g., PEG(SS)2). The kit may comprise the second component comprising the protein (which may, for example, have been treated to include groups that act as an initiator—e.g. deproteinated amine groups). In some embodiments in which a separate crosslinking initiator is present, the kit may comprise the crosslinking initiator (e.g., isolated as a third component and/or admixed with or forming part of the second component or first component, etc.). In some embodiments, the first component and the second component are packaged separately. For example, the first component may be present in the kit as a first separate dry powder, and the second component may be present in the kit as a second separate dry powder. However, in some embodiments, the first component and second component are packaged as a blended mixture. Separate packaging may promote comparatively longer shelf life than in kits in which the first component and second component are packaged as a blended mixture by avoiding reactions between the first component and second component upon exposure to, for example, ambient moisture. For kits with a powdered initiator as a third component, such a third component may be packaged separately, admixed with the second component or admixed with the first component, or all three components may be admixed together. In some embodiments, the kit comprises instructions (e.g., instructions for applying the first component and/or the second component to a bleeding/wound site to form a hemostatic hydrogel) and may include other components, such as a tamponade as described below.

In some embodiments, the dry, powdered hemostatic composition comprises the first component (e.g., comprising PEG(SS)2) in an amount of greater than or equal to 20 wt. % by mass and less than or equal to 40 wt. % by mass and the second component (e.g., comprising at least partially protonated protein such as serum albumin) in an amount of greater than or equal to 60 wt. % by mass and less than or equal to 80 wt. % by mass of the total dry, powdered composition (i.e. considering the combined weight of both components, whether or not physically admixed as provided). In some embodiments, the dry, powdered hemostatic composition comprises the first component (e.g., comprising PEG(SS)2) in an amount of greater than or equal to 25 wt. % by mass and less than or equal to 35 wt. % by mass and the second component (e.g., comprising at least partially protonated protein such as serum albumin) in an amount of greater than or equal to 65 wt. % by mass and less than or equal to 75 wt. % by mass of the total dry, powdered composition. In some embodiments, the dry, powdered hemostatic composition comprises the first component (e.g., comprising PEG(SS)2) in an amount of greater than or equal to 26 wt. % by mass and less than or equal to 28 wt. % by mass and the second component (e.g., comprising at least partially protonated protein such as serum albumin) in an amount of greater than or equal to 72 wt. % by mass and less than or equal to 74 wt. % by mass of the total dry, powdered composition. In some such embodiments, the dry, powdered composition is free of powdered basic salt and/or powdered basic buffer (e.g., powdered sodium bicarbonate). In some embodiments, the dry, powdered hemostatic composition comprises a residual quantity of solid salt attributable to a protein deprotonation/pH adjustment step. For example, in some embodiments, the dry, powdered hemostatic composition comprises solid salt attributable to a protein deprotonation/pH adjustment step in amount of less than or equal to 0.5 wt. %, less than or equal to 0.4 wt. %, less than or equal to 0.3 wt. % by mass and as low as 0.01 wt. % by mass of the total dry, powdered composition. In some embodiments, the solid attributable to a protein deprotonation/pH adjustment step comprises a base such as sodium hydroxide. In some such embodiments, the amount of solid attributable to a protein deprotonation/pH adjustment step reflects (and is calculated from) a known amount of base (e.g., NaOH) added to water comprising at least partially dissolved protein to adjust the pH prior to removal of water to form the solid form of the protein. It should be understood that some (or all) of the added base (e.g., NaOH) may react with the protein in solution (e.g., in a neutralization reaction to at least partially deprotonate the protein). Therefore, the resulting second component comprising the solid form of the protein may not literally contain intact, ionically-bound solid basic salt (e.g., NaOH), but may rather contain corresponding reaction products (e.g., sodium ions bound to counteranions). However, some intact basic salt (e.g., NaOH powder) may be present in instances where a molar excess of base is added with respect to acidic protons of the protein in the solution.

According to certain embodiments, a dry powder hemostat comprises a mixture of a multifunctionalized (e.g., difunctionalized) electrophilic polymeric first component (e.g., first dry powder comprising a multifunctionalized polymer composition such as PEG(SS)2) in any of a variety of suitable amounts in weight percent by mass in combination with a second component comprising a protein. For example, in some embodiments, the dry powder composition (e.g., dry powder mixture) comprises the first component (e.g., first dry powder) in an amount of greater than or equal to 15 wt. %, greater than or equal to 20 wt. %, greater than or equal to 25 wt. %, greater than or equal to 30 wt. %, or greater than or equal to 35 wt. % of the total mixture. In certain embodiments, the dry powder composition (e.g., dry powder mixture) comprises the first component (e.g., first dry powder) in an amount of less than or equal to 40 wt. %, less than or equal to 35 wt. %, less than or equal to 30 wt. %, less than or equal to 25 wt. %, or less than or equal to 20 wt. % of the total mixture. Combinations of the above recited ranges are also possible (e.g., the dry powder mixture comprises the first component in an amount of greater than or equal to 15 wt. % and less than or equal to 40 wt. % of the total mixture, the dry powder mixture comprises the first component in an amount of greater than or equal to 20 wt. % and less than or equal to 25 wt. % of the total mixture).

According to certain embodiments, the second component of the dry powder composition (e.g., dry powder mixture) may comprise the protein (e.g., albumin) in any of a variety of suitable amounts in weight percent by mass. For example, in certain embodiments, the dry powder composition (e.g., dry powder mixture) comprises the protein in an amount of greater than or equal to 20 wt. %, greater than or equal to 25 wt. %, greater than or equal to 30 wt. %, greater than or equal to 35 wt. %, greater than or equal to 40 wt. %, greater than or equal to 45 wt. %, greater than or equal to 50 wt. %, greater than or equal to 55 wt. %, or greater than or equal to 60 wt. % of the total mixture. In certain embodiments, the dry powder composition (e.g., dry powder mixture) comprises the protein in an amount of less than or equal to 80 wt. %, less than or equal to 75 wt. %, less than or equal to 70 wt. %, less than or equal to 65 wt. %, less than or equal to 60 wt. %, less than or equal to 55 wt. %, less than or equal to 50 wt. %, less than or equal to 45 wt. %, less than or equal to 40 wt. %, less than or equal to 35 wt. %, less than or equal to 30 wt. %, or less than or equal to 25 wt. % of the total mixture. Combinations of the above recited ranges are also possible (e.g., the dry powder mixture comprises the protein in an amount of greater than or equal to 60 wt. % and less than or equal to 80 wt. % of the total mixture, the dry powder mixture comprises the protein in an amount of greater than or equal to 65 wt. % and less than or equal to 75 wt. % of the total mixture). According to certain embodiments, the dry powder composition, when applied to blood, may require a lesser amount of the protein as compared to when the dry powder composition is applied to other media (e.g., saline) due to the presence of additional proteins (e.g., albumin) and/or cellular components in the blood.

In some embodiments, the second component of the dry powder composition (e.g., dry powder mixture) comprises the protein (e.g., albumin) in an amount of greater than or equal to greater than or equal to 20 wt. %, greater than or equal to 25 wt. %, greater than or equal to 30 wt. %, greater than or equal to 35 wt. %, greater than or equal to 40 wt. %, greater than or equal to 45 wt. %, greater than or equal to 50 wt. %, greater than or equal to 55 wt. %, greater than or equal to 60 wt. %, greater than or equal to 65 wt. %, greater than or equal to 70 wt. %, greater than or equal to 75 wt. %, greater than or equal to 80 wt. %, greater than or equal to 85 wt. %, greater than or equal to 90 wt. %, greater than or equal to 95 wt. %, greater than or equal to 98 wt. %, greater than or equal to 99 wt. %, greater than or equal to 99.8 wt. %, or greater by mass of the second component. In some embodiments, the second component of the dry powder composition (e.g., dry powder mixture) comprises the protein (e.g., albumin) in an amount of less than or equal to 99.9 wt. %, less than or equal to 99.8 wt. %, less than or equal to 99 wt. %, less than or equal to 98 wt. %, less than or equal to 95 wt. %, less than or equal to 90 wt. %, less than or equal to 85 wt. %, less than or equal to 65 wt. %, less than or equal to 60 wt. %, less than or equal to 55 wt. %, less than or equal to 50 wt. %, less than or equal to 45 wt. %, less than or equal to 40 wt. %, less than or equal to 35 wt. %, less than or equal to 30 wt. %, or less than or equal to 25 wt. % by mass of the second component. Combinations of the above recited ranges are also possible (e.g., the second component comprises the protein in an amount of greater than or equal to 20 wt. % and less than or equal to 99.9 wt. % by mass of the second component, the dry powder mixture comprises the protein in an amount of greater than or equal to 40 wt. % and less than or equal to 90 wt. % by mass of the second component).

According to some embodiments, the second component comprises a protein consisting essentially of particles having a certain particle size distribution and/or certain particle size. As used herein, the phrase "consisting essentially of particles having a certain particle size distribution" means that greater than or equal to 80 wt. % of the particles fall within the stated particle size range. In certain cases, greater than or equal to 90 wt. %, greater than or equal to 95 wt. %, greater than or equal to 98 wt. %, greater than or equal to 99 wt. %, or greater than or equal to 99.9 wt. % of the particles fall within the stated particle size range. Similarly, "consisting essentially of particles having a certain particle size" means that greater than or equal to 80 wt. % of the particles fall within a range that is ±20% of the stated particle size. In certain cases, greater than or equal to 90 wt. %, greater than or equal to 95 wt. %, greater than or equal to 98 wt. %, greater than or equal to 99 wt. %, or greater than or equal to 99.9 wt. % fall within a range that is ±20% of the stated particle size. Also similarly, "consisting essentially of particles not exceeding a certain particle size" or "consisting essentially of particles having at least a certain particle size" means that greater than or equal to 80 wt. % of the particles do not exceed, or have a size that is at least, respectively, the stated particle size. In certain cases, greater than or equal to 90 wt. %, greater than or equal to 95 wt. %, greater than or equal to 98 wt. %, greater than or equal to 99 wt. %, or greater than or equal to 99.9 wt. % of the particles do not exceed, or have a size that is at least, respectively, the stated particle size.

In certain embodiments, the protein particles are substantially spherical and the particle size is a maximum cross-sectional particle diameter. Other particle shapes, however, are also possible. Without wishing to be bound by theory, in some embodiments, the measured time it takes for the dry powdered composition to crosslink and/or the degree of crosslinking may depend on the particle size of the protein. Accordingly, it may be advantageous, in certain aspects, to employ a protein consisting essentially of particles within a certain particle size range in order to control the time it takes for the dry powdered composition to crosslink when applied to a bleeding/wound site and/or the extent of crosslinking, as is explained below in greater detail.

In certain embodiments, the protein particles may be separated by particle size (e.g., maximum particle diameter) using methods known to a person of ordinary skill in the art, such as using a sieve and/or filter to separate target particles above and below a certain sieve/filter cutoff size. In some embodiments the sieve-separated protein particle size may be further measured using spectroscopic techniques, such as dynamic light scattering (DLS), transmission electron microscopy (TEM), or scanning electron microscopy (SEM). In some aspects, the spectroscopic techniques may be used to supplement and/or confirm the particle size of the particles that have been separated using sieves and/or filters.

The protein particles may have any of a variety of suitable particle sizes. In certain embodiments, for example, the protein consists essentially of particles having a particle size of greater than or equal to 50 micrometers, greater than or equal to 100 micrometers, greater than or equal to 150 micrometers, greater than or equal to 200 micrometers, greater than or equal to 250 micrometers, greater than or equal to 300 micrometers, greater than or equal to 350 micrometers, greater than or equal to 400 micrometers, greater than or equal to 450 micrometers, or greater than or equal to 500 micrometers. In some embodiments, the protein consists essentially of particles having a particle size of less than or equal to 600 micrometers, less than or equal to 500 micrometers, less than or equal to 450 micrometers, less than or equal to 400 micrometers, less than or equal to 350 micrometers, less than or equal to 300 micrometers, less than or equal to 250 micrometers, less than or equal to 200 micrometers, less than or equal to 150 micrometers, or less than or equal to 100 micrometers. Combinations of the above recited ranges are also possible (e.g., the protein consists essentially of particles having a particle size of greater than or equal to 50 micrometers and less than or equal to 600 micrometers, the protein consists essentially of particles having a particle size of greater than or equal to 100 micrometers and less than or equal to 250 micrometers, etc.).

In certain embodiments, the second component comprises a protein that comprises a plurality of particles having a certain bulk or tapped particle density (e.g., tapped particle density). Without wishing to be bound by theory, in some embodiments, the measured time it takes for the dry powdered composition to crosslink and the degree of crosslinking may depend on the particle density (e.g., tapped particle density) of the protein. Accordingly, it may be advantageous, in certain aspects, to employ a composition comprising a protein with a certain particle density (e.g., tapped particle density) in order to control the time it takes for the dry powdered composition to crosslink or the degree of crosslinking when applied to a bleeding/wound site, as is explained below in greater detail.

In some embodiments, employing a composition comprising a protein with a certain particle density may have further advantages in addition to controlling the time it takes for the dry powdered composition to crosslink. In some aspects, for example, employing a composition comprising a protein with a certain particle density may affect the time it takes for the dry powdered composition to break the surface tension of blood, penetrate through the layer of blood, and adhere to the underlying tissue. In some embodiments, for example, a protein with a higher particle density may break the surface tension of blood, penetrate through the layer of blood, and adhere to the underlying tissue more quickly than a protein with a lower particle density.

According to some embodiments, the particle density of the protein may be measured using methods known to a person of ordinary skill in the art. For example, the particle densities referred to herein are determined using a tapped density method. Specifically, for the measurements made herein, a tapped density measurement is made as follows: the mass of the protein is measured using a standard analytical balance capable of reading up to 0.1 mg, for example, the mass of the protein may be measured by adding greater than a 6.0 mL volume of the protein to a calibrated 10 mL graduated cylinder that is capable or reading up to 0.1 mL (e.g., Pyrex No. 3022) that has been pre-tared on the analytical balance; the bottom of the graduated cylinder containing the protein is then repeatedly "tapped" against a flat surface in order to increase the packing density of the protein in the graduated cylinder until the volume of the protein does not change more than 0.1 mL between taps; and the tapped density is determined by dividing the measured mass by the measured volume.

In certain embodiments, the particle density of the protein can be controlled. In some embodiments, for example, the particle density of the protein may be changed by lyophilizing solutions of different concentrations of the protein. For example, in some embodiments, the particle density of the starting material of the protein may be determined as described above, and a solution of the protein is solubilized and lyophilized to provide a particle density that is different than the particle density of the starting material. In certain embodiments, the particle density of the protein after lyophilization is preferably lower than the particle density of the protein starting material. The final, post lyophilization density can be controlled at least in part by controlling the concentration of the protein in the solution that is lyophilized. In some embodiments, for example, more concentrated solutions lead to higher post-lyophilization densities as compared to less concentrated solutions. In some embodiments, the post-lyophilization density is lower than the particle density of the protein starting material. In certain other embodiments, the post-lyophilization density is greater than the particle density of the protein starting material. A post-lyophilization particle density that is greater than the starting material particle density may be obtained, in some embodiments, by lyophilizing solutions containing high concentrations of starting materials with low particle densities (e.g., less than 0.30 g/mL). In some embodiments, the particle density of the protein starting material may be increased by roller compacting and granulating the protein starting material. In certain embodiments, it may be advantageous to increase the particle density of the protein by roller compacting the second component comprising the protein. In some such instances, the protein is roller compacted together with a crosslinking initiator (e.g., a separate base or basic buffer).

The protein particles may have any of a variety of suitable particle densities (e.g., tapped particle densities). For example, in certain embodiments, the protein comprises a plurality of particles having a particle density of greater than or equal to 0.30 g/mL, greater than or equal to 0.35 g/mL, greater than or equal to 0.40 g/mL, greater than or equal to 0.45 g/mL, greater than or equal to 0.50 g/mL, greater than or equal to 0.55 g/mL, greater than or equal to 0.60 g/mL, greater than or equal to 0.65 g/mL, greater than or equal to 0.70 g/mL, or greater than or equal to 0.75 g/mL. In some embodiments, the protein comprises a plurality of particles having a particle density of less than or equal to 0.80 g/mL, less than or equal to 0.75 g/mL, less than or equal to 0.70 g/mL, less than or equal to 0.65 g/mL, less than or equal to 0.60 g/mL, less than or equal to 0.50 g/mL, less than or equal to 0.45 g/mL, less than or equal to 0.40 g/mL, or less than or equal to 0.35 g/mL. Combinations of the above recited ranges are also possible (e.g., the protein comprises a plurality of particles having a particle density of greater than or equal to 0.30 g/mL and less than or equal to 0.80 g/mL, the protein comprises a plurality of particles having a particle density of greater than or equal to 0.35 g/mL and less than or equal to 0.45 g/mL).

In a specific, non-limiting embodiment, the dry powder composition comprises lyophilized bovine serum albumin with a tapped particle density greater than or equal to 0.60 g/mL and less than or equal to 0.70 g/mL. In another specific non-limiting embodiment, the dry powder composition comprises lyophilized bovine serum albumin with a particle density greater than or equal to 0.20 g/mL and less than or equal to 0.40 g/mL. In another specific non-limiting embodiment, the dry powder composition comprises lyophilized human serum albumin with a particle density greater than or equal to 0.20 g/mL and less than or equal to 0.40 g/mL.

According to certain embodiments, the multifunctionalized polymeric composition describable by the formula G-LM-PEG-LM-G, I—(—X-LM-G)., and/or I-(LM-G) comprises a plurality of particles having any of a variety of suitable particle sizes and/or particle densities (e.g., tapped particle densities), which may be determined as described above in reference to the protein.

In some embodiments, the multifunctionalized polymeric composition describable by the formula G-LM-PEG-LM-G, I—(—X-LM-G)., or I-(LM-G) (e.g., PEG(SS)2, PEG(SG4), PEG(SG)42LA, and/or any other of the first component electrophilic compositions described herein (collectively "multifunctionalized polymeric composition")) comprises a plurality of particles having a particle size of greater than or equal to 10 micrometers, greater than or equal to 50 micrometers, greater than or equal to 100 micrometers, greater than or equal to 150 micrometers, greater than or equal to 200 micrometers, greater than or equal to 250 micrometers, greater than or equal to 300 micrometers, greater than or equal to 350 micrometers, greater than or equal to 400 micrometers, greater than or equal to 450 micrometers, greater than or equal to 500 micrometers, or greater than or equal to 550 micrometers. In certain embodiments, the electrophilic functionalized PEG multifunctionalized polymeric composition comprises a plurality of particles having a particle size of less than or equal to 600 micrometers, less than or equal to 550 micrometers, less than or equal to 500 micrometers, less than or equal to 450 micrometers, less than or equal to 400 micrometers, less than or equal to 350 micrometers, less than or equal to 300 micrometers, less than or equal to 250 micrometers, less than or equal to 200 micrometers, less than or equal to 150 micrometers, less than or equal to 100 micrometers, or less than or equal to 50 micrometers. Combinations of the above recited ranges are also possible (e.g., the multifunctionalized polymeric composition comprises a plurality of particles having a particle size greater than or equal to 10 micrometers and less than or equal to 600 micrometers, the multifunctionalized polymeric composition comprises a plurality of particles having a particle size greater than or equal to 200 micrometers and less than or equal to 300 micrometers).

In certain embodiments, the multifunctionalized polymeric composition comprises a plurality of particles having a particle density (e.g., tapped particle density) greater than or equal to 0.20 g/mL, greater than or equal to 0.25 g/mL, greater than or equal to 0.30 g/mL, greater than or equal to 0.35 g/mL, greater than or equal to 0.40 g/mL, greater than or equal to 0.45 g/mL, greater than or equal to 0.50 g/mL, or greater than or equal to 0.55 g/mL. In some embodiments, the multifunctionalized polymeric composition comprises a plurality of particles having a particle density (e.g., tapped particle density) less than or equal to 0.60 g/mL, less than or equal to 0.55 g/mL, less than or equal to 0.50 g/mL, less than or equal to 0.45 g/mL, less than or equal to 0.40 g/mL, less than or equal to 0.35 g/mL, less than or equal to 0.30 g/mL, or less than or equal to 0.25 g/mL. Combinations of the above recited ranges are also possible (e.g., the multifunctionalized polymeric composition comprises a plurality of particles having a particle density greater than or equal to 0.20 g/mL and less than or equal to 0.60 g/mL, the multifunctionalized polymeric composition comprises a plurality of particles having a particle density greater than or equal to 0.25 g/mL and less than or equal to 0.35 g/mL).

According to some embodiments, the crosslinking initiator (e.g. a basic salt or basic buffer salt such as sodium bicarbonate or sodium phosphate dibasic, etc.) comprises a plurality of particles having any of a variety of suitable particle sizes and/or particle densities (e.g., tapped particle densities), which may be determined as described above in reference to the protein.

In certain embodiments, the crosslinking initiator comprises a plurality of particles having a particle size of greater than or equal to 20 micrometers, greater than or equal to 50 micrometers, greater than or equal to 100 micrometers, greater than or equal to 150 micrometers, greater than or equal to 200 micrometers, greater than or equal to 250 micrometers. In some embodiments, the crosslinking initiator comprises a plurality of particles having a particle size of less than or equal to 300 micrometers, less than or equal to 250 micrometers, less than or equal to 200 micrometers, less than or equal to 150 micrometers, less than or equal to 100 micrometers, or less than or equal to 50 micrometers. Combinations of the above recited ranges are also possible (e.g., the crosslinking initiator comprises a plurality of particles having a particle size of greater than or equal to 20 micrometers and less than or equal to 300 micrometers, the crosslinking initiator comprises a plurality of particles having a particle size of greater than or equal to 50 micrometers and less than or equal to 100 micrometers).

In some embodiments, the crosslinking initiator comprises a plurality of particles having a particle density (e.g., tapped particle density) greater than or equal to 0.50 g/mL, greater than or equal to 0.60 g/mL, greater than or equal to 0.70 g/mL, greater than or equal to 0.80 g/mL, greater than or equal to 0.90 g/mL, greater than or equal to 1.00 g/mL, greater than or equal to 1.10 g/mL; greater than or equal to 1.20 g/mL, greater than or equal to 1.30 g/mL, or greater than or equal to 1.40 g/mL. In certain embodiments, the crosslinking initiator comprises a plurality of particles having a particle density (e.g., tapped particle density) less than or equal to 1.50 g/mL, less than or equal to 1.40 g/mL, less than or equal to 1.30 g/mL, less than or equal to 1.20 g/mL, less than or equal to 1.10 g/mL, less than or equal to 1.00 g/mL, less than or equal to 0.90 g/mL, less than or equal to 0.80 g/mL, less than or equal to 0.70 g/mL, or less than or equal to 0.60 g/mL. Combinations of the above recited ranges are also possible (e.g., the crosslinking initiator comprises a plurality of particles having a particle density greater than or equal to 0.50 g/mL and less than or equal to 1.50 g/mL, the crosslinking initiator comprises a plurality of particles having a particle density greater than or equal to 0.90 g/mL and less than or equal to 1.20 g/mL).

For embodiments in which the second component of the dry powder composition (e.g., second powder of a dry powder mixture) further comprises a base or basic buffer as a crosslinking initiator (e.g., sodium bicarbonate), such base or basic buffer may be present in any suitable amount. Without wishing to be bound by theory, the amount of the base or basic buffer may affect the reactivity of the dry powder composition, such as the measured time it takes for the dry powdered composition to crosslink, which is explained below in greater detail. Accordingly, in certain embodiments, it may be advantageous to select the amount of base or basic buffer in order to advance or delay hemostasis when the dry powder composition is applied to a bleeding/wound site.

The dry powder composition may comprise the base of basic buffer in any of a variety of suitable amounts. For example, in certain embodiments, the second component of the dry powder composition (e.g., dry powder mixture) comprises the basic crosslinking initiator in an amount of greater than or equal to 1 wt. %, greater than or equal to 5 wt. %, greater than or equal to 10 wt. %, greater than or equal to 15 wt. %, greater than or equal to 20 wt. %, greater than or equal to 25 wt. %, greater than or equal to 30 wt. %, greater than or equal to 35 wt. %, or greater than or equal to 40 wt. %. In certain embodiments, the second component of the dry powder composition (e.g., dry powder mixture) comprises the basic crosslinking initiator in an amount of less than or equal to 45 wt. %, less than or equal to 40 wt. %, less than or equal to 35 wt. %, less than or equal to 30 wt. %, less than or equal to 25 wt. %, less than or equal to 20 wt. %, less than or equal to 15 wt. %, less than or equal to 10 wt. %, or less than or equal to 5 wt. %. Combinations of the above recited ranges are also possible (e.g., the dry powder mixture comprises the basic crosslinking initiator in an amount of greater than or equal to 1 wt. % and less than or equal to 45 wt. %, the dry powder mixture comprises the crosslinking initiator in an amount of greater than or equal to 25 wt. % and less than or equal to 35 wt. %).

According to a specific non-limiting embodiment, the dry powder composition (e.g., dry powder mixture) comprises a first component (e.g., first dry powder) comprising PEG(SS)2, and a second component (e.g., second dry powder) comprising albumin and sodium bicarbonate, wherein the PEG(SS)2, albumin, and sodium bicarbonate are in a 1:2:1.3 mass ratio, respectively (e.g., 23 wt. % by mass PEG(SS)2, 47 wt. % by mass albumin, and 30 wt. % by mass sodium bicarbonate).

In certain embodiments, the first component (e.g., first dry powder such as PEG(SS)2) and/or the second component (e.g., second dry powder such as albumin) used herein may have a number average particle size (e.g., average cross-sectional maximum particle diameter) on the microscale. In some embodiments, the first component and/or the second component may comprise powders that have number average particle sizes (e.g., number average particle diameters) in the range of from 1 micrometer to 1000 micrometers. In some embodiments, the first component and/or the second component may comprise powders that have number average particle sizes (e.g., number average particle diameters) in the range of from 10 micrometers to 500 micrometers. The number average particle size of the first component and/or second component may be determined using spectroscopic techniques such as DLS, SEM, and/or TEM, as described above.

In any of the above described embodiments, the dry powder crosslinking hemostat composition (e.g., dry powder crosslinking hemostat mixture) may comprise other active agents or ingredients for various purposes, for example biomaterials, such as crosslinked gelatin or starch particles to allow for additional blood absorption, biologics such as thrombin to accelerate blood clotting, or any of a variety of suitable antimicrobials.

The time it takes for the dry powder composition to crosslink may determine how fast the composition forms a hemostatic hydrogel when the dry powder is applied to a bleeding/wound site. It may be beneficial for the dry powdered composition to crosslink in a substantially short time in order to quickly promote hemostasis when applied to a bleeding/wound site. In some aspects, it may be beneficial to delay formation of the hemostatic hydrogel depending on the location of the bleeding/wound site and/or the state of the patient. The "measured crosslink time" as used herein is determined by first applying the dry powder composition to a vial containing either whole blood or a solution of 0.9% normal saline as follows: to a 15.5 mm×50 mm Fisherbrand™ Vial containing a 3 mm×12.7 mm VWR™ brand Yellow Micro Stir Bar on a stir plate adjusted to 60 RPM, add either 631 microliters of whole blood with 33 microliters of 0.2 M $CaCl_2$, or 664 microliters of 0.9% normal saline, at 37° C.; to this add 166 mg of the dry powder composition (shaking lightly as need to prevent powder from sticking to the sides of the vial); the initial time ($T_0$) is recorded upon addition of the dry powder composition, and the timer is stopped (at $T_F$) when gelation causes the stir bar to stop spinning or when gelation occurs (as indicated by an obvious change in consistency). The stir bar may not come to a complete stop. If the stir bar continues beyond 3 minutes without an obvious change in consistency, a time of ">3 minutes" is recorded, but if the operator observes an obvious change in consistency indicating gel formation, the time of such observation is recorded and the test is discontinued even if the stir bar may not completely stop in all cases. The measured crosslink time is the time when the timer is stopped minus the initial time.

The dry powder composition may have any of a variety of suitable measured crosslink times. In some embodiments, for example, the dry powder composition may have a measured crosslink time of greater than or equal to 15 seconds, greater than or equal to 50 seconds, greater than or equal to 100 seconds, greater than or equal to 150 seconds, greater than or equal to 200 seconds, greater than or equal to 250 seconds, greater than or equal to 300 seconds, greater than or equal to 350 seconds, greater than or equal to 400 seconds, or greater than or equal to 450 seconds. In certain embodiments, the dry powder composition may have a measured crosslink time of less than or equal to 500 seconds, less than or equal to 450 seconds, less than or equal to 400 seconds, less than or equal to 350 seconds, less than or equal to 300 seconds, less than or equal to 250 seconds, less than or equal to 200 seconds, less than or equal to 150 seconds, less than or equal to 130 seconds, less than or equal to 100 seconds, or less than or equal to 50 seconds. Combinations of the above recited ranges are also possible (e.g., the dry powder composition may have a measured crosslink time of greater than or equal to 15 seconds less than or equal to 600 seconds, the dry powder composition may have a measured crosslink time or greater than or equal to 15 seconds and less than or equal to 150 seconds, the dry powder composition may have a measured crosslink time or greater than or equal to 15 seconds and less than or equal to 130 seconds).

In some embodiments, the measured crosslink time of the dry powder composition may depend on the type of protein and/or source of the protein. For example, when the protein comprises albumin, the measured crosslink time may depend on the source of albumin. In a certain non-limiting embodiment, for example, the protein comprises bovine serum albumin and the measured crosslink time is greater than or equal to 30 seconds and less than or equal to 50 seconds. In another non-limiting embodiment, the protein comprises human serum albumin and the measured crosslink time is greater than 40 seconds and less than 60 seconds. In yet another non-limiting embodiment, the protein may comprise recombinant human albumin and the measured crosslink time is greater than or equal to 30 seconds and less than or equal to 70 seconds.

In certain embodiments, the measured crosslink time of the dry powder composition may depend on the media to which the dry powder composition is. For example, in some embodiments, the measured crosslink time of the dry powder composition is different when mixed with whole blood as compared to normal saline (i.e., 0.90% w/v NaCl in deionized water). In some embodiments, for example, the dry powder composition has a measured crosslink time of greater than or equal to 15 seconds, greater than or equal to 50 seconds, or greater than or equal to 100 seconds when the dry powder composition is added to whole blood. In certain embodiments, the dry powder composition has a measured crosslink time of less than or equal to 150 seconds, less than or equal to 100 seconds, or less than or equal to 50 seconds when the dry powder composition is added to whole blood. Combinations of the above recited ranges are also possible (e.g., the dry powder has a measured crosslink time of greater than or equal to 15 seconds and less than or equal to 150 seconds when the dry powder composition is added to whole blood, the dry powder has a crosslink time or greater than or equal to 50 seconds and less than or equal to 100 seconds when the dry powder is added to blood). According to certain embodiments, the dry powder composition may crosslink at a substantially faster rate in blood as compared to other media (e.g., saline), due to the presence of additional proteins (e.g., albumin) and/or cellular components in the blood.

According to certain embodiments, the dry powder composition has a measured crosslink time of greater than or equal to 15 seconds, greater than or equal to 50 seconds, greater than or equal to 100 seconds, greater than or equal to 150 seconds, or greater than or equal to 200 seconds when the composition is added to normal saline. In some embodiments, the dry powder composition has a crosslink time of less than or equal to 250 seconds, less than or equal to 200 seconds, less than or equal to 150 seconds, less than or equal to 100 seconds, or less than or equal to 50 seconds when the dry powder composition is added to normal saline. Combinations of the above recited ranges are also possible (e.g., the dry powder composition has a measured crosslink time of greater than or equal to 15 seconds and less than or equal to 250 seconds when the dry powder composition is added to normal saline, the dry powder composition has a measured crosslink time or greater than or equal to 50 seconds and less than or equal to 150 seconds when the dry powder composition is added to normal saline).

As explained above, the measured crosslink time of the dry powder composition may be affected by certain properties of the reactive powder(s) (e.g., particle size and/or particle density) of the dry powder composition. For example, in some embodiments, the protein consists essentially of particles having a particle size greater than or equal to 100 micrometers, greater than or equal to 150 micrometers, or greater than or equal to 200 micrometers, and the dry powder composition may have a measured crosslink time of greater than or equal to 15 seconds and less than or equal to 75 seconds, or in other embodiments greater than or equal to 75 seconds and less than or equal to 150 seconds, when the dry powder composition is added to whole blood. In some embodiments, the protein consists essentially of particles having a particle size of less than or equal to 250 micrometers, less than or equal to 200 micrometers, or less than or equal to 150 micrometers, and the dry powder composition has a measured crosslink time of greater than or equal to 15 seconds and less than or equal to 75 seconds when the dry powder composition is added to whole blood.

In some embodiments, the protein consists essentially of particles having a particle size of greater than or equal to 100 micrometers, greater than or equal to 150 micrometers, or greater than or equal to 200 micrometers, and the dry powder composition has a measured crosslink time of greater than or equal to 15 seconds and less than or equal to 100 seconds, or in other embodiments greater than or equal to 100 seconds and less than or equal to 150 seconds, when the dry powder composition is added to normal saline. In some embodiments, the protein consists essentially of particles having a particle size of less than or equal to 250 micrometers, less than or equal to 200 micrometers, or less than or equal to 150 micrometers, and the dry powder composition has a measured crosslink time of greater than or equal to 15 seconds and less than or equal to 75 seconds when the dry powder composition is added to normal saline.

In certain embodiments, the protein comprises a plurality of particles having a tapped particle density of greater than or equal to 0.35 g/mL, or greater than or equal to 0.40 g/mL, or greater than 0.50 g/mL, or greater than 0.60 g/mL, and the dry powder composition may have a measured crosslink time of greater than or equal to 15 seconds and less than or equal to 75 seconds, or in other embodiments greater than or equal to 75 seconds and less than or equal to 150 seconds, when the dry powder composition is added to whole blood.

In some embodiments, the protein comprises a plurality of particles having a tapped particle density of less than or equal to 0.45 g/mL or less than or equal to 0.40 g/mL, and the composition may have a measured crosslink time of greater than or equal to 15 seconds and less than or equal to 75 seconds, or in other embodiments greater than or equal to 75 seconds and less than or equal to 150 seconds, when the dry powder composition is added to whole blood.

In some embodiments, the protein comprises a plurality of particles having a tapped particle density of greater than or equal to 0.35 g/mL, or greater than or equal to 0.40 g/mL, or greater than 0.50 g/mL, or greater than 0.60 g/mL, and the dry powder composition may have a measured crosslink time of greater than or equal to 15 seconds and less than or equal to 100 seconds, or in other embodiments greater than or equal to 100 seconds and less than or equal to 150 seconds when the dry powder composition is added to normal saline. In some embodiments, the protein comprises a plurality of particles having a tapped particle density of less than or equal to 0.45 g/mL or less than or equal to 0.40 g/mL, and the dry powder composition may have a measured crosslink time of greater than or equal to 15 seconds and less than or equal to 100 seconds, or in other embodiments greater than or equal to 100 seconds and less than or equal to 150 seconds, when the dry powder composition is added to normal saline.

In certain cases, the measured crosslink time of the dry powder composition may be affected by the relative amount of base or basic buffer. For example, in certain embodiments, the dry powder composition may comprise a crosslinking initiator (e.g., a base or basic buffer), and the amount of the crosslinking initiator may affect the time it takes for the composition to crosslink in various media (e.g., a solution of blood, a solution of saline) due to changes in the pH value of the solution. In some embodiments, the dry powder comprises greater than or equal to 1 wt. %, greater than or equal to 5 wt. %, greater than or equal to 10 wt. %, greater than or equal to 15 wt. %, greater than or equal to 20 wt. %, greater than or equal to 25 wt. %, greater than or equal to 30 wt. %, greater than or equal to 35 wt. %, or greater than or equal to 40 wt. % by mass base or basic buffer, and the composition has a measured crosslink time of greater than or equal to 15 seconds and less than or equal to 150 seconds when the dry powder composition is added to whole blood. In some embodiments, the dry powder comprises less than or equal to 45 wt. %, less than or equal to 40 wt. %, less than or equal to 35 wt. %, less than or equal to 30 wt. %, less than or equal to 25 wt. %, less than or equal to 20 wt. %, less than or equal to 15 wt. %, less than or equal to 10 wt. %, or less than or equal to 1 wt. % by mass base or basic buffer, and the dry powder composition has a measured crosslink time of greater than or equal to 15 seconds and less than or equal to 150 seconds when the dry powder composition is added to whole blood.

In some embodiments, the dry powder composition comprises greater than or equal to 1 wt. %, greater than or equal to 5 wt. %, greater than or equal to 10 wt. %, greater than or equal to 15 wt. %, greater than or equal to 20 wt. %, greater than or equal to 25 wt. %, greater than or equal to 30 wt. %, greater than or equal to 35 wt. %, or greater than or equal to 40 wt. % by mass base or basic buffer, and the dry powder composition has a measured crosslink time of greater than or equal to 15 seconds and less than or equal to 250 seconds, or in other embodiments greater than or equal to 250 seconds and less than or equal to 400 seconds, when the dry powder composition is added to normal saline. In some embodiments, the dry powder composition comprises less than or equal to 45 wt. %, less than or equal to 40 wt. %, less than or equal to 35 wt. %, less than or equal to 30 wt. %, less than or equal to 25 wt. %, less than or equal to 20 wt. %, less than or equal to 15 wt. %, less than or equal to 10 wt. %, or less than or equal to 1 wt. % by mass base or basic buffer, and the dry powder composition has a measured crosslink time of greater than or equal to 15 seconds and less than or equal to 250 seconds when the dry powder composition is added to normal saline.

Also disclosed herein are methods for controlling bleeding, which may employ, but are not necessarily limited to, the above described hemostatic materials. For example, in some embodiments, the method comprises applying any of the above described crosslinkable dry powder components to a bleeding/wound site (e.g., bleeding tissue). In certain embodiments, upon exposure to aqueous liquid in the bleeding/wound site, the crosslinkable dry powder crosslinks to form a hemostatic hydrogel capable of stopping and/or reducing bleeding at the bleeding/wound site.

FIG. 1, for example, shows steps in an exemplary method for forming a hemostatic hydrogel with a dry powdered mixture. In method 100, step 110 comprises admixing a first component (e.g., first dry powder) and the second component (e.g., second dry powder) to form a dry powder composition (e.g., dry powder mixture). Step 120 comprises applying the dry powder composition (e.g., dry powder mixture) to a bleeding/wound site, and step 130 comprises allowing the dry powder composition (e.g., dry powder mixture) to crosslink into a hemostatic hydrogel upon exposure to aqueous liquid in the bleeding/wound site, wherein the hemostatic hydrogel is capable of stopping and/or reducing bleeding at the bleeding/wound site. The dry, powdered hemostatic composition may be applied the bleeding/wound site as a single powder mixture. Alternatively (not pictured), in some embodiments, the first component and the second components (e.g., a first powder comprising the first component and a second powder comprising the second component), and any third component (e.g. powdered initiator) if separately packaged, are applied separately to the bleeding/wound site separately (simultaneously or sequentially) without prior formation of a powder mixture.

The hemostatic hydrogel (e.g., resulting from application of the dry powder composition to a bleeding/wound site) may be characterized by one or more measured viscoelastic properties, in some embodiments, using an ElastoSens™ Bio$^2$ instrument from Rheolution, Inc. (Montreal, Quebec, Canada). In certain embodiments, for example, the ElastoSens™ Bio$^2$ instrument may be used to measure, for example, the shear elastic modulus (G'), the gelation rate (dG'/dt), and/or other relevant viscoelastic properties. In some embodiments, the shear elastic modulus (G') may be measured as a function of time as the dry powder composition hydrates with a fluid and polymerizes. It may be beneficial, in some embodiments, for the hemostatic hydrogel to have a sufficiently large shear elastic modulus to prevent or reduce elastic deformation of the hemostatic hydrogel after application to a bleeding/wound site. In certain embodiments, it may be beneficial for the hemostatic hydrogel to have a sufficiently fast gelation rate in order to quickly promote hemostasis when the dry powder composition is applied to a bleeding/wound site.

The ElastoSens™ Bio$^2$ instrument may be operated according to the following procedure. The ElastoSens™ Bio$^2$ instrument is first calibrated (e.g. each day of use) according to a standard calibration procedures using the provided plastic calibration inserts and the associated instrument software (ElastoView™, version 18.12). After calibration, the sample holders are then placed in an incubator at 37° C. for 20 minutes. The sample holders are placed into the thermal chamber of the instrument and secured such that the sample holders cannot move. A new test is initiated using the associated instrument software. Next, 0.5 g of the dry powder composition is weighed and poured into the sample holder. A single pipette or multi-channel pipette is then filled with the hydration fluid at 37° C. (e.g. normal saline or whole blood), which is then released into the sample holder in a circular motion to ensure that all powder is evenly covered with the hydration fluid. Once sample loading is complete, the lid is of the instrument is closed and the test is started immediately.

The hemostatic hydrogel may have any of a variety of shear elastic moduli. According to certain embodiments, for example, the hemostatic hydrogel may have a maximum shear elastic modulus (G') greater than or equal to 1000 Pa, greater than or equal to 2000 Pa, greater than or equal to 3000 Pa, greater than or equal to 4000 Pa, greater than or equal to 5000 Pa, greater than or equal to 6000 Pa, greater than or equal to 7000 Pa, greater than or equal to 8000 Pa, greater than or equal to 9000 Pa, greater than or equal to 10000 Pa, greater than or equal to 11000 Pa, greater than or equal to 12000 Pa, greater than or equal to 13000 Pa, greater than or equal to 14000 Pa, greater than or equal to 15000 Pa, greater than or equal to 16000, greater than or equal to 18,000, or greater than or equal to 19000 Pa. In certain embodiments, the hemostatic hydrogel has a shear elastic modulus less than or equal to 20000 Pa, less than or equal to 19000 Pa, less than or equal to 18000 Pa, less than or equal to 17000 Pa, less than or equal to 16000 Pa, less than or equal to 15000 Pa, less than or equal to 14000 Pa, less than or equal to 13000 PA, less than or equal to 12000 Pa, less than or equal to 11000 Pa, less than or equal to 10000 Pa, less than or equal to 9000 Pa, less than or equal to 8000 Pa, less than or equal to 7000 Pa, less than or equal to 6000 Pa, less than or equal to 5000 Pa, less than or equal to 4000 Pa, less than or equal to 3000 Pa or less than or equal to 2000 Pa. Combinations of the above recited ranges are also possible (e.g., the hemostatic hydrogel has a shear elastic modulus of greater than or equal to 1000 Pa and less than or equal to 20000 Pa, the hemostatic hydrogel has a shear elastic modulus of greater than or equal to 4000 Pa and less than or equal to 10000 Pa). Other ranges are also possible.

The dry powder composition may have any of a variety of suitable gelation rates. As used herein, the term "gelation rate" refers to the speed at which hydrogel formation occurs over time, measured as the derivative of the shear elastic modulus over the derivative of time (dG'/dt). In some embodiments, for example, the dry powder composition has a gelation rate of greater than or equal to 20 Pa/sec, greater than or equal to 50 Pa/sec, greater than or equal to 100 Pa/sec, greater than or equal to 150 Pa/sec, greater than or equal to 200 Pa/sec, greater than or equal to 250 Pa/sec, greater than or equal to 300 Pa/sec, greater than or equal to 350 Pa/sec, greater than or equal to 400 Pa/sec, or greater than or equal to 450 Pa/sec. In certain embodiments, the dry powder composition has a gelation rate less than or equal to 500 Pa/sec, less than or equal to 450 Pa/sec, less than or equal to 400 Pa/sec, less than or equal to 350 Pa/sec, less than or equal to 300 Pa/sec, less than or equal to 250 Pa/sec, less than or equal to 200 Pa/sec, less than or equal to 150 Pa/sec, less than or equal to 100 Pa/sec, or less than or equal to 50 Pa/sec. Combinations of the above recited ranges are also possible (e.g., the dry powder composition has a gelation rate of greater than or equal to 20 Pa/sec and less than or equal to 500 Pa/sec, the dry powder composition has a gelation rate of greater than or equal to 50 Pa/sec and less than or equal to 250 Pa/sec). Other ranges are also possible.

Figure 7:
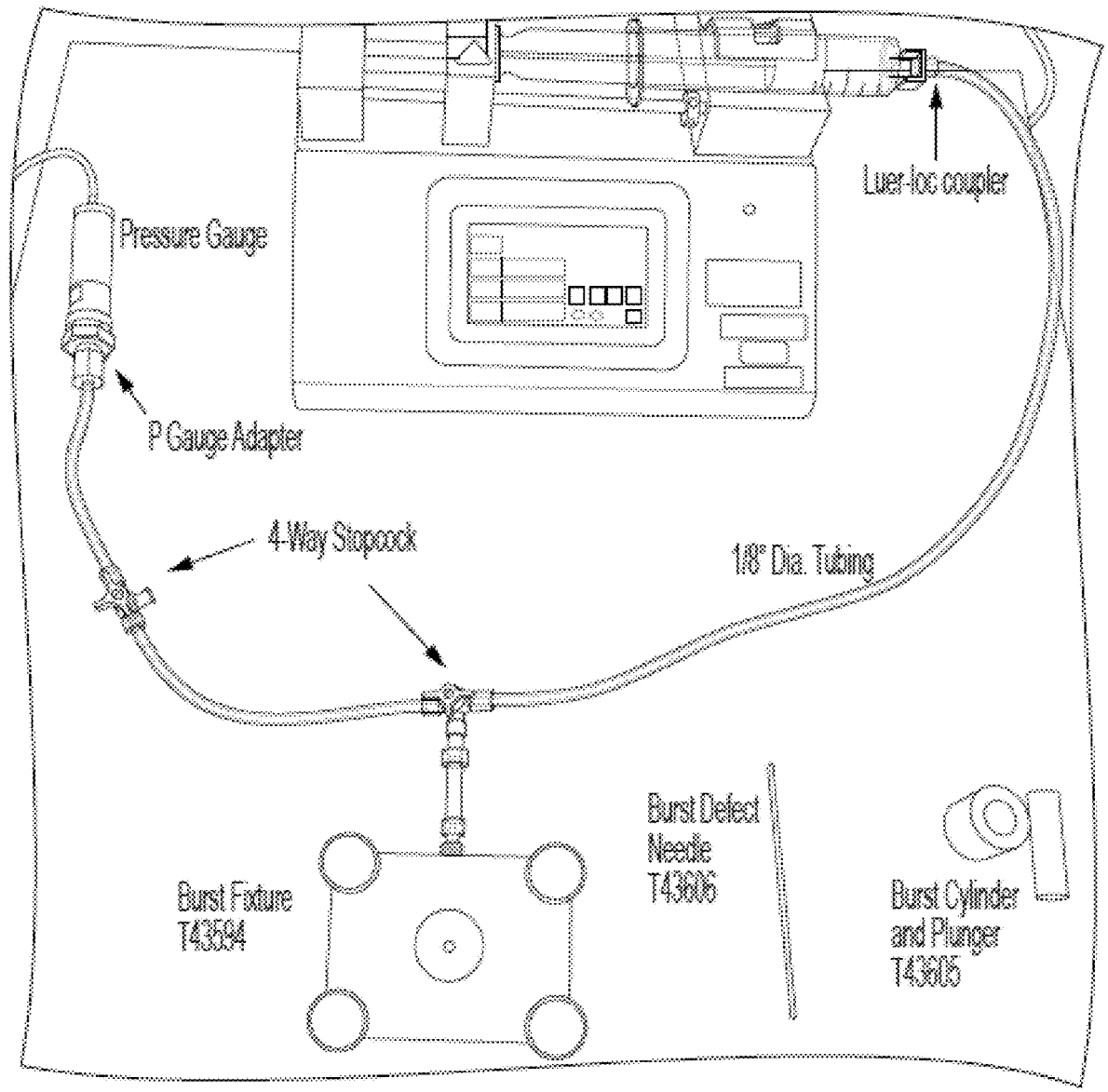
FIG. 7 shows, in accordance with certain embodiments, a test fixture set up for measuring the burst strength of a hydrogel formed from a dry powdered composition.

According to certain embodiments, the adherence of the hemostatic hydrogel compositions described herein once formed upon crosslinking can be determined by a burst pressure model based on ASTM F2392-04, (the Standard Test Method for Surgical Sealants). According to certain embodiments, the test is designed to determine the pressure needed to rupture a sealant patch covering a simulated liquid leak and indirectly measure the adhesion property of the sealant to simulated tissue. Briefly, a pressure gauge, syringe pump, and burst fixture are assembled as shown in FIG. 7. The burst fixture is described in more detail in the ASTM F2392-04 standard protocol. All tubing is filled with 0.9% saline that has been dyed with a colored food dye (2-3 drops per L) so that no air bubbles are present in the tubing. Once the tubing is filled with the 0.9% saline, the line to all tubing is opened and the syringe is pushed until the saline starts to come out of the top hole of the burst fixture. Next, an appropriately sized piece of collagen is cut and then rinsed a minimum of three times in deionized water in a 500 mL beaker to remove glycerol. The collagen is cut into 2 inch wide strips and transferred to a new 500 mL beaker of deionized water to soak for a minimum of ten minutes. Next, the top of the burst fixture is removed, and a single piece of collagen is placed over the opening of the burst fixture. The top of the burst fixture is then placed over the collagen and secured tightly. A burst defect needle (e.g., as shown in FIG. 7) is used to create a single defect in the center of the collagen by piercing the needle straight down the center of the hole in the burst fixture and straight back up. The burst cylinder (e.g., as shown in FIG. 7) is then placed on top of the fixture on top of the collagen. The dry powder composition is weighed in amount of 166 mg and poured into the burst cylinder. Next, 250 microliters of saline is pipetted into the cylinder directly onto the dry powder composition. Immediately after pipetting the saline, the burst plunger (e.g., as shown in FIG. 7) is placed into the burst cylinder on top of the hydrated composition. The hydrated composition is allowed to polymerize for 2.5 minutes. Next, the burst cylinder is removed by holding down the top of the burst plunger and pulling the cylinder straight up and off the top surface of the burst fixture. Once the cylinder has been released from the burst fixture, the plunger and cylinder are tilted and lifted to the side and then up and away from the polymerized composition. The sample is then inspected to ensure that removal of the cylinder and/or plunger did not disrupt the polymerized composition. A computer and appropriate software (e.g., Omega Digital Transducer Application, v. 2.3.0.300) is then used to record pressure readings. The polymerized composition is observed until the sample and/or substrate fails, a large pressure drop occurs, or the pressure plateaus for 30 seconds. Substrate failure occurs if the collagen rips separate from the material. Cohesive failure occurs if there is a defect through the polymerized composition. Cohesive and substrate failure occurs if the collagen and polymerized composition rip away from the defect site. Adhesive failure occurs if there is a defect between the material and the substrate interface.

In certain embodiments, the burst pressure of the hemostatic hydrogel measured by such test is greater than or equal to 10 mm Hg, greater than or equal to 50 mm Hg, greater than or equal to 100 mm Hg, greater than or equal to 150 mm Hg, greater than or equal to 200 mm Hg, greater than or equal to 250 mm Hg, greater than or equal to 300 mm Hg, or greater than or equal to 350 mm Hg. In certain embodiments, the burst pressure of the hemostatic hydrogel is less than or equal to 400 mm Hg, less than or equal to 350 mm Hg, less than or equal to 300 mm Hg, less than or equal to 250 mm Hg, less than or equal to 200 mm Hg, less than or equal to 150 mm Hg, less than or equal to 100 mm Hg, or less than or equal to 50 mm Hg. Combinations of the above recited ranges are also possible (e.g., the burst pressure of the hemostatic hydrogel is greater than or equal to 10 mm Hg and less than or equal to 350 mm Hg).

According to certain embodiments, the hemostatic efficiency of the hemostatic hydrogel compositions can be determined in animal models of controlled bleeding by the number of cycles of manually applied pressure required to achieve hemostasis upon application of the dry powder mixture hemostats, as described above. In some embodiments, the number of pressure cycles required to achieve hemostasis upon application of the dry powder mixture hemostats is greater than or equal to 1 cycles, greater than or equal to 2 cycles, or greater than or equal to 3 cycles. According to certain embodiments, the number of pressure cycles required to achieve hemostasis upon application of the dry powder mixture hemostats is less than or equal to 4 cycles, less than or equal to 3 cycles, or less than or equal to 2 cycles. Combinations of these ranges are also possible (e.g., the number of pressure cycles required to achieve hemostasis upon application of the dry powder mixture hemostats is greater than or equal to 1 cycle and less than or equal to 3 cycles).

According to certain embodiments, the hemostatic efficiency of the hemostatic hydrogel compositions can also be determined by the time it takes to achieve hemostasis upon application of the dry powder mixture hemostats described herein. According to certain embodiments, the time it takes to achieve hemostasis upon application of the dry powder mixture hemostats is less than or equal to 2.5 minutes, less than or equal to 2.0 minutes, less than or equal to 1.5 minutes, less than or equal to 1.0 minute, less than or equal to 0.5 minutes, or less than or equal to 0.2 minutes.

In some embodiments, the hemostatic efficiency of the hemostatic hydrogel compositions can also be determined by the percent of treated defects achieving and maintaining hemostasis upon application of the dry powder mixture hemostats described herein. According to some embodiments, the percent of treated defects achieving and maintaining hemostasis upon application of the dry powder mixture is greater than or equal 70%, greater than or equal to 75%, greater than or equal to 80%, greater than or equal to 85%, greater than or equal to 90%, greater than or equal to 95%, or greater than or equal to 99%, or 100%.

In certain embodiments, the dry powder composition (e.g., dry powder mixture) may be prepared and/or admixed by any of a variety of suitable methods. For example, in some embodiments, the dry powder mixture is prepared by ball milling (e.g., the dry powder mixture may be ground in a ball mill). In certain embodiments, the dry powder mixture is prepared and/or admixed by grinding with a mortar and pestle. In some embodiments, the dry powder mixture is prepared and/or admixed using a rotary mixer.

According to certain embodiments, the dry powder composition (e.g., dry powder mixture) can be provided (e.g., packaged) as a sealed, admixed powder. For example, in some cases, the dry powder mixture is provided in a vial and/or ampoule (e.g., a flame-sealed vial and/or ampoule). In certain embodiments, the vial and/or ampoule containing the dry powder mixture may be attached to a sprayer that is capable of spraying the powder (e.g., onto a bleeding/wound site). In yet other embodiments, the dry powdered components could be formed into one or two component paste, putty or wax forms for use as crosslinking patching/filling materials—e.g. in bone bleeding applications.

The dry, powdered hemostatic compositions described herein may be provided in any of a variety of suitable forms. In some embodiments, dry, powdered hemostatic compositions comprise at least a first dry powder and a second dry powder (and optionally a third dry powder, etc.). The first dry powder may comprise a first component described above. For example, in some embodiments, the first dry powder comprises a multifunctionalized polyalkylene oxide-based polymer comprising electrophilic groups (e.g., PEG(SS)2). The second powder may comprise a second component described above. For example, the second dry powder may comprise a protein (e.g., albumin).

In some embodiments, the dry, powdered hemostatic composition comprises at least one composite powder. For example, the dry, powdered hemostatic composition may comprise a single dry powder that is a composite of some or all of the components described above (e.g., a single dry powder of particles comprising a nucleophilic component (e.g., albumin) coated on an electrophilic component (e.g., PEG(SS)2). Such a powder of coated particles could be prepared, for example, by spray-coating using a solvent in which the components are unreactive (e.g., a non-aqueous solvent). In some embodiments, the dry, powdered composition comprises a dry powder mixture of multiple dry powders (e.g., the first dry powder and second dry powder). In other embodiments, the first dry powder and the second dry powder are provided as separated, unmixed powders (e.g., as packaged), and are combined prior to or upon use (e.g., prior to or as applying to a bleeding/wound site).

In embodiments in which a crosslinking initiator (e.g., base or basic buffer) is present in the dry, powdered, hemostatic composition, the crosslinking initiator may be incorporated in any of a variety of suitable forms. For example, in some embodiments, the first dry powder comprises the crosslinking initiator. In some such embodiments, the composition comprises a first dry powder comprising a first component comprising a powder mixture of or composite particles of a reactive electrophilic compound (e.g., a multifunctionalized polyalkylene oxide-based polymer functionalized with electrophilic groups) and the crosslinking initiator (e.g., a base or basic buffer). In some embodiments, a first dry powder comprises particles of the reactive electrophilic compound spray-coated with crosslinking initiator, or vice versa. In some embodiments, the second dry powder comprises the crosslinking initiator. In some such embodiments, the composition comprises a second dry powder comprising a second component comprising a power mixture of or composite particles of a reactive nucleophilic compound (e.g., a protein such as albumin) and the crosslinking initiator (e.g., a base or basic buffer). In some embodiments, a second dry powder comprises particles of the reactive nucleophilic compound spray-coated with crosslinking initiator, or vice versa.

In some embodiments, the crosslinking initiator is provided as a powder separate from the reactive electrophilic (e.g., PEG(SS)2) or nucleophilic (e.g., albumin) compounds above. For example, in some embodiments, the dry, powdered hemostatic composition comprises a first dry powder comprising the first reactive electrophilic component, a second dry powder comprising a reactive nucleophilic compound (e.g., a protein such as albumin), and a third dry powder comprising the crosslinking initiator (e.g., a base or basic buffer). The first, second, and third dry powders may be packaged separately or combined as a dry powder mixture.

In some embodiments, the dry, powdered hemostatic composition comprises a single dry powder comprising composite particles formed of a reactive nucleophilic compound, a crosslinking initiator, and a reactive electrophilic compound. For example, the dry, powdered hemostatic composition comprises a single dry powder of particles formed of a nucleophilic component (e.g., albumin) coated with a crosslinking initiator (e.g., a base or basic buffer), which is in turn coated with an electrophilic component (e.g., PEG(SS)2). Other configurations of the components are also possible. Such a powder of coated particles could be prepared, for example, by spray-coating using a solvent in which the components are unreactive (e.g., a non-aqueous solvent).

In certain embodiments, it may be advantageous to reduce the physical contact between certain components of the composition prior to applying the dry powder mixture to a bleeding/wound site. In some embodiments, for example, physical contact between the multifunctionalized polymeric composition (e.g., PEG(SS)2) and one or more components of the dry powdered composition, such as the crosslinking initiator (e.g., base or basic buffer) or the protein (e.g. albumin), may be reduced prior to applying the dry powder mixture to a bleeding/wound site. In some embodiments, for example, reducing the physical contact between the multifunctionalized polymeric composition and the crosslinking initiator may avoid chemical reactions between the two that can occur during storage, thereby increasing the overall shelf-life of the dry powder composition. As would be understood by a person of ordinary skill in the art, the multifunctionalized polymeric composition (e.g., PEG(SS)2), in some embodiments, is temperature and/or moisture sensitive. For example, in certain non-limiting embodiments, one or more ester bonds of the multifunctionalized polymeric composition may be hydrolyzed in the presence of moisture (e.g., inherent in the atmosphere), which, in some embodiments, is facilitated and/or accelerated by the presence of the crosslinking initiator (e.g., base or basic buffer). Therefore, in certain embodiments, reducing the physical contact between the multifunctionalized polymeric composition and the crosslinking initiator may inhibit such hydrolysis from occurring during product storage, therefore increasing the overall shelf-life of the dry powder composition. It may be advantageous, in some embodiments, to reduce the physical contact between the multifunctionalized polymeric composition and the protein (e.g., albumin) in order to prevent hydrolysis that may occur when the multifunctionalized polymeric composition is in contact with inherent moisture present within the protein.

In certain embodiments, reducing the physical contact comprises lowering (or eliminating) the surface area (e.g., points of contact) between the multifunctionalized polymeric composition and one or more components of the dry powdered composition, such as the crosslinking initiator (e.g., base or basic buffer) or the protein (e.g., albumin). In some embodiments, for example, the protein and/or crosslinking initiator may be manipulated such that there is limited physical contact between the multifunctionalized polymeric composition and the crosslinking initiator. According to some embodiments, for example, the protein may be roller compacted and/or granulated with the crosslinking initiator (e.g., base or basic buffer) prior to mixing with the multifunctionalized polymeric composition. In other embodiments, the protein may be spray coated onto and/or over the crosslinking initiator (e.g., base or basic buffer) prior to mixing with the multifunctionalized polymeric composition, such that, upon mixing, the multifunctionalized polymer composition is substantially only in contact with the protein and not the crosslinking initiator during storage.

In certain embodiments, the multifunctionalized polymeric composition is manipulated such that there is limited physical contact between the multifunctionalized polymeric composition and one or more other components of the dry powdered composition (e.g., the crosslinking initiator and/or the protein). In some embodiments, for example, the multifunctionalized polymeric composition may be coated with an inert material. The inert material may be, in some embodiments, a polymer. Any of a variety of suitable polymers that are suitable to coat and will not destroy or substantially degrade the reactivity of the multifunctionalized polymeric composition may be employed. Suitable polymers include those polymers that are biodegradable, biocompatible, and/or soluble or water dispersible. In some embodiments, for example, such polymer is polyvinylpyrrolidone (PVP) or hydroxypropyl methylcellulose (HPMC).

In certain cases, a hemostatic article comprises a powdered hemostatic composition used with, in contact with, or otherwise associated with a tamponade device. Applying a reactive, dry, powdered hemostatic composition to a bleeding wound using a tamponade may further reduce or stop bleeding at a bleeding/wound site upon formation of a hydrogel due to cross-linking of components of the hemostatic composition compared to use of the dry, powdered hemostatic compositions alone. The presence of a tamponade can, in some cases, improve the efficacy of dry, powdered hemostatic compositions in applications where high flow bleeding occurs. In some embodiments, the tamponade is a biodegradable tamponade. Combining a reactive, dry, powdered hemostatic composition with a biodegradable tamponade can, in some cases, provide for a hemostatic device that can be easily applied to a wound or bleeding site while improving certain performance aspects of the reactive hemostats. For example, applying a dry, powdered hemostatic composition in contact with a biodegradable tamponade can, in some cases, mitigate adhesion between, polymerized hemostatic composition and, for example, a non-biodegradable applicator or material otherwise used to contact the hemostatic composition, such as gauze.

In some cases, the reactive, dry, powdered hemostatic composition that is used with (e.g. is in contact with) the tamponade is one of the dry, powdered hemostatic compositions described above. For example, in some embodiments, a dry, powdered hemostatic composition comprising a first component comprising a difunctionalized polymer (e.g., PEG(SS)2) and a second component comprising a protein (e.g., albumin) is in contact with the tamponade.

The tamponade can comprise any of a variety of suitable materials. In certain cases, the tamponade is in the form of a foam having any suitable form factor or aspect ratio. For example, the tamponade may be in the form of a sheet or layer. In some cases, the tamponade is or comprises collagen (e.g., collagen foam). One such collagen-containing tamponade is an Ultrafoam™ tamponade. In other cases, the tamponade is or comprises gelatin (e.g., a gelatin foam). One such gelatin-containing tamponade is Gelfoam™. In certain embodiments, the tamponade comprises carboxymethylcellulose (CMC). In some embodiments, the tamponade comprises a polysaccharide. As an example, in some embodiments, the tamponade comprises a starch foam. In certain embodiments, the starch foam may be degradable, dispersible, and/or soluble. The reactive, dry, powdered hemostatic composition in contact with the tamponade (e.g., the Ultrafoam™ tamponade, the tamponade comprising a starch foam, etc.) may be located relatively close to the surface of the tamponade. For example, in some cases the reactive, dry, powdered hemostatic composition is in contact predominately with an external surface of the tamponade. In certain embodiments, the reactive, dry, powdered hemostatic composition is contained within the tamponade (e.g., the tamponade is impregnated with the reactive, dry, powdered hemostatic composition).

In some embodiments, the reactive, dry, powdered hemostatic composition is applied to a bleeding/wound site at a different time than is the tamponade. For example, in some embodiments, a dry, powdered hemostatic composition is applied to a bleeding/wound site, and subsequently the tamponade is applied to the bleeding/wound site (optionally with an application of steady or intermittent manual pressure to the tamponade). However, in certain cases, the reactive, dry, powdered hemostatic composition and the tamponade (e.g., containing the dry, powdered hemostatic composition) are applied to the bleeding/site at the same time.

U.S. Provisional Patent Application No. 63/131,267, filed Dec. 28, 2020, and entitled "Reactive Dry Powder Hemostatic Materials Comprising a Protein and a Multifunctionalized Polyethylene Glycol Based Crosslinking Agent," is incorporated herein by reference in its entirety for all purposes.

Example 1

The following example describes the hemostatic efficacy of a PEG(SS)2-based dry powder mixture in a porcine spleen biopsy defect model. The dry powder mixture was prepared by mixing PEG(SS)2 (119 mg), bovine serum albumin (BSA) (228 mg) and 153 mg of sodium bicarbonate (153 mg) in a mass ratio of 1:2:1.3. The material was tested for hemostatic efficacy in a porcine spleen biopsy defect bleeding model. Briefly, a 10 mm diameter biopsy defect to a depth of about 5 mm was made in the spleen. Next, 0.5 g of the dry powder mixture was applied to the defect and a 3 cm×3 cm piece of Ultrafoam was placed on top of the powder to prevent it from sticking to the gauze used for application of pressure. Cessation of bleeding was assessed after thirty second tamponade or pressure cycles. The dry powder mixture had improved efficacy compared to other commercially available hemostatic agents (see Table 1). The material worked consistently (9 out of 10 in one pressure cycle) and adhered tenaciously to the tissue.

TABLE 1

Hemostatic efficacy of PEG(SS)2-based dry powder mixture in a porcine spleen biopsy defect model.

| Sample | Description | # of Defects Treated | # of Pressure Cycles Required to Achieve Hemostasis (mean ± std. dev.) | Time to Hemostasis (min) (mean ± std. dev.) | % of Defects Achieving and Maintaining Hemostasis (2 min. Observation) |
|---|---|---|---|---|---|
| PEG(SS)2-based dry powder mixture + Ultrafoam ™ | powder + foam sponge | 10 | 1.2 ± 0.6 | 1.1 ± 0.4 | 100 |
| Ultrafoam ™ | foam sponge | 8 | 2.4 ± 1.3 | 2.2 ± 1.1 | 75 |
| Floseal ™ | flowable paste (gelatin + thrombin) | 7 | 1.9 ± 1.1 | 1.7 ± 0.9 | 71 |

Example 2

The following example describes the hemostatic efficacy of the PEG(SS)2-based dry powder mixture prepared in Example 1 in a heparinized porcine spleen biopsy defect model. Heparin was used to mimic clinically relevant coagulopathies and heparinization during cardiovascular surgery. Briefly, an initial IV bolus of 150 U heparin/kg was given to increase the activated clotting time (ACT) to about 2-3× baseline. Testing of the dry powder mixture followed the description in Example 1 and the results were compared to other commercially available hemostatic agents (see Table 2). The dry powder mixture worked consistently in one pressure cycle and adhered tenaciously to the tissue. Efficacy of the dry powder mixture in the heparinized model was similar to the efficacy in the non-heparinized model described in Example 1. In contrast, the competitive products had reduced efficacy in the heparinized model.

Example 3

The following example describes the hemostatic efficacy of the PEG(SS)2-based dry powder mixture prepared in Example 1 in a heparinized porcine spleen abrasion model. The abrasion was made using the rough surface of an electrocautery pad over an area of 0.5"×0.5" and created an oozing bleed. Heparin was used to mimic clinically relevant coagulopathies and heparinization during cardiovascular surgery. Briefly, an initial IV bolus of 150 U heparin/kg was given to increase the activated clotting time (ACT) to about 2-3× baseline. Five hundred milligrams of the dry powder mixture was sprinkled over the bleeding area, no tamponade or pressure cycle was applied, and hemostasis was assessed after an initial 30 seconds. If hemostasis was achieved a two minute observation period was used to assess rebleeds. If hemostasis was achieved and maintained, the wound site was irrigated with saline and re-assessed for hemostasis. Results were compared to other commercially available hemostatic agents (see Table 3). The dry powder mixture worked better than the competitive products and adhered tenaciously to the tissue.

TABLE 2

Hemostatic efficacy of PEG(SS)2-based dry powder mixture in a heparinized porcine spleen biopsy defect model.

| Sample | Description | # of Defects Treated | # of Pressure Cycles Required to Achieve Hemostasis (mean ± std. dev.) | Time to Hemostasis (min) (mean ± std. dev.) | % of Defects Achieving and Maintaining Hemostasis (2 min. Observation) |
|---|---|---|---|---|---|
| PEG(SS)2-based dry powder mixture + Ultrafoam ™ | powder + foam sponge | 6 | 1.0 ± 0.0 | 1.0 ± 0.0 | 100 |
| Ultrafoam ™ | foam sponge | 6 | 7.0 ± 3.5 | 5.6 ± 3.1 | 17 |
| Floseal ™ | flowable paste (gelatin + thrombin) | 6 | 4.8 ± 3.4 | 4.2 ± 2.7 | 0 |

TABLE 3

Hemostatic efficacy of PEG(SS)2-based dry powder mixture in a heparinized porcine spleen abrasion model.

| Sample | Description | # of Defects Treated | % Hemostasis Achieved | % Hemostasis Maintained | % Hemostasis Maintained After Irrigation |
|---|---|---|---|---|---|
| PEG(SS)2 dry powder mixture | powder | 8 | 75 | 75 | 75 |
| Raplixa ™ Powder | powder (trehalose/ fibrinogen/ thrombin) | 8 | 50 | 13 | 0 |
| Surgicel ™ Powder | oxidized regenerated cellulose powder | 5 | 0 | 0 | 0 |

Example 4

The following example describes the demonstration of sealant properties of the PEG(SS)2-based dry powder mixture prepared in Example 1 in an in vitro burst pressure model (based on ASTM F2392-04; Standard Test Method for Surgical Sealants). The test is designed to determine the pressure needed to rupture a sealant patch covering a simulated liquid leak and indirectly measure the adhesion property of the sealant to simulated tissue. Briefly, a hydrated collagen casing membrane was secured in a burst pressure fixture and a hole was created with a 3-0 RB1 suture needle. The dry powder mixture was applied to the membrane and hydrated with saline. A syringe pump supplied saline to the fixture at a flow rate of 2 mL/min and burst pressure at failure was recorded. The material tested at two conditions of amount and cure time exhibited sealant properties (see Table 4).

TABLE 4

Sealant properties of PEG(SS)2-based dry powder mixture in a burst pressure model.

| Test | Amount of Powder Mixture (mg) | Amount of Saline Hydration (µl) | Cure Time Allowed Prior to Test | Burst Pressure (mm Hg) |
|---|---|---|---|---|
| Minimal dry powder mixture/ short cure time (n = 13) | 35 | 40 | 15 sec | 90 ± 58 |
| Moderate dry powder mixture/ long cure time (n = 6) | 166 | 250 | 5 min | 236 ± 78 |

Example 5

Figure 2A:
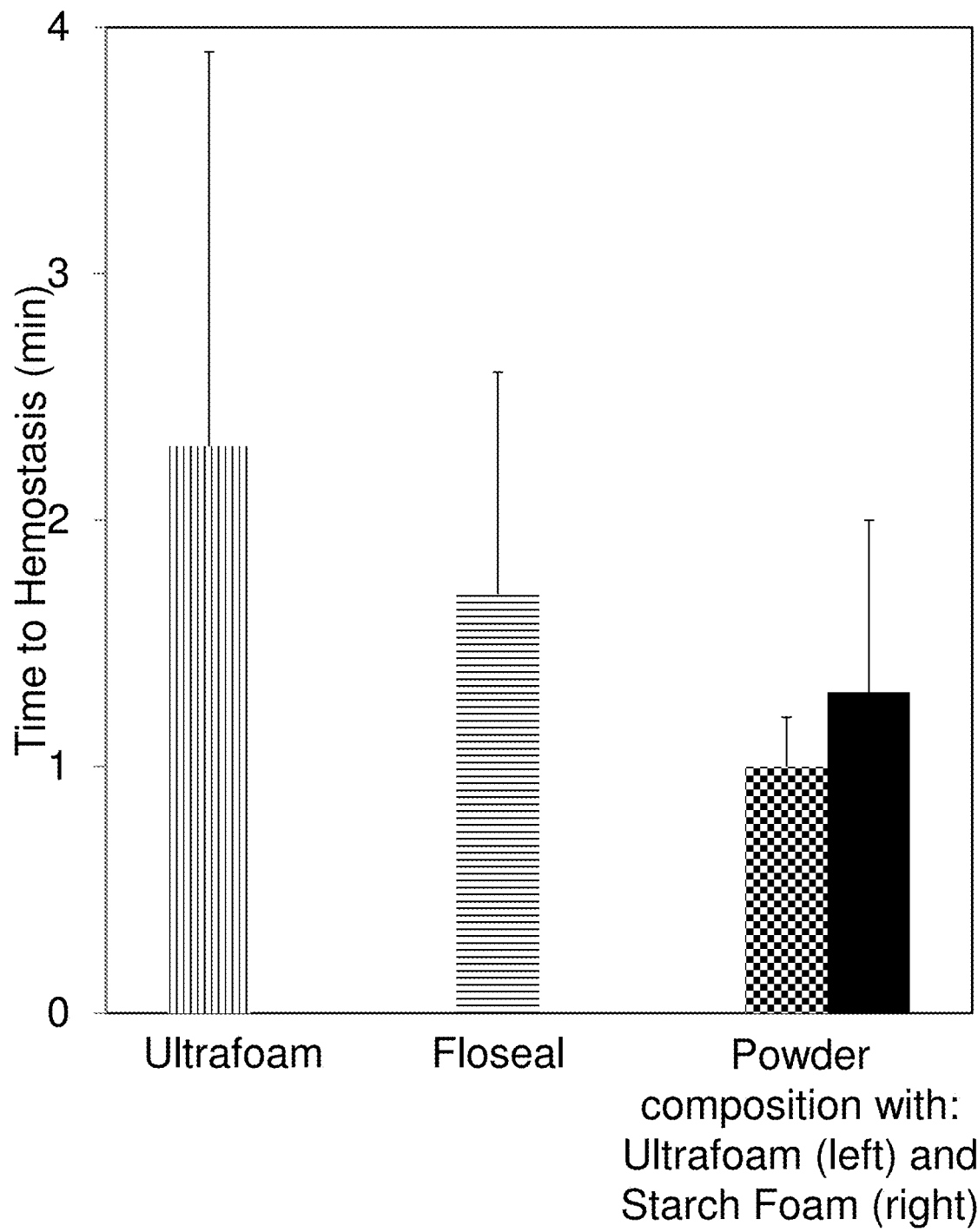
FIG. 2A shows, in accordance with certain embodiments, the measured crosslink time for a dry powdered composition to achieve hemostasis as compared to other commercially available hemostats.
Figure 2B:
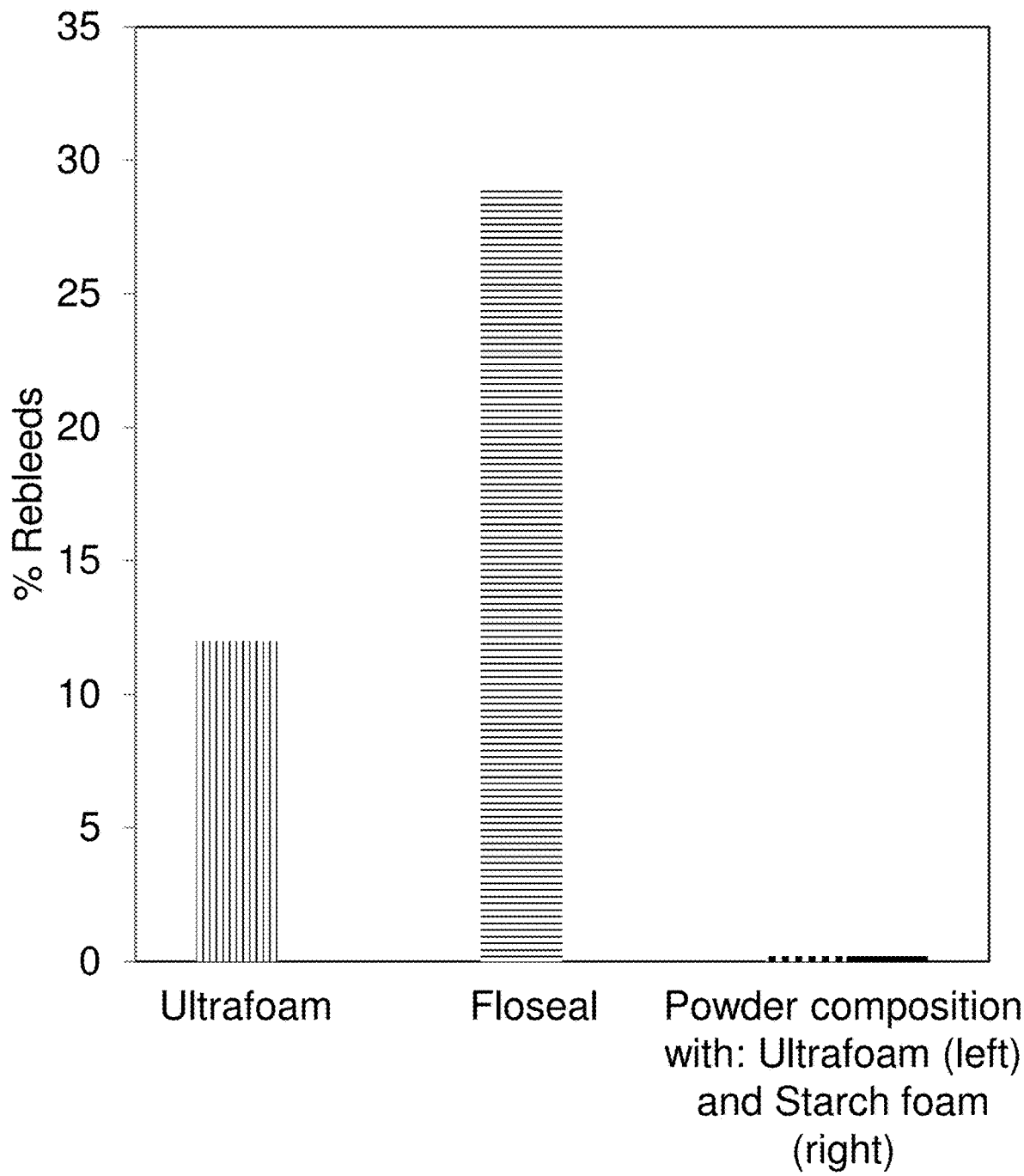
FIG. 2B shows, in accordance with certain embodiments, the percent of rebleeds after application of a dry powdered composition to a wound site as compared to other commercially available hemostats.

The following examples describes the hemostatic efficacy of a PEG(SS)2 dry powder composition in a porcine spleen biopsy defect bleeding model (modified wet field model). The material prepared in Example 1 was tested for hemostatic efficacy in a porcine spleen biopsy defect bleeding model as described previously in Example 1. However, in order to increase the hemostatic challenge in a realistic surgical scenario, the material was applied to an actively bleeding site, instead of blotting the defect dry prior to placement. Briefly, a 10 mm diameter biopsy defect to a depth of 5 mm was made in the spleen. The defect was allowed to fill with blood and then 0.5 g of the reactive powder mixture was applied to the defect and a 3 cm×3 cm piece of Ultrafoam™ or a tamponade comprising a starch foam was placed on top of the powder to prevent it from sticking to the gauze used for application of tamponade. Cessation of bleeding was assessed after 30 second tamponade cycles. The dry reactive powder mixture had improved efficacy compared to other commercially available hemostatic agents, as shown by the reduced time to achieve hemostasis in FIG. 2A and the fewer percent rebleeds during a 2 minute observation after hemostasis in FIG. 2B.

Example 6

Figure 3:
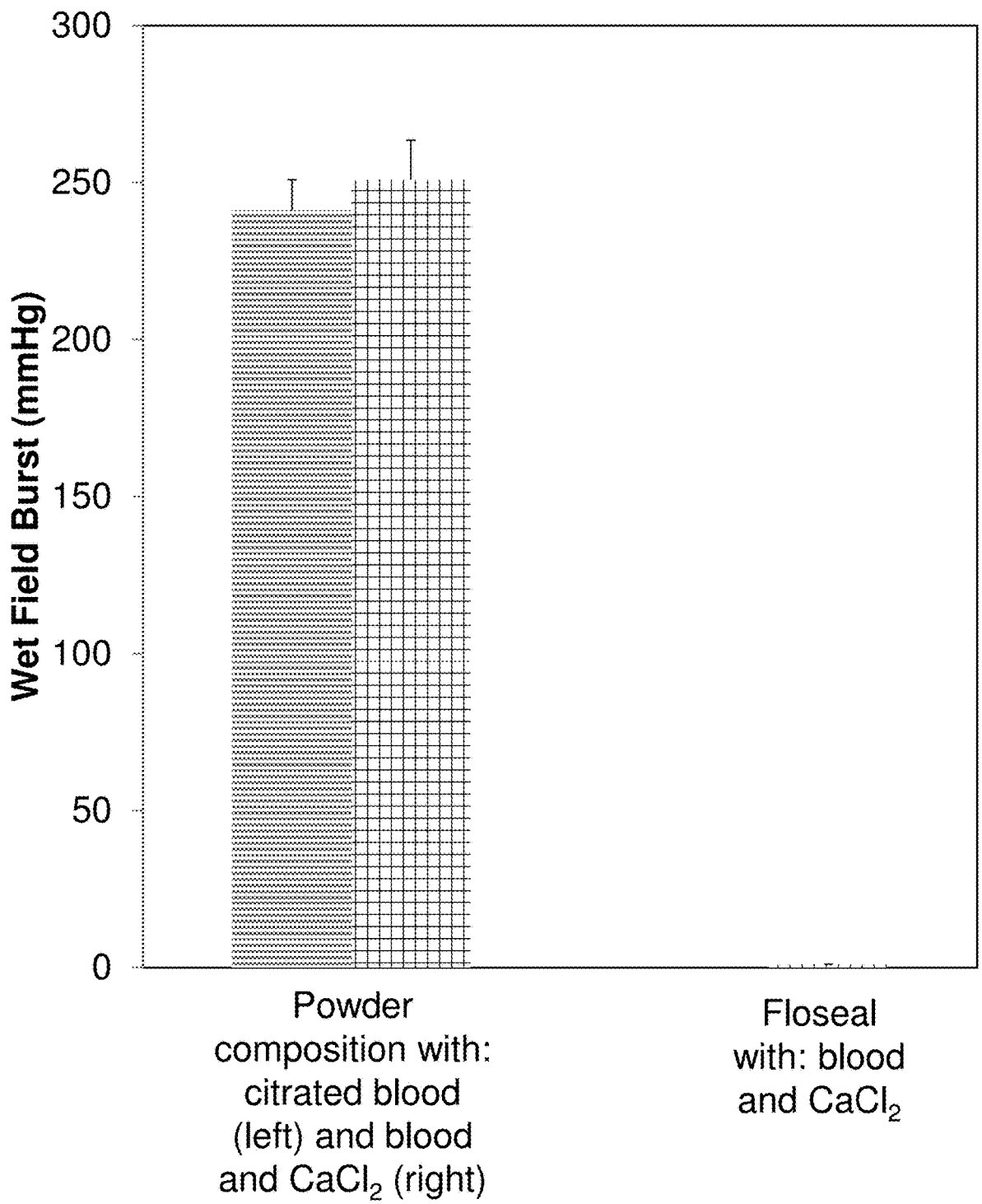
FIG. 3 shows, in accordance with certain embodiments, the wet field burst strength of a dry powdered composition as compared to a commercially available hemostat.
Figure 4A:
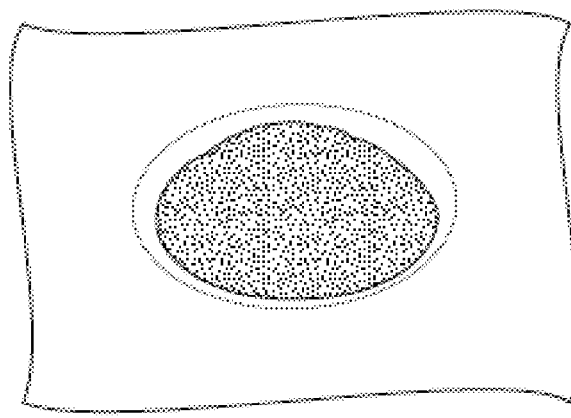
FIG. 4A shows, in accordance with certain embodiments, a line drawing of an image of a layer of blood.
Figure 4B:
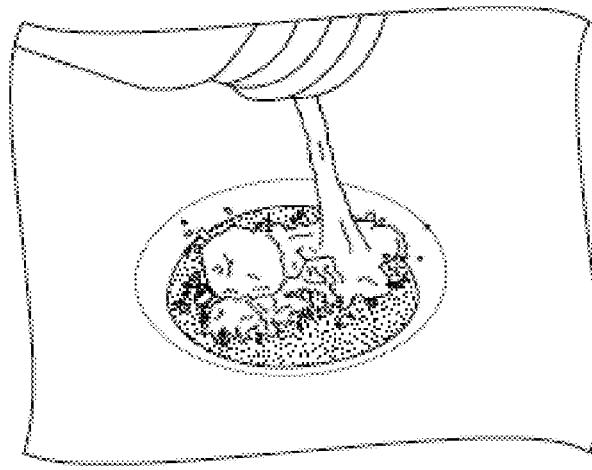
FIG. 4B shows, in accordance with certain embodiments, a line drawing of an image of the application of a dry, powdered hemostat to a layer of blood.
Figure 4C:
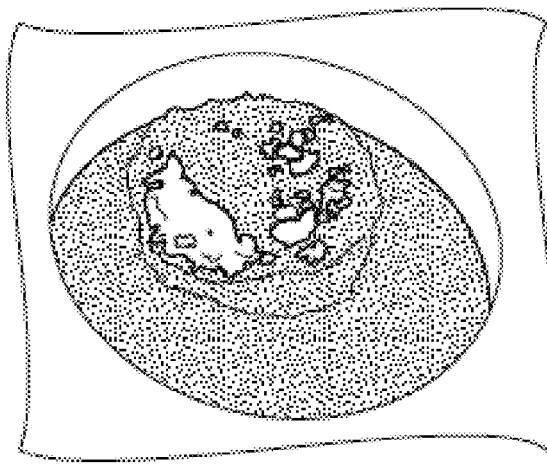
FIG. 4C shows, in accordance with certain embodiments, a line drawing of an image showing the formation of a hemostatic hydrogel on the layer of blood.

The following example describes the evaluation of sealant properties of a PEG(SS)2 dry powder composition in an in vitro burst pressure model (e.g., a modified wet field model). The material prepared in Example 1 was tested in an in vitro burst pressure model (based on ASTM F2392-04; Standard Test Method for Surgical Sealants) as described previously in Example 4. However, in order to increase the adherence challenge, the material was applied with a layer of blood already on the collagen membrane instead of blotting the membrane dry prior to placement. Citrated whole sheep's blood (0.3 mL) was applied to the surface of the collagen membrane (see FIG. 4A). This amount had a depth of approximately 1.5 mm. The material prepared in Example 1 was applied to the layer of blood and allowed to cure for 5 minutes (see FIG. 4B and FIG. 4C). A syringe pump supplied saline to the fixture at a flow rate of 2 mL/min and burst pressure at failure was measured. The material exhibited sealant properties through the layer of blood, as shown in FIG. 3, and performed orders of magnitude better than a commercially available hemostatic agent.

Example 7

The following example describes the measured crosslink time of a PEG(SS)2 dry powder composition. The crosslinking rate of the material prepared in Example 1 was tested in a measured crosslink time assay as described above. Briefly, 664 microliters of saline was added to a 15.5 mm×50 mm vial and stirred with a 3 mm×12.7 mm micro stir bar at 60 rpm. Then, 166 mg of the powdered material was added to the vial and a timer was started. The crosslink time was measured as the time when the stir bar stopped due to the formation of the crosslinked hydrogel. The crosslink time was measured in both saline and recalcified citrated whole sheep's blood (631 microliters of blood and 33 microliters of 0.2 M $CaCl_2$). The measured crosslink time of the material was faster in blood than in saline at 37° C., as shown in Table 5.

TABLE 5

Measured crosslink time of a PEG(SS)2 dry powder material in blood and saline.

| | Crosslink time in blood (sec) | Crosslink time in saline (sec) |
|---|---|---|
| Average (n = 5) | 44.4 | 76.6 |
| Standard deviation (n = 5) | 6.9 | 15.8 |

Example 8

The following example describes the effect of the amount of base on the measured crosslink time of a PEG(SS)2 dry powder composition. The dry powder material was prepared by mixing PEG(SS)2 (119 mg), bovine serum albumin (BSA) (228 mg) and various amounts of sodium bicarbonate and/or calcium chloride ($CaCl_2$). The calcium chloride was used in order to keep the composition ratios fixed, including the salt concentration. The measured crosslink time was measured as described in Example 7, and the resulting pH of the hydrogel was measured with a surface electrode. The results in Table 6 show the importance of sodium bicarbonate content on obtaining a basic pH and fast measured crosslink time.

TABLE 6

Effect of the amount of base on the crosslink time of a dry powder material.

| Weight % Sodium bicarbonate | Weight % Calcium chloride | Crosslink time in blood (mean ± std. dev.) (sec) | pH in blood (mean ± std. dev.) | Crosslink time in saline (mean ± std. dev.) (sec) | pH in saline (mean ± std. dev.) |
|---|---|---|---|---|---|
| 30 | 0 | 56.6 ± 12.5 | 9.2 ± 0.2 | 83.6 ± 17.7 | 8.7 ± 0.1 |
| 22.5 | 7.5 | 112.7 ± 41.2 | 8.6 ± 0.3 | 244.5 ± 27.4 | 7.7 ± 0.6 |
| 15 | 15 | 136.6 ± 45.6 | 8.1 ± 0.4 | 798.4 ± 79.9 | 7.0 ± 0.3 |
| 7.5 | 22.5 | 141.4 ± 44.5 | 7.4 ± 0.3 | 1058.8 ± 179.3 | 6.8 ± 0.1 |
| 0 | 30 | 133.8 ± 10.0 | 6.2 ± 0.4 | 8253.3 ± 665.8 | 4.9 ± 0.1 |

Example 9

Figure 6A:
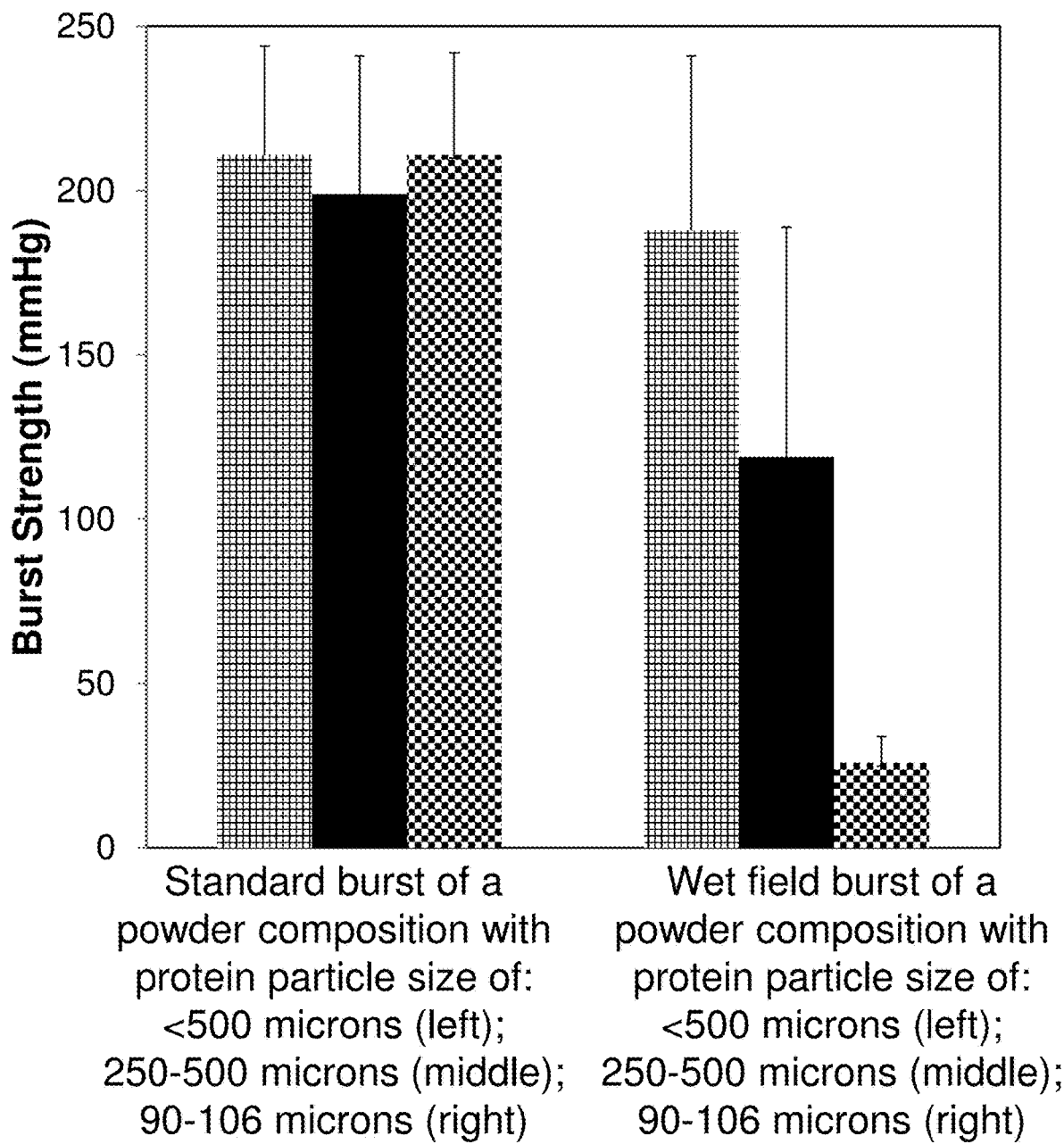
FIG. 6A shows, in accordance with certain embodiments, the effect of protein particle size on the burst strength of a dry powdered composition.
Figure 6B:
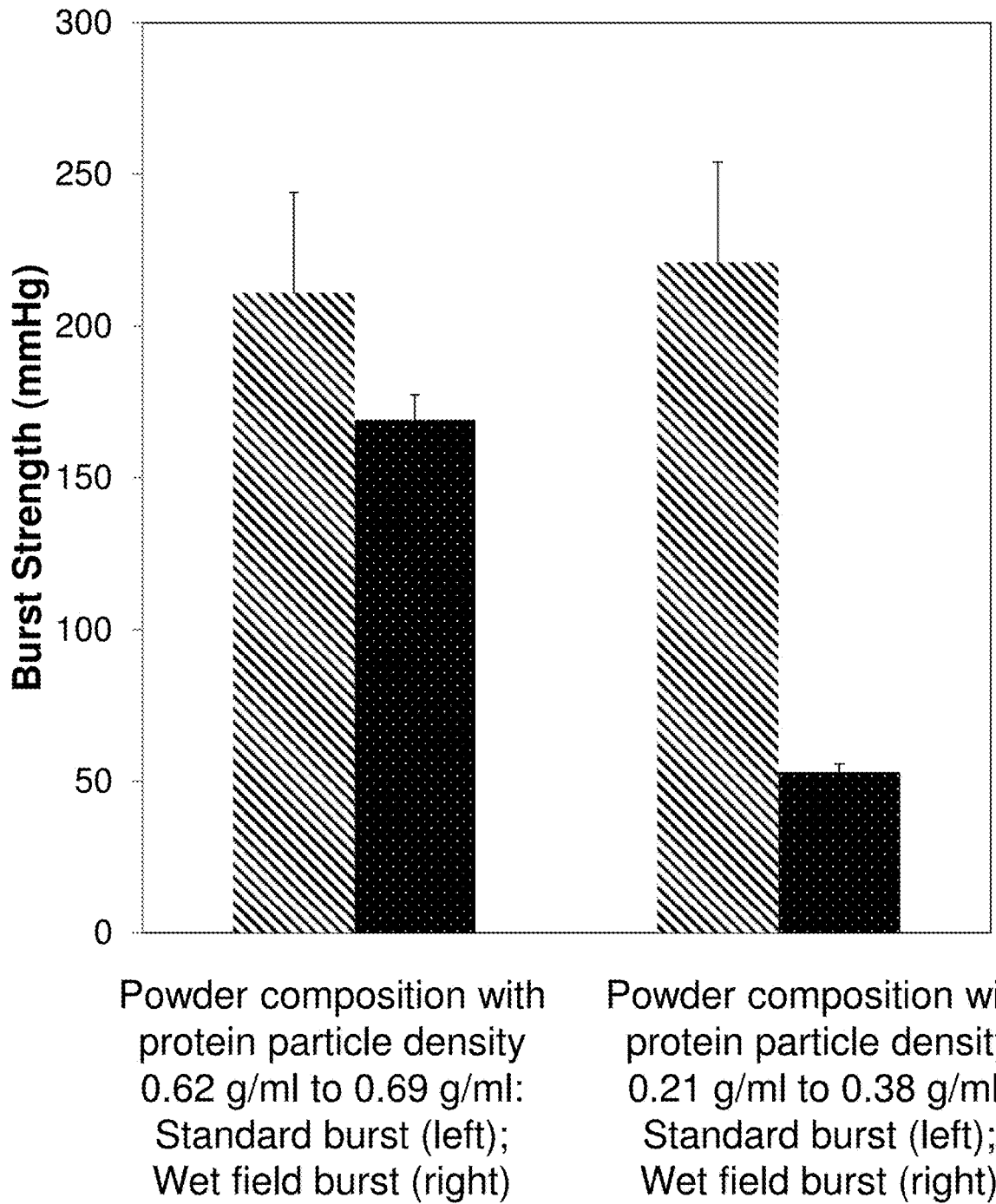
FIG. 6B shows, in accordance with certain embodiments, the effect of protein particle density on the burst strength of a dry powdered composition.

The following example describes the effect of protein particle size and protein particle density on the measured crosslink time of a dry powder composition. The material was prepared as in Example 1, but with BSA of different particle sizes and particle densities. The BSA with different particle sizes were obtained by sieving the starting BSA powder. The particle density of the BSA powder was measured by the tapped density method described previously and ranged from 0.62 g/mL to 0.69 g/mL. Lower density protein particles were made by dissolving the starting BSA powder at concentrations of 30% w/v and 7.5% w/v in deionized water, followed by lyophilizing the solutions. The resulting tapped densities of the lyophilized BSA powders were 0.38 g/mL and 0.21 g/mL for the 30% w/v and 7.5% w/v solutions, respectively. The reactive powders were tested in the standard burst strength model and the modified wet field burst strength model as described in Example 4 and Example 6, respectively. Measured crosslink time in blood and saline was also determined as described in Example 8. The results indicated that smaller particle sizes and lower particle densities had reduced performance in the wet field burst strength model that was not evident in the standard model, as shown in FIG. 6A and FIG. 6B. In addition, the mid-range particle sizes displayed the fastest measured crosslink time, as shown in Table 7.

TABLE 7

Effect of the particle size on the crosslink time of a dry powder material.

| Albumin particle size (microns) | Average (n = 3) crosslink time in blood (sec) | Standard deviation (n = 3) crosslink time in blood (sec) | Average (n = 3) crosslink time in saline (sec) | Standard deviation (n = 3) crosslink time in saline (sec) |
|---|---|---|---|---|
| 250-500 | 56.88 | 3.12 | 94.10 | 7.00 |
| 106-250 | 36.94 | 4.37 | 55.82 | 1.73 |
| <106 | 63.15 | 1.42 | 202.68 | 70.33 |
| 1-500 | 44.2 | 6.87 | 76.58 | 15.79 |

Example 10

Figure 5:
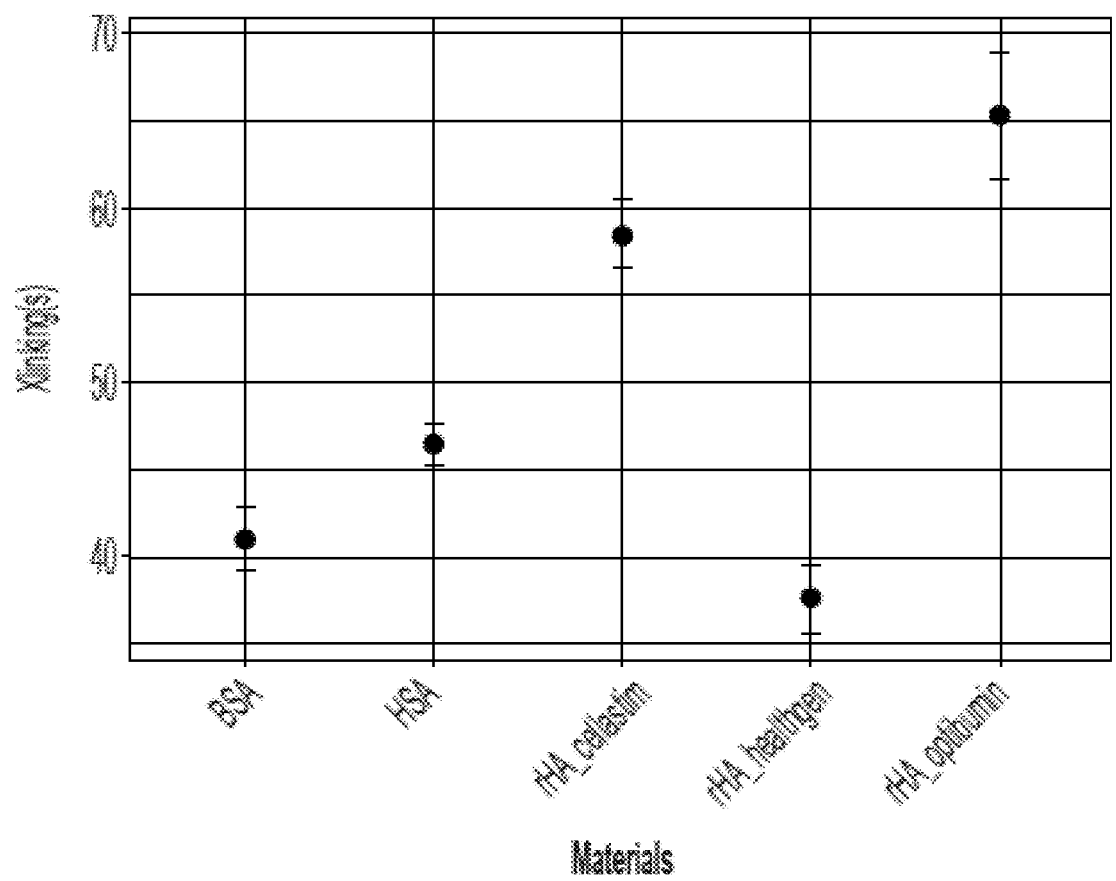
FIG. 5 shows, in accordance with certain embodiments, the effect of using various sources of albumin on the measured crosslink time of a dry powdered composition.

The following example describes the effect of using to various types of albumin on the measured crosslink time (determined as in Example 8) of a dry powder material. The material was prepared as in Example 1, but with albumin from different sources, including bovine serum albumin, human serum albumin, and various sources of recombinant human albumin. All of the varieties of albumin used in the reactive powder material crosslinked into tissue adherent hydrogels. The measured crosslink time in blood of the mixtures varied, as shown in FIG. 5, which may be due to the various particle sizes and/or densities of the albumin.

Example 11

The following example describes a comparison of various hydrogel properties resulting from altering the ratio of components of the dry powder mixture. Various dry powder mixtures (i.e., Samples) were formulated as shown in Table 8. The bovine serum albumin (BSA) and PEG(SS)2 particles were sieved to remove particles with a particle size greater than 500 micrometers.

TABLE 8

Amounts of components of a dry, powdered mixture.

| Sample | Amount of BSA (g) | Amount of PEG(SS)2 (g) | Amount of NaHCO₃ (g) | BSA/PEG(SS)2 Mass Ratio |
|---|---|---|---|---|
| 1 | 0.5696 | 0.270 | 0.1604 | 2.110 |
| 2 | 0.6098 | 0.305 | 0.0852 | 1.999 |
| 3 | 0.6148 | 0.300 | 0.0852 | 2.049 |
| 4 (30 wt. % NaHCO₃) | 0.4560 | 0.238 | 0.3060 | 1.916 |
| 5 | 0.6600 | 0.170 | 0.1700 | 3.882 |
| 6 | 0.4618 | 0.305 | 0.2332 | 1.514 |
| 7 (1 wt. % NaHCO₃) | 0.6500 | 0.340 | 0.0100 | 1.912 |
| 8 | 0.3540 | 0.340 | 0.3060 | 1.041 |
| 9 | 0.5468 | 0.220 | 0.2332 | 2.485 |
| 10 (3 wt. % NaHCO₃) | 0.6370 | 0.333 | 0.0300 | 1.913 |
| 11 | 0.6148 | 0.220 | 0.1652 | 2.795 |

The experimental values reported for each parameter discussed below and shown in Tables 9 and 10 are an average of multiple trials (n), as indicated in each table.

The measured crosslink time of each sample was evaluated as described herein. The measured crosslink time of samples 1-6, 8, 9, and 11 were each less than 120 seconds. Samples 7 and 10, with low sodium bicarbonate levels, had crosslink times that were greater than the other samples (i.e., 300 seconds and 120 seconds, respectively).

The standard burst strength of each sample was evaluated. Sample 7 had adhesive failures and a significantly lower burst strength (i.e., 50 mm Hg) as compared to the other samples, each of which had mean burst strengths between greater than 100 mm Hg and less than 200 mm Hg.

An ElastoSens™ Bio² instrument was used to evaluate the viscoelastic properties of the samples. The maximum shear elastic modulus (G' max) was evaluated for each sample. Sample 7 exhibited a significantly higher G' max (i.e., ~20000 Pa) as compared to the other samples, each of which were between greater than 7500 Pa and less than 15000 Pa. The results generally correlated with the amount of sodium bicarbonate in the sample, such that samples with less sodium bicarbonate (and more BSA and PEG(SS)2) exhibited a higher G' max.

The maximum gelation rate (max gelation rate) was also evaluated using the ElastoSens™ Bio² instrument. Samples 7 and 8 had significantly lower max gelation rates (i.e., less than 100 Pa/sec) as compared to the other samples, each of which has a max gelation rate between greater than 125 Pa/sec and less than 325 Pa/sec. Samples 9 and 11, both with a high BSA/PEG(SS)2 ratio, had max gelation rates that were significantly higher than the other groups (i.e., ~270 Pa/sec and ~325 Pa/sec, respectively).

The time of maximum gelation rate (time of max gelation rate) was also evaluated using the ElastoSens™ Bio² instrument. This parameter is the time at which the maximum rate of hydrogel formation occurred. Samples 7 and 10, with low sodium bicarbonate levels, had times of max gelation rates that were significantly slower (i.e., ~62 seconds and ~50 seconds, respectively), than the other samples (i.e., less than 42 seconds). The results generally correlated with the amount of sodium bicarbonate in the sample, such that samples with less sodium bicarbonate took longer to reach the max gelation rate.

The time to reach a G' of 5000 Pa was also evaluated using the ElastoSens™ Bio² instrument. This parameter is the time at which the hemostatic hydrogel has a shear elastic modulus 4-5 times higher than a blood clot. Samples 7 and 8 took longer (e.g., greater than 75 seconds) to reach a G' of 5000 Pa as compared to the other samples, each of which took less than 55 seconds to reach a G' of 5000 Pa. Sample 11 had the shortest time to reach a G' of 5000 Pa (~23 seconds).

The shear elastic modulus (G') at 150 seconds was also evaluated using the ElastoSens™ Bio² instrument. The 150 second time mark was chosen because it is the time allowed for the hydrogel to cure in the west burst test method. Sample 8 had a low G' at 150 seconds (i.e., ~3500 Pa), while sample 11 had a higher G' at 150 seconds (i.e. ~11500 Pa).

The surface pH of the samples was also measured. Samples 7 and 10, with low sodium bicarbonate levels, had surface pH values (i.e., ~6.5 and ~7, respectively) that were lower than the other groups, each of which had a surface pH of greater than ~8.

TABLE 9

Experimental values obtained using the formulations in Table 8.

| Sample | Measured crosslink time (mean ± std. dev.) (sec) | Standard burst strength (mean ± std. dev.) (mm Hg) | Surface pH |
|---|---|---|---|
| 1 | 76 ± 10 (n = 10) | 153 ± 50 (n = 10) | 8.2 ± 0.4 (n = 5) |
| 2 | 90 ± 6 (n = 10) | 150 ± 46 (n = 10) | 8.3 ± 0.4 (n = 5) |
| 3 | 93 ± 14 (n = 10) | 185 ± 42 (n = 10) | 8.1 ± 0.6 (n = 5) |
| 4 (30 wt. % NaHCO₃) | 79 ± 13 (n = 10) | 191 ± 35 (n = 10) | 8.5 ± 0.2 (n = 10) |
| 5 | 75 ± 9 (n = 10) | 186 ± 46 (n = 10) | 8.4 ± 0.2 (n = 10) |
| 6 | 76 ± 14 (n = 10) | 147 ± 54 (n = 10) | 8.4 ± 0.2 (n = 10) |
| 7 (1 wt. % NaHCO₃) | 317 ± 81 (n = 10) | 44 ± 23 (n = 10) | 6.4 ± 0.3 (n = 10) |
| 8 | 107 ± 42 (n = 10) | 112 ± 53 (n = 10) | 8.8 ± 0.2 (n = 10) |
| 9 | 82 ± 16 (n = 10) | 169 ± 30 (n = 10) | 8.6 ± 0.2 (n = 10) |
| 10 (3 wt. % NaHCO₃) | 135 ± 32 (n = 10) | 149 ± 47 (n = 10) | 7.0 ± 0.4 (n = 10) |
| 11 | 74 ± 9 (n = 10) | 194 ± 30 (n = 10) | 8.3 ± 0.2 (n = 10) |

TABLE 10

ElastoSens™ Bio² experimental values determined using the formulations in Table 8.

| Sample | G' Max (mean ± std. dev.) (Pa) | Max gelation rate (mean ± std. dev.) (Pa/sec) | Time of max gelation rate (mean ± std. dev.) (sec) | Time to reach G' of 5000 Pa (mean ± std. dev.) (sec) | G' at 150 seconds (mean ± std. dev.) (Pa) |
|---|---|---|---|---|---|
| 1 | 11455 ± 2565 (n = 10) | 168 ± 17 (n = 10) | 34 ± 5 (n = 10) | 50 ± 10 (n = 10) | 7477 ± 1631 (n = 10) |
| 2 | 12997 ± 1668 (n = 5) | 186 ± 24 (n = 6) | 33 ± 6 (n = 5) | 40 ± 7 (n = 4) | 8414 ± 1559 (n = 5) |
| 3 | 14998 ± 1252 (n = 9) | 190 ± 18 (n = 9) | 41 ± 7 (n = 9) | 39 ± 3 (n = 8) | 9037 ± 1385 (n = 10) |
| 4 (30 wt. % NaHCO₃) | 8517 ± 2132 (n = 10) | 157 ± 42 (n = 10) | 33 ± 8 (n = 10) | 40 ± 6 (n = 9) | 6316 ± 1624 (n = 10) |
| 5 | 8099 ± 1104 (n = 9) | 212 ± 53 (n = 10) | 30 ± 6 (n = 10) | 33 ± 6 (n = 10) | 7184 ± 1296 (n = 9) |
| 6 | 11527 ± 1635 (n = 10) | 169 ± 42 (n = 10) | 35 ± 8 (n = 10) | 46 ± 10 (n = 8) | 7014 ± 1612 (n = 10) |
| 7 (1 wt. % NaHCO₃) | 20419 ± 2987 (n = 10) | 88 ± 15 (n = 10) | 63 ± 10 (n = 10) | 74 ± 9 (n = 10) | 9857 ± 534 (n = 9) |
| 8 | 9180 ± 2309 (n = 10) | 95 ± 10 (n = 10) | 37 ± 5 (n = 10) | 257 ± 75 (n = 10) | 3833 ± 760 (n = 10) |
| 9 | 10779 ± 1993 (n = 10) | 263 ± 31 (n = 10) | 31 ± 3 (n = 10) | 30 ± 5 (n = 10) | 8909 ± 1749 (n = 10) |
| 10 (3 wt. % NaHCO₃) | 15357 ± 1580 (n = 10) | 145 ± 24 (n = 9) | 51 ± 12 (n = 9) | 53 ± 7 (n = 9) | 7895 ± 487 (n = 9) |
| 11 | 13591 ± 1689 (n = 10) | 327 ± 34 (n = 10) | 27 ± 3 (n = 10) | 24 ± 3 (n = 10) | 11549 ± 1192 (n = 10) |

Example 12

The following example describes a comparison of various hydrogel properties resulting from altering the ratio of components of the dry powder mixture. Various dry powder mixtures (i.e., Samples) were formulated based on the amounts shown in Table 11. The bovine serum albumin (BSA) particles were sieved to remove particles with a particle size greater than 500 micrometers.

TABLE 11

Relative amounts of components of a dry, powdered mixture.

| Sample | Amount of BSA (g) | Amount of PEG(SS)2 (g) | Amount of NaHCO₃ (g) | BSA/PEG(SS)2 mass ratio |
|---|---|---|---|---|
| 1 | 0.6600 | 0.3100 | 0.030 | 2.13 |
| 2 | 0.6375 | 0.2875 | 0.075 | 2.22 |
| 3 | 0.6500 | 0.2600 | 0.090 | 2.50 |
| 4 | 0.6100 | 0.2400 | 0.150 | 2.54 |
| 5 | 0.6150 | 0.2650 | 0.120 | 2.32 |
| 6 | 0.6150 | 0.2200 | 0.165 | 2.80 |
| 7 | 0.6700 | 0.2700 | 0.060 | 2.48 |

The experimental values reported for each parameter discussed below and shown in Tables 12 and 13 are an average of multiple trials (n), as indicated in each table.

The measured crosslink time of each sample was evaluated as described herein. The measured crosslink time of samples 1 and 7, which had the lowest amounts of sodium bicarbonate, were 168 seconds and 99 seconds, respectively. The additional samples had a measured crosslink time between less than 90 seconds and greater than 60 seconds.

The wet field burst strength was evaluated. All samples exhibited a mean wet field burst strength between greater than 130 mm Hg and less than 210 mm Hg.

An ElastoSens™ Bio² instrument was used to evaluate the viscoelastic properties of the samples. The maximum shear elastic modulus (G' max) was evaluated for each sample. Sample 6 had the largest amount of sodium bicarbonate (16.5 wt. %) and the lowest G' max value (~14000 Pa). The G' max of the other samples ranged from less than 18500 Pa to greater than 14900 Pa.

The maximum gelation rate (max gelation rate) was also evaluated using the ElastoSens™ Bio² instrument. Samples 1 and 7, which had the lowest amounts of sodium bicarbonate, had lower max gelation rates (i.e., ~125 Pa/sec and ~145 Pa/sec, respectively). The max gelation rates of the other samples were between less than 235 Pa/sec and greater than 195 Pa/sec.

The time of maximum gelation rate (time of max gelation rate) was also evaluated using the ElastoSens™ Bio² instrument. Samples 1 and 7 had greater times of max gelation rate (each 52 seconds) as compared to the other samples, each of which had a time of max gelation rate between greater than 32 second and less than 41 seconds.

The time to reach a G' of 5000 Pa was also evaluated using the ElastoSens™ Bio² instrument. Samples 1 and 7 had the longest times to reach a G' of 5000 Pa at ~56 seconds and ~54 seconds, respectively. The other samples took between 32 seconds and 39 seconds to reach a G' of 5000 Pa.

The shear elastic modulus (G') at 150 seconds was also evaluated using the ElastoSens™ Bio² instrument. Samples 1 and 7 had the lowest G' at 150 seconds (i.e., ~11450 Pa and ~10350 Pa, respectively). The G' at 150 seconds for samples 2-6 was between less than 13800 Pa and greater than 11700 Pa.

TABLE 12

Experimental values obtained using the formulations in Table 11.

| Sample | Measured crosslink time (mean ± std. dev.) (sec) | Wet field burst strength (mean ± std. dev.) (mm Hg) |
|---|---|---|
| 1 | 168 ± 41 (n = 5) | 149 ± 77 (n = 10) |
| 2 | 89 ± 11 (n = 5) | 201 ± 55 (n = 10) |

TABLE 12-continued

Experimental values obtained using the formulations in Table 11.

| Sample | Measured crosslink time (mean ± std. dev.) (sec) | Wet field burst strength (mean ± std. dev.) (mm Hg) |
|---|---|---|
| 3 | 85 ± 17 (n = 5) | 155 ± 66 (n = 10) |
| 4 | 79 ± 10 (n = 5) | 142 ± 71 (n = 10) |
| 5 | 64 ± 4 (n = 5) | 189 ± 62 (n = 10) |
| 6 | 63 ± 4 (n = 5) | 184 ± 73 (n = 10) |
| 7 | 99 ± 10 (n = 5) | 154 ± 43 (n = 10) |

TABLE 13

ElastoSens™ Bio$^2$ experimental values determined using the formulations in Table 11.

| Sample | G' Max (mean ± std. dev.) (Pa) | Max gelation rate (mean ± std. dev.) (Pa/sec) | Time of max gelation rate (mean ± std. dev.) (sec) | Time to reach G' of 5000 Pa (mean ± std. dev.) (sec) | G' at 150 seconds (mean ± std. dev.) (Pa) |
|---|---|---|---|---|---|
| 1 | 17708 ± 2026 (n = 12) | 126 ± 15 (n = 12) | 52 ± 12 (n = 12) | 56 ± 9 (n = 12) | 11449 ± 1801 (n = 12) |
| 2 | 18476 ± 1821 (n = 12) | 211 ± 26 (n = 12) | 40 ± 5 (n = 12) | 38 ± 5 (n = 12) | 13743 ± 1374 (n = 12) |
| 3 | 17128 ± 1313 (n = 12) | 197 ± 34 (n = 12) | 39 ± 6 (n = 12) | 39 ± 7 (n = 12) | 13156 ± 1360 (n = 12) |
| 4 | 15066 ± 1089 (n = 12) | 232 ± 25 (n = 12) | 33 ± 3 (n = 12) | 32 ± 3 (n = 12) | 12867 ± 797 (n = 12) |
| 5 | 17546 ± 1271 (n = 12) | 217 ± 27 (n = 12) | 40 ± 5 (n = 12) | 39 ± 5 (n = 12) | 13619 ± 1141 (n = 11) |
| 6 | 14116 ± 893 (n = 12) | 218 ± 28 (n = 12) | 38 ± 5 (n = 12) | 36 ± 4 (n = 12) | 11760 ± 1071 (n = 12) |
| 7 | 14972 ± 1374 (n = 12) | 145 ± 22 (n = 12) | 52 ± 13 (n = 12) | 54 ± 11 (n = 12) | 10360 ± 1286 (n = 12) |

Example 13

The following example describes a comparison of various hydrogel properties resulting from altering the density and particle size of human serum albumin (HSA) in the dry powdered mixture. Dry powder mixtures (i.e., Samples) were prepared using HSA with various combinations of density and particle size as shown in Table 14. The "low" density groups used the starting HSA powder (e.g., less than 0.4 g/mL) and the "high" density group used the rolled compacted HSA powder (greater than 0.5 g/mL). The "low", "medium", and "high" particle size groups correspond to HSA powder sieved to particle size targets of less than 106 micrometers, between 106 and 250 micrometers, and between 250 and 500 micrometers, respectively.

TABLE 14

Relative amounts of components of a dry, powdered mixture.

| Sample | Density | Particle Size | HSA Particle Size Targets (micrometers) |
|---|---|---|---|
| 1 | Low | Low | <106 |
| 2 | Low | Medium | 106-250 |
| 3 | Low | High | 250-500 |
| 4 | High | Low | <106 |
| 5 | High | Medium | 106-250 |
| 6 | High | High | 250-500 |
| 7 | Low | Full Range | 1:1:1 blend of the 3 sizes |
| 8 | High | Full Range | 1:1:1 blend of the 3 sizes |

The experimental values reported for each parameter listed below and shown in Tables 15 and 16 are an average of multiple trials (n), as indicated in each table.

The measured crosslink time of each sample was evaluated as described herein. Sample 1, with low density and smaller sized HSA particles, sat on the surface of the liquid and no crosslinking was observed within 180 seconds. Samples 2 and 3, with low density particles that were larger than the particles in Sample 1, crosslinked in less than 60 seconds. The particle sizes in Samples 2 and 3 were observed to better penetrate the liquid surface, as compared to Sample 1, and because the particles were low density they dissolved quickly to participate in the crosslinking reaction. Sample 4 also crosslinked in less than 60 seconds. Samples 6, 7, and 8 each had crosslink times greater than 100 seconds, presumably due to the higher density of the particles, which solubilized slower than the low density particles.

The wet field burst strength of each sample was evaluated. All samples exhibited a mean wet field burst strength between 90 and 200 mm Hg.

An ElastoSens™ Bio$^2$ instrument was used to evaluate the viscoelastic properties of the samples. The maximum shear elastic modulus (G' max) was evaluated for each sample. The G' max of Sample 6 (e.g., less than 10000 Pa) was lower than the other groups, each of which had a G' max between greater than 12500 Pa and less than 21000 Pa.

The maximum gelation rate (max gelation rate) was also evaluated using the ElastoSens™ Bio$^2$ instrument. Sample 6 had the lowest max gelation rate (less than 100 Pa/sec). The other samples had max gelation rates between greater than 200 Pa/sec and less than 700 Pa/sec.

The time of maximum gelation rate (time of max gelation rate) was also evaluated using the ElastoSens™ Bio$^2$ instrument. Samples 1 and 4, with HSA particles less than 106 micrometers, had longer times of max gelation rates (~53 seconds and ~63 seconds, respectively), as compared to the other samples, each of which has a time of max gelation rate between less than 30 seconds and greater than 15 seconds.

The time to reach a G' of 5000 Pa was also evaluated using the ElastoSens™ Bio$^2$ instrument. Sample 6 had the longest time to reach a G' of 5000 Pa (~90 seconds), presumably due to the slower solubility of the larger, density HSA particles. Samples 1 and 4 both took greater than 40 seconds to reach a G' of 5000 Pa, presumably due to the small particle size. Samples 2, 3, 5, 7, and 8 reached a G' of 5000 Pa in less than 20 seconds.

The shear elastic modulus (G') at 150 seconds was also evaluated using the ElastoSens™ Bio$^2$ instrument. Samples 4 and 6 had a shear elastic modulus less than 10000 Pa at 150 seconds, while the other samples had a shear elastic modulus between greater than 12500 Pa and less than 17500 Pa at 150 seconds.

TABLE 15

Experimental values obtained using the formulations in Table 14.

| Sample | Measured crosslink time (mean ± std. dev.) (sec) | Wet field burst strength (mean ± std. dev.) (mm Hg) |
|---|---|---|
| 1 | ≥180 (n = 10) | 117 ± 78 (n = 10) |
| 2 | 48 ± 3 (n = 10) | 163 ± 41 (n = 10) |
| 3 | 56 ± 4 (n = 10) | 190 ± 53 (n = 10) |
| 4 | 55 ± 3 (n = 10) | 90 ± 58 (n = 10) |
| 5 | 67 ± 6 (n = 10) | 140 ± 69 (n = 10) |
| 6 | 120 ± 28 (n = 10) | 160 ± 54 (n = 10) |
| 7 | 95 ± 25 (n = 10) | 165 ± 61 (n = 10) |
| 8 | 158 ± 36 (n = 10) | 173 ± 59 (n = 10) |

TABLE 16

ElastoSens™ Bio² experimental values determined using the formulations in Table 14.

| Sample | G' Max (mean ± std. dev.) (Pa) | Max gelation rate (mean ± std. dev.) (Pa/sec) | Time of max gelation rate (mean ± std. dev.) (sec) | Time to reach G' of 5000 Pa (mean ± std. dev.) (sec) | G' at 150 seconds (mean ± std. dev.) (Pa) |
|---|---|---|---|---|---|
| 1 | 15729 ± 1878 (n = 8) | 326 ± 97 (n = 7) | 54 ± 9 (n = 7) | 47 ± 6 (n = 8) | 14655 ± 1501 (n = 8) |
| 2 | 16075 ± 1760 (n = 9) | 482 ± 90 (n = 10) | 17 ± 3 (n = 10) | 15 ± 3 (n = 10) | 14862 ±1380 (n = 10) |
| 3 | 14901 ± 1359 (n = 10) | 206 ± 22 (n = 10) | 30 ± 7 (n = 10) | 34 ± 4 (n = 10) | 12782 ± 973 (n = 10) |
| 4 | 13057 ± 2304 (n = 9) | 277 ± 109 (n = 9) | 63 ± 14 (n = 9) | 52 ± 17 (n = 9) | 9660 ± 1839 (n = 9) |
| 5 | 14837 ± 1770 (n = 10) | 344 ± 45 (n = 10) | 21 ± 4 (n = 10) | 19 ± 4 (n = 10) | 13577 ± 1292 (n = 10) |
| 6 | 9079 ± 1008 (n = 10) | 73 ± 12 (n = 10) | 18 ± 7 (n = 10) | 94 ± 10 (n = 10) | 6963 ± 821 (n = 10) |
| 7 | 16748 ± 2004 (n = 10) | 407 ± 94 (n = 10) | 23 ± 4 (n = 10) | 21 ± 4 (n = 10) | 14907 ± 1337 (n = 10) |
| 8 | 20949 ± 3906 (n = 9) | 661 ± 100 (n = 10) | 24 ± 6 (n = 10) | 21 ± 5 (n = 10) | 17321 ± 2656 (n = 9) |

Example 14

The following example describes the standard burst strength of a crosslinked hydrogel formed from a dry powdered composition at 0 hours and 24 hours. The dry powdered composition contained 24 wt. % PEG(SS)2, 61 wt. % bovine serum albumin (BSA), and 15 wt. % sodium bicarbonate. Samples were prepared for burst testing as described previously. Half of the samples were tested at t=0 (e.g., the time of hydration) and half were removed from the burst fixture and placed in phosphate buffered saline (PBS) at 37° C. The PBS was replaced after 1 hour to maintain neutral pH. After 24 hours, the samples were removed from the PBS still attached to the collagen substrate, returned to the fixture and burst tested. The data shown below in Table 17 indicated that the hemostatic hydrogel maintained sufficient burst strength in vitro for 24 hours.

TABLE 17

Burst strength of a dry powdered hemostatic composition at 0 and 24 hours.

| Time (hours) | Sample size | Max Burst Strength (mean ± std. dev.) (mm Hg) | Burst Strength Range (mm Hg) |
|---|---|---|---|
| 0 | 10 | 201 ± 50 | 92-255 |
| 24 | 9 | 152 ± 18 | 118-183 |

Example 15

The following example describes the hemostatic efficacy of various dry powder mixtures in a porcine spleen biopsy defect model. Various dry powder mixtures (i.e., Samples) were formulated as shown in Table 18.

TABLE 18

Various formulations of dry powder mixtures used to evaluate the hemostatic efficiency in a porcine spleen biopsy defect model.

| Sample | Formulation | Wt. % Albumin | Wt. % PEG(SS)2 | Wt. % Unmodified PEG | Wt. % NaHCO₃ |
|---|---|---|---|---|---|
| 1 | PEG(SS)2 w/BSA | 61 | 24 | 0 | 15 |
| 2 | PEG(SS)2 w/HSA | 61 | 24 | 0 | 15 |
| 3 | 70% functional PEG(SS)2 | 61 | 16.8 | 7.2 | 15 |
| 4 | 50 wt. % functional PEG(SS)2 | 61 | 12 | 12 | 15 |
| 5 | PEG(SS)2 w/spray coated HSA/SB | 61 | 24 | 0 | 15 |
| 6 | 85 wt. % functional PEG(SS)2 | 61 | 20.4 | 3.6 | 15 |
| 7 | 120 wt. % functional PEG(SS)2 | 56 | 29 | 0 | 15 |

Heparin was administered to each animal to mimic clinically relevant coagulopathies and heparinization during cardiovascular surgery. An IV bolus of heparin was given initially to increase the activated clotting time (ACT) to ≥2-3× baseline and periodically thereafter for maintenance. In order to increase the hemostatic challenge in a realistic surgical scenario, the dry powdered material was applied to an actively bleeding site, instead of blotting the defect dry prior to placement. A 10 mm diameter biopsy defect to a depth of 5 mm was made in the spleen. The defect was allowed to fill with blood and then the sample powder mixture (0.5 g) was applied to the defect and a 2.5-3 cm×2.5-3 cm starch foam or carboxymethylcellulose (CMC) tamponade was placed on top of the powder to prevent it from adhering to the gauze used for application of the tamponade. Initial hemostasis was assessed after each 10 second tamponade pressure application cycle for a duration of 30 seconds. If the defect remained hemostatic for the duration of the 30 second observation, it was declared initially hemostatic. If the defect was still bleeding, additional tamponade cycles were applied. If hemostasis was achieved for 30 seconds after any of the tamponade cycles, the defect was observed for an additional 5 minutes to check for rebleeding. Results are shown in Table 19.

TABLE 19

Hemostatic efficacy of various dry powder mixtures in a heparinized porcine spleen abrasion model.

| Sample | Formulation | # of Defects Treated | # of Pressure Cycles (mean ± std. dev.) | % of Defects Achieving and Maintaining Hemostasis (5 min Observation) |
|---|---|---|---|---|
| 1 | PEG(SS)2 w/BSA | 12 | 1.4 ± 1.2 | 92 |
| 2 | PEG(SS)3 w/HSA | 12 | 1.3 ± 0.7 | 92 |
| 3 | 70% functional PEG(SS)2 | 12 | 2.2 ± 2.2 | 83 |
| 4 | 50 wt. % functional PEG(SS)2 | 12 | 5.1 ± 4.4 | 50^ |
| 5 | PEG(SS)2 w/spray coated HSA/SB | 12 | 1.9 ± 1.1 | 92 |
| 6 | 85 wt. % functional PEG(SS)2 | 12 | 2.6 ± 3.3 | 83 |
| 7 | 120 wt. % functional PEG(SS)2 | 12 | 2.1 ± 2.5 | 92 |
| Control | Floseal | 8 | 8.9 ± 2.2 | 0 |

Example 16

The following example describes the hemostatic efficacy of dry powder mixtures comprising albumin of different particle sizes in a porcine spleen biopsy defect model. Samples were prepared and evaluated as explained in Example 15. Smaller album particles ranged from 54 to 299 micrometers, while larger albumin particles ranges from 101 to 547 micrometers. The data tabulated in Table 20 shows that smaller particles generally have a negative effect on hemostatic efficiency.

TABLE 20

Hemostatic efficacy of various dry powder mixtures in a heparinized porcine spleen abrasion model.

| Formulation | # of Defects Treated | # of Pressure Cycles (mean ± std. dev.) | % of Defects Achieving Hemostasis in One Pressure Cycle |
|---|---|---|---|
| Dry powder mixture w/ smaller albumin particles | 5 | 2.0 ± 1.7 | 60 |
| Dry powder mixture w/ larger albumin particles | 5 | 1.0 ± 0.0 | 100 |

Example 17

The following example describes the hemostatic efficacy of dry powder mixtures comprising varying amounts of sodium bicarbonate in a porcine spleen biopsy defect model. Samples were prepared and evaluated as explained in Example 15. The data tabulated in Table 21 show that lower sodium bicarbonate levels generally have a negative effect on hemostatic efficacy.

TABLE 21

Hemostatic efficacy of various dry powder mixtures comprising different amounts of sodium bicarbonate in a heparinized porcine spleen abrasion model.

| Sample | # of Defects Treated | # of Pressure Cycles (mean ± std. dev.) | % of Defects Achieving Hemostasis in One Pressure Cycle |
|---|---|---|---|
| Dry powder mixture with 1 wt. % NaHCO$_3$ (30 second pressure cycles) | 6 | 2.3 ± 1.4 | 33 |
| Dry powder mixture with 3 wt. % NaHCO$_3$ (30 second pressure cycles) | 6 | 1.3 ± 0.5 | 67 |
| Dry powder mixture with 16.5 wt. % NaHCO$_3$ (30 second pressure cycles) | 5 | 1.8 ± 1.8 | 80 |
| Dry powder mixture with 30 wt. % NaHCO$_3$ (30 second pressure cycles) | 3 | 1.0 ± 0.0 | 100 |
| Dry powder mixture with 16.5 wt. % NaHCO$_3$ (30 second pressure cycles) | 4 | 2.3 ± 2.5 | 75 |

Example 18

The following example describes the effect of various fluids used to hydrate the dry powdered mixture on hydrogel formation. A dry powdered mixture was prepared with 24 wt. % PEG(SS)2, 61 wt. % albumin, and 15 wt. % sodium bicarbonate. The dry powder mixture was hydrated with the fluids shown in Table 22. The pH and viscoelastic properties were then evaluated (where applicable).

TABLE 22

Various fluids used to hydrate a dry powdered mixture and the resulting experimental parameters.

| Sample | Description | pH | G' Max (Pa) | G' at 150 seconds (Pa) | Time to reach G' of 5000 Pa (sec) |
|---|---|---|---|---|---|
| Reference | Citrated blood with CaCl$_2$ without added dry powdered mixture | Not evaluated | 1276 | 0 | N/A |
| 1 | Dry powdered mixture + PBS | 7.2-7.4 | 12986 | 10267 | 31 |
| 2 | Dry powdered mixture + 0.03M HCl | 1.5 | 13467 | 7041 | 67 |
| 3 | Dry powdered mixture + Citrated blood | 7.35-7.45 | 42990 | 40057 | 9 |
| 4 | Dry powdered mixture + Citrated blood with CaCl$_2$ | Not evaluated | 51450 | 46046 | immediate |

The dry powder mixture was able to hydrate and quickly crosslink in all four fluids to form a simulated hydrogel clot with a higher modulus than a reference blood clot. The lower strength clots were formed from the dry powder mixture hydrated with PBS or a very acidic simulated gastric fluid (0.03 M hydrochloric acid) and the clot strength in both fluids were still at least 9-10 times higher than a reference blood clot. The clots formed by polymerizing the dry powder mixture with citrated blood or citrated blood with calcium chloride were much higher in strength with a modulus of 30-40 times that of a blood clot, supporting that the dry powder mixture can function in a variety of coagulopathic situations.

Example 19

The following example demonstrates hemostatic sealant properties of a PEG(SS)2-based dry powder mixture using a second component comprising HSA that has undergone pH adjustment prior to mixing with the PEG(SS)2-containing first component. The pH of samples of dissolved diagnostic-grade HSA was adjusted by starting with 25 w/v % HSA United States Pharmacopeia (USP) standard solution or by preparing a 25 w/v % HSA solution in deionized water. While slowly mixing the initial HSA solution and measuring pH, 1 N sodium hydroxide (NaOH) aqueous solution was slowly added until a target pH was reached, forming "starting HSA solutions" having an adjusted pH. The pH of each solution was monitored using an Orion™ 9107BN (Thermo Fisher, Waltham, MA) pH probe. Next, the starting HSA solutions were poured into 150×150 mm trays (12.7 mm fill height) and lyophilized at −40° C. under a 33 Pa vacuum environment. The resulting lyophilized solids were then milled into powders, which were sieved to select for particles with a size of 106-500 micrometers. The particles comprising pH-adjusted HSA were then vacuum dried and blended with PEG(SS)2 powder in the desired final proportion for each sample. Samples had different starting pH values for HSA (corresponding to the value of the pH-adjusted starting HSA solutions), with starting pH values ranging between 8 and 9.5. Two control samples used starting HSA solutions that were not pH-adjusted—one sample comprising a sodium bicarbonate ($NaHCO_3$) powder crosslinking initiator (sample 20), and one comprising no base or basic buffer powder at all (sample 19)—both having a starting HSA solution pH of 7.11. The ratio of HSA/PEG (SS)2 in the final blend powder composition was also varied. Table 23 reports the estimated final composition by weight of each component of each blended powder mixture sample, as well as the HSA/PEG(SS)2 weight ratio, the starting HSA solution pH. Table 23 also reports a percentage by weight of "NaOH" in the pH-adjusted HSA particles following lyophilization/milling as well as in the final blend composition. These values reflect (and are calculated from) the known amount of NaOH added to the starting HSA solutions prior to lyophilization. It should be understood that some (or all) of the added NaOH will react with the HSA in solution (e.g., in a neutralization reaction to at least partially deprotonate the HSA). Therefore, the resulting powder particles may not literally contain intact, ionically-bound solid NaOH, but may rather contain corresponding reaction products (e.g., sodium ions bound to counteranions). However, some intact NaOH powder may be present in instances where a molar excess of NaOH is added with respect to acidic protons in the starting HSA solution. For each sample, the measurements collected and described below were performed using 7-9 replicates.

TABLE 23

Composition of starting HSA solutions and resulting blend mixture of samples.

| Sample | w/v % of 1N NaOH in Starting HSA Solution | Starting HSA Solution pH | w/w % NaOH in HSA particles | Final Blend Composition (w/w %) | | | | HSA/PEG (SS)2 Weight Ratio in Blend |
|---|---|---|---|---|---|---|---|---|
| | | | | % HSA | % NaOH | % $NaHCO_3$ | % PEG(SS)2 | |
| 12 | 1.77 | 8.06 | 0.29 | 67.65 | 0.20 | 0.00 | 32.15 | 2.05 |
| 13 | 1.77 | 8.06 | 0.29 | 72.69 | 0.21 | 0.00 | 27.10 | 2.61 |
| 14 | 5.03 | 9.51 | 0.84 | 69.74 | 0.59 | 0.00 | 29.67 | 2.18 |
| 15 | 2.44 | 8.48 | 0.40 | 69.60 | 0.28 | 0.00 | 30.12 | 2.23 |
| 16 | 5.03 | 9.51 | 0.84 | 71.31 | 0.60 | 0.00 | 28.09 | 2.36 |
| 17 | 2.44 | 8.48 | 0.40 | 72.83 | 0.29 | 0.00 | 26.88 | 2.61 |
| 18 | 3.38 | 8.94 | 0.56 | 70.36 | 0.40 | 0.00 | 29.24 | 2.27 |
| 19 | 0.00 | 7.11 | 0.00 | 69.97 | 0.00 | 0.00 | 30.03 | 2.33 |
| 20 | 0.00 | 7.11 | 0.00 | 61.00 | 0.00 | 15.00 | 24.00 | 2.54 |

The particle density of the blended powder mixtures of each sample was measured by the tapped density method described previously and ranged from 0.29 g/mL to 0.36 g/mL. This was compared with the bulk density (the mass of the powder divided by the measured volume of the powder before tapping). The ratio of tapped density to bulk density (the Hausner ratio) can provide a measure of particle flowability and compressibility. Results are presented in Table 24. Similar analysis was performed on the lyophilized, pH adjusted HSA particles after sieving, but before mixing into the samples, and these results are presented in Table 25. Particle size distributions for the samples were measured by laser light scattering, and Table 26 reports the $10^{th}$ percentile (D10), the $50^{th}$ percentile (D50), and the $90^{th}$ percentile (D90) of particle size for each sample.

TABLE 24

Bulk density, tap density, and Hausner Ratio determined for blended powder samples of the formulations in Table 23.

| Sample | Bulk Density (g/mL) | Tap Density (g/mL) | Hausner Ratio |
|---|---|---|---|
| 12 | 0.247 | 0.307 | 1.24 |
| 13 | 0.238 | 0.291 | 1.22 |
| 14 | 0.28 | 0.332 | 1.19 |
| 15 | 0.262 | 0.311 | 1.19 |
| 16 | 0.268 | 0.318 | 1.19 |
| 17 | 0.263 | 0.299 | 1.14 |
| 18 | 0.27 | 0.315 | 1.17 |
| 19 | 0.258 | 0.315 | 1.22 |
| 20 | 0.294 | 0.356 | 1.21 |

TABLE 25

Bulk density, tap density, and Hausner Ratio determined for the pH-adjusted lyophilized HSA powders.

| w/v % of 1N NaOH in Starting HSA Solution | Used in Blended Powder Sample No. from Table 23 | Bulk Density (g/mL) | Tap Density (g/mL) | Hausner Ratio |
|---|---|---|---|---|
| 1.8 | 12 and 13 | 0.24 | 0.31 | 1.29 |
| 2.4 | 15 and 17 | 0.25 | 0.33 | 1.32 |
| 3.4 | 18 | 0.26 | 0.33 | 1.24 |
| 5.0 | 14 and 16 | 0.29 | 0.33 | 1.13 |

TABLE 26

Particle size distribution statistics determined for blended powder samples of the formulations in Table 23.

| Group | D10 (micrometers) | D50 (micrometers) | D90 (micrometers) |
|---|---|---|---|
| 12 | 64.3 | 256 | 499 |
| 13 | 68.1 | 245 | 439 |
| 14 | 66.3 | 265 | 511 |
| 15 | 69.2 | 250 | 514 |
| 16 | 75 | 273 | 514 |
| 17 | 73.3 | 254 | 646 |
| 18 | 71.9 | 256 | 529 |
| 19 | 71 | 258 | 496 |
| 20 | 78.6 | 278 | 649 |

The samples prepared in this example were tested in a modified wet field burst strength model as described in Example 6, except using a 2.5 minute cure time instead of a 5 minute cure time. Table 27 reports the mean burst pressure (in mmHg) for each sample, as well as the standard deviation. With the exception of Control Sample 19 (the control sample with no pH adjustment and no separate crosslinking initiator), the mean burst pressure of all samples exceeded 90 mmHg, a clinically useful value. These results demonstrate that pH-adjustment of HSA to at least partially deprotonate that HSA can facilitate formulation of dry, hemostatic powder compositions having satisfactory performance even without inclusion of separate dry powder base or basic buffer components (e.g., sodium bicarbonate).

TABLE 27

Wet Field Burst pressure statistics determined for the formulations in Table 23.

| Sample | Mean Wet Field Burst Strength (mmHg) | Std. Deviation (mmHg) | Minimum (mmHg) | Maximum (mmHg) |
|---|---|---|---|---|
| 12 | 175.07 | 69.188 | 56.653 | 286.67 |
| 13 | 175.69 | 64.146 | 74.6 | 280.8 |
| 14 | 164.78 | 61.278 | 113 | 265.5 |
| 15 | 178.77 | 67.225 | 40.4 | 272.8 |
| 16 | 151.84 | 49.651 | 98.9 | 236.9 |
| 17 | 178.86 | 70.440 | 72.9 | 269.8 |
| 18 | 143.35 | 46.394 | 92.4 | 216.6 |
| 19 | 109.45 | 66.785 | 30 | 226.4 |
| 20 | 269.81 | 10.498 | 257 | 284.8 |

Example 20

The following example describes the assessment of hemostatic hydrogel bubble entrapment in Sample 16 and Control Sample 20 of Example 19. To document evidence of bubble formation, hemostatic hydrogels were photographed and inspected. Out of five hemostatic hydrogels from Sample 16, three showed evidence of only a small amount of trapped air/gas. Two hemostatic hydrogels from Sample 16 showed no evidence of entrapment of air or gas. In hemostatic hydrogels from Control Sample 20, entrapped bubbles were observed in all of the five hemostatic hydrogels. Qualitatively, the bubbles of Control Sample 20 were observed to be larger in size. Trapped air and gas in the center of the hemostatic hydrogels and small micro-bubbling observed at the edge of the hemostatic hydrogel provided further evidence for the enhanced entrapment of gas within gels of Control Sample 20. These observations are believed to result from the conversion of $NaHCO_3$ into water and gaseous carbon dioxide upon reaction with acidic species in an aqueous environment. Thus, in some cases, pH-adjustment of HSA as performed in Example 19 may advantageously reduce the entrapment of gasses within hemostatic hydrogels.

Example 21

The following example describes the viscoelastic properties of hemostatic hydrogels formed from the PEG(SS)2-based dry powder mixture samples of Example 19. Rheological experiments were performed according to the methods described in Examples 11 and 12 (using 1× phosphate buffered saline (PBS) as the aqueous medium) in order to determine the maximum shear elastic modulus (G' max), the maximum gelation rate (max gelation rate), the time of max gelation rate, and the time to reach a G' of 5000 Pa were collected for 20 hemostatic hydrogels from each sample.

The mean values of G' max, max gelation rate, time to max gelation rate, and time to reach a G' of 5000 Pa (as well as the standard deviation of these) is presented in Table 28. In addition, the surface pH each hemostatic hydrogel was measured according to the method using an Orion™ 81358BN (Thermo Fisher) pH probe with a sympHony™ SB70P (VWR® International, Radnor, PA) pH meter. These data are compared with the pH of the starting HSA solution that was originally reported in Table 29.

TABLE 28

ElastoSens™ Bio² experimental values determined using the formulations in Table 23.

| Sample | G' Max (Pa) | | Max Gelation Rate (Pa/s) | | Time to max gelation rate (s) | | Time to reach G' = 5000 Pa (s) | |
|---|---|---|---|---|---|---|---|---|
| | Mean | Std. Dev. | Mean | Std. Dev. | Mean | Std. Dev. | Mean | Std. Dev. |
| 12 | 17439 | 4316.4 | 119.37 | 43.596 | 265.23 | 35.908 | 88.4 | 31.458 |
| 13 | 13756 | 1633.4 | 81.434 | 34.833 | 190 | 108.18 | 94.267 | 31.491 |
| 14 | 29318 | 3680.0 | 234.87 | 38.641 | 49.7 | 46.853 | 19 | 3.6144 |
| 15 | 17650 | 2177.8 | 155.18 | 129.26 | 131.75 | 90.766 | 66.787 | 15.574 |
| 16 | 30547 | 5842.3 | 210.65 | 76.552 | 77.189 | 105.07 | 20.289 | 8.2272 |
| 17 | 19662 | 2040.6 | 117.29 | 53.781 | 213.24 | 121.07 | 56.643 | 19.445 |
| 18 | 24447 | 3127.1 | 173.73 | 26.582 | 41.533 | 57.624 | 31.889 | 7.0144 |
| 19 | 5104.2 | 202.89 | 33.698 | 3.6112 | 276.32 | 19.993 | 296.77 | 4.8760 |
| 20 | 18172 | 1174.2 | 183.87 | 64.410 | 51.844 | 11.149 | 49.4 | 4.4637 |

TABLE 29

Starting pH of pH-adjusted HSA, and measured average surface pH of hemostatic hydrogel test samples.

| Sample | Starting HSA Solution pH | Average Surface pH |
|---|---|---|
| 12 | 8.06 | 5.95 |
| 13 | 8.06 | 6.07 |
| 14 | 9.51 | 6.47 |
| 15 | 8.48 | 6.14 |
| 16 | 9.51 | 6.53 |
| 17 | 8.48 | 6.30 |
| 18 | 8.94 | 6.24 |
| 19 | 7.11 | 5.72 |
| 20 | 7.11 | 8.24 |

In general, the rheological properties of each hemostatic hydrogel sample were comparable or superior to the rheological properties of Control Sample 20. For instance, only the G' max of Sample 13 and Control Sample 19 were lower than the G' max of Control Sample 20, indicating that other hemostatic hydrogels were comparably stiff and strong, when compared with Control Sample 20. The rheological properties of Sample 13 and of Control Sample 19 are believed to result from the comparatively low pH measured for these gels, which had a surface pH of 6.07 and 5.72, respectively. The low pH of Control Sample 19 was expected, since the pH of HSA was not modified in this case. The same trend holds in the measurements of max gelation rate, with the max gelation rate of Test Sample 13 and Control Sample 19 being lower than the max gelation rate of the other samples.

In general, the time to max gelation rate tended to be related to the observed surface pH of the hemostatic hydrogel. Samples 12 and 13, as well as Control Sample 19, took longer to reach their max gelation rate than the other samples, but still within clinically acceptable ranges. Similarly, samples with higher pH tended to reach G'=5000 Pa more quickly than samples with lower pH. Multiple pH adjusted samples reached G'=5000 Pa more quickly than Control Sample 20 (specifically, Samples 14, 16, and 18).

These examples demonstrate that, in general, pH adjustment of HSA can support gelation behavior that is comparable to or exceeds the gelation behavior of PEG(SS)2-based dry powder mixture that comprises NaHCO$_3$ as a separate solid cross-linking initiator, and indicate that a greater degree of pH adjustment typically supports faster gelation as well as the formation of stronger gels.

Example 22

The following example describes the use of sodium phosphate dibasic (Na$_2$HPO$_4$) as a crosslinking initiator for PEG(SS)2-based dry powder mixtures. In this example, sodium phosphate dibasic was sieved below 250 micrometers, PEG(SS)2 was sieved below 500 micrometers, and HSA powder was sieved between 106-500 micrometers. The weight percent (w/w %) of sodium phosphate dibasic in the resulting blended dry powder was varied between 5 w/w % and 20 w/w %, while the weight ratio of HSA/PEG(SS)2 was kept relatively constant. Experiments were performed using four samples, whose compositions are summarized in Table 30.

TABLE 30

Composition of samples containing sodium phosphate dibasic.

| Sample | w/w % Sodium Phosphate Dibasic | w/w % HSA | w/w % PEG(SS)2 | HSA/PEG(SS)2 Ratio |
|---|---|---|---|---|
| 21 | 5 | 68 | 27 | 2.52 |
| 22 | 10 | 64 | 26 | 2.46 |
| 23 | 15 | 61 | 24 | 2.54 |
| 24 | 20 | 57 | 23 | 2.48 |

Rheological experiments were performed according to the methods described in Examples 11 and 12 in order to determine the maximum shear elastic modulus (G' max), the maximum gelation rate (max gelation rate), the time of max gelation rate, and the time to reach a G' of 5000 Pa were collected for hemostatic hydrogels from each sample. The mean values of G' max, max gelation rate, time to max gelation rate, and time to reach a G' of 5000 Pa (as well as the standard deviation of these) are presented in Table 31. Measurements were performed using 9 replicates.

TABLE 31

ElastoSens™ Bio² experimental values determined using the formulations in Table 23.

| Sample | G' Max (Pa) | | Max Gelation Rate (Pa/s) | | Time to Max Gelation rate (s) | | Time to reach G' = 5000 Pa (s) | |
|---|---|---|---|---|---|---|---|---|
| | Mean | Std. Dev. | Mean | Std. Dev. | Mean | Std. Dev. | Mean | Std. Dev. |
| 21 | 12598 | 1357.6 | 77.08 | 41.36 | 187 | 98.74 | 110.11 | 22.83 |
| 22 | 9899.1 | 982.5 | 77.15 | 10.74 | 39.44 | 44.33 | 80.44 | 12.45 |
| 23 | 8489.0 | 1570.9 | 112.82 | 66.23 | 44.33 | 39.45 | 63.33 | 11.53 |
| 24 | 7529.2 | 779.7 | 95.10 | 41.90 | 43.22 | 29.54 | 74.89 | 31.25 |

Generally, these results indicate that the gelation properties of PEG(SS)2-based dry powder mixtures can be substantially enhanced relative to a non-pH modified control (see Control Sample 19 of Examples 19-21), and that satisfactory performance can be achieved using a non-gas-forming basic buffer (sodium phosphate dibasic).

The hemostatic hydrogels from Sample 22 were tested in a modified wet field burst strength model as described in Example 6. The mean wet field burst strength was 124 mmHg, with a standard deviation of 92 mmHg, indicating that the hemostatic hydrogels formed form this PEG(SS)2-based dry powder mixture met clinically acceptable standards.

Example 23

The following example compares the properties of hemostatic hydrogels prepared with: a PEG(SS)2-based dry powder mixture that did not comprise a separate solid base/basic buffer crosslinking initiator but did comprise pH-adjusted HSA with a starting pH of 9.0 (Sample 25); a PEG(SS)2-based dry powder mixture that included a sodium bicarbonate crosslinking initiator (15 w/w %, Sample 26); and a PEG(SS)2-based dry powder mixture that included a sodium phosphate dibasic crosslinking initiator (10 w/w %, Sample 27). The modified wet field burst strength of each sample was determined according to the method described in Example 6, using 20 hemostatic hydrogels. The results of these experiments are summarized in Table 32.

TABLE 32

Burst strength of hemostatic hydrogels.

| Sample: | 25 | 26 | 27 |
|---|---|---|---|
| Mean Wet Field Burst Strength (mmHg) | 128.11 | 163.71 | 140.40 |
| Standard Deviation | 93.791 | 95.938 | 89.742 |

All three samples provided clinically acceptable wet field burst strengths, with no statistically significant differences between the burst strengths of each sample. This example demonstrates that all three formulations may be used to form satisfactory hemostatic hydrogels. The hemostatic efficiencies of Samples 25-27 were also compared using a heparinized porcine spleen biopsy defect model, according to the protocol described in Example 1. The results of this experiment are presented in Table 33.

TABLE 33

Hemostatic efficacy of PEG(SS)2-based dry powder mixtures in a porcine spleen biopsy defect model.

| Sample | # of Defects Treated | # of Pressure Cycles Required to Achieve Hemostasis (mean ± std. dev.) | % of Defects Achieving and Maintaining Hemostasis (2 min. Observation) |
|---|---|---|---|
| 25 | 8 | 1.0 ± 0.0 | 100 |
| 26 | 8 | 1.5 ± 1.1 | 100 |
| 27 | 8 | 1.0 ± 0.0 | 100 |

Again, these experiments demonstrate that all three PEG(SS)2-based dry powder mixtures were able to form gels that maintained hemostasis for 100% of defects, demonstrating the clinical viability of all three compositions.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively.

What is claimed is:

1. A method, comprising:
   forming a dry, powdered, crosslinking hemostatic composition comprising:
   (a) a first component comprising a difunctionalized polyalkylene oxide-based component of the formula:

G-LM-PEG-LM-G;

wherein:
   PEG is polyethylene glycol;
   each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and
   each G is a leaving group independently selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl; and
   (b) a second component comprising a solid form of a protein, wherein the solid form of the protein is prepared by a method comprising removing water from a preparatory aqueous solution comprising an at least partially dissolved form of the protein, thereby forming the solid form of the protein, wherein the preparatory aqueous solution has a pH of greater than or equal to 8.

2. The method of claim 1, further comprising combining the first component and the second component comprising the solid form of the protein to form a single powder mixture.

3. The method of claim 1, wherein:
   each LM is the same and is a difunctional linking moiety represented by the formulas —C(O)—, —$(CH_2)_b$—C(O)— where b is an integer from 1 to 5, —C(O)—$(CH_2)_c$—C(O)— where c is an integer from 2 to 10 and where the aliphatic portion of the radical may be saturated or unsaturated, —C(O)—O—$(CH_2)_d$—O—C(O)— where d is an integer from 2 to 10, and an oligomeric diradical represented by the formulas —R—C(O)—, —R—C(O)—$(CH_2)_c$—C(O)—, or R—C(O)—O—$(CH_2)_d$—O—C(O)— where c is an integer from 2 to 10, d is an integer from 2 to 10, and R is a polymer or copolymer having 1 to 10 monomeric lactide, glycolide, trimethylene carbonate, caprolactone or p-dioxanone fragments; and
   each G is the same and is a leaving group selected from the group consisting of N-oxysuccinimidyl, N-oxysulfosuccinimidyl, N-oxymaleimidyl, N-oxyphthalimidyl, nitrophenoxyl, N-oxyimidazolyl, and tresyl.

4. The method of claim 1, wherein the protein comprises serum albumin.

5. The method of claim 1, wherein the protein is selected from the group of consisting of: human serum albumin, recombinant human albumin, and animal sourced albumin.

6. The method of claim 1, wherein the protein is human serum albumin.

7. The method of claim 1, wherein the difunctionalized polyalkylene oxide-based component is of the form:

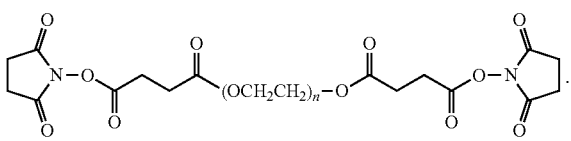

Poly(ethylene glycol) disuccinimidyl succinate

8. The method of claim 7, wherein n is from 10 to 500.

9. The method of claim 1, wherein the composition comprises a first dry powder comprising the first component and a second dry powder comprising the second component comprising the solid form of the protein.

10. The method of claim 1, wherein the composition comprises a crosslinking initiator that initiates crosslinking of the first component with the protein, wherein the crosslinking initiator comprises a base and/or a basic buffer.

11. The method of claim 10, wherein the base and/or basic buffer is non-gas-forming in aqueous solutions.

12. The method of claim 10, wherein the base and/or basic buffer comprises a salt comprising a cation and hydroxide.

13. The method of claim 10, wherein the base and/or basic buffer comprises sodium hydroxide.

14. The method of claim 1, wherein the second component, when dissolved in deionized water, can produce a pH of a resulting solution of greater than or equal to 8.

15. The method of claim 1, wherein the protein in the second component is in a basic state.

16. The method of claim 1, wherein the protein in the second component is at least partially deprotonated.

17. The method of claim 1, wherein the preparatory aqueous solution is prepared by (a) at least partially dissolving the protein in water and (b) adjusting the pH of the resulting solution such that the pH is greater than or equal to 8.

18. The method of claim 1, wherein the removing the water from the preparatory aqueous solution comprises lyophilizing the aqueous solution.

19. The method of claim 1, wherein upon exposure of 0.5 g of the composition to 1.0 mL of 0.01 M phosphate buffered saline, crosslinking of the first component and the second component is initiated to form a hemostatic hydrogel having a surface pH of less than or equal to 8.

20. The method of claim 1, wherein the composition comprises the second component in an amount of greater than or equal to 60 wt. % by mass and less than or equal to 80 wt. % by mass of the total dry, powdered composition.

21. The method of claim 20, wherein the composition comprises the first component in an amount of greater than or equal to 20 wt. % by mass and less than or equal to 40 wt. % by mass of the total dry, powdered composition.

22. The method of claim 21, wherein the composition comprises solid sodium hydroxide in an amount of greater than or equal to 0.01 wt % by mass and less than or equal to 0.5 wt % by mass of the total dry, powdered composition.

23. The method of claim 21, wherein:
the difunctionalized polyalkylene oxide-based component is of the form:

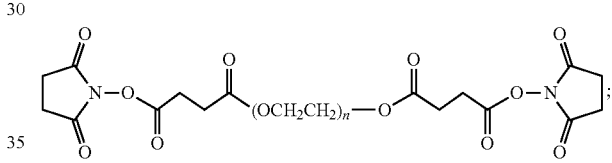

Poly(ethylene glycol) disuccinimidyl succinate and
the protein comprises serum albumin.

* * * * *

UNITED STATES PATENT AND TRADEMARK OFFICE
CERTIFICATE OF CORRECTION

| | | |
|---|---|---|
| PATENT NO. | : 12,151,045 B2 | Page 1 of 1 |
| APPLICATION NO. | : 17/562282 | |
| DATED | : November 26, 2024 | |
| INVENTOR(S) | : Keith Greenawalt et al. | |

It is certified that error appears in the above-identified patent and that said Letters Patent is hereby corrected as shown below:

In the Specification

At Column 1, Lines 9 through 15:
"This application claims priority under 35 U.S.C. § 119(e) to U.S. Provisional Patent Application No. 63/131,267, filed Dec. 28, 2020, and entitled "Reactive Dry Powder Hemostatic Materials Comprising a Protein and a Multifunctionalized Polyethylene Glycol Based Crosslinking Agent," which is incorporated herein by reference in its entirety for all purposes."

Should read:
--This application claims priority under 35 U.S.C. § 119(e) to U.S. Provisional Patent Application No. 63/131,267, filed Dec. 28, 2020, and entitled "Reactive Dry Powdered Hemostatic Materials Comprising a Protein and a Multifunctionalized Modified Polyethylene Glycol Based Crosslinking Agent," which is incorporated herein by reference in its entirety for all purposes.--

Signed and Sealed this
Twenty-second Day of April, 2025

Coke Morgan Stewart
*Acting Director of the United States Patent and Trademark Office*